(12) United States Patent
Yonekuta et al.

(10) Patent No.: US 9,899,605 B2
(45) Date of Patent: Feb. 20, 2018

(54) ORGANIC THIN FILM TRANSISTOR

(71) Applicant: FUJIFILM Corporation, Tokyo (JP)

(72) Inventors: Yasunori Yonekuta, Kanagawa (JP); Koji Takaku, Kanagawa (JP); Wataru Sotoyama, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 294 days.

(21) Appl. No.: 14/865,649

(22) Filed: Sep. 25, 2015

(65) Prior Publication Data
US 2016/0049592 A1   Feb. 18, 2016

(30) Foreign Application Priority Data

Mar. 27, 2013 (JP) ................. 2013-067346
Mar. 12, 2014 (JP) ................. 2014-048650

(51) Int. Cl.
H01L 51/00  (2006.01)
C07F 7/18  (2006.01)
(Continued)

(52) U.S. Cl.
CPC ........ H01L 51/0071 (2013.01); C07D 498/06 (2013.01); C07D 513/06 (2013.01);
(Continued)

(58) Field of Classification Search
CPC combination set(s) only.
See application file for complete search history.

(56) References Cited

U.S. PATENT DOCUMENTS 5,349,062 A * 9/1994 Zambounis ........... C07C 331/30
544/14

FOREIGN PATENT DOCUMENTS

DE    2224746 A1   11/1973
JP   H06-073065 A   3/1994

OTHER PUBLICATIONS

Notification of Transmittal of Translation of the International Preliminary Report on Patentability and Translation of Written Opinion of the International Searching Authority; PCT/JP2014/057528; dated Oct. 8, 2015.
(Continued)

*Primary Examiner* — Peter F Godenschwager
*Assistant Examiner* — Andrew J Oyer
(74) *Attorney, Agent, or Firm* — Studebaker & Brackett PC

(57) ABSTRACT

An organic thin film transistor containing a compound represented by the formula (1) in a semiconductor active layer has a high carrier mobility, a small change in the threshold voltage after repeated driving and a high solubility in an organic solvent. $A^1$ and $A^2$ represent S, O or Se; at least one of $R^1$ to $R^6$ represents a substituent represented by *-L-R wherein L represents a divalent linking group and R represents a hydrogen atom, an alkyl group, an oligooxyethylene group, an oligosiloxane group or a trialkylsilyl group.

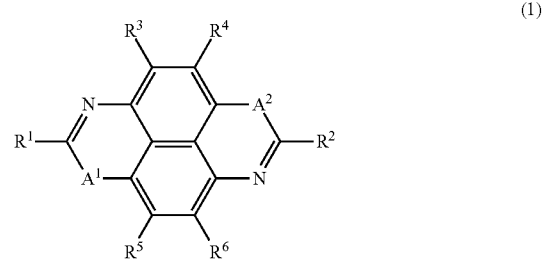

(1)

11 Claims, 2 Drawing Sheets

(51) Int. Cl.
    C07F 7/08      (2006.01)
    C07D 517/06    (2006.01)
    C07D 498/06    (2006.01)
    C07D 513/06    (2006.01)
    H01L 51/05     (2006.01)

(52) U.S. Cl.
    CPC .......... C07D 517/06 (2013.01); C07F 7/0812 (2013.01); C07F 7/0849 (2013.01); C07F 7/1804 (2013.01); H01L 51/0058 (2013.01); H01L 51/0065 (2013.01); H01L 51/0068 (2013.01); H01L 51/0094 (2013.01); H01L 51/0545 (2013.01)

(56) References Cited

OTHER PUBLICATIONS

Zambounis et al., "Synthesis, Properties, and Metallic Cation Radical Salts of a New Class of Electron π-Donors: 2,7-Disubstituted Naphtho[1,8-de:5,4-d'e']bis[1,3]thiazines", Journal of American Chemical Society, 1994, pp. 925-931, vol. 116, No. 3.

International Search Report and Written Opinion of International Searching Authority from PCT/JP2014/057528 dated Apr. 28, 2014.

PCT International Preliminary Report on Patentability and Written Opinion dated Oct. 8, 2015, issued in corresponding PCT Application No. PCT/JP2014/057528, with English translation.

The extended European search report issued by the European Patent Office dated Jan. 4, 2016, which corresponds to European Patent Application No. 14775347.9 and is related to U.S. Appl. No. 14/865,649.

* cited by examiner

ORGANIC THIN FILM TRANSISTOR

CROSS-REFERENCE TO RELATED APPLICATIONS

This application is a Continuation of PCT International Application No. PCT/JP2014/057528, filed on Mar. 19, 2014, which claims priority under 35 U.S.C. Section 119(a) to Japanese Patent Application No. 2013-067346 filed on Mar. 27, 2013, and Japanese Patent Application No. 2014-048650 filed on Mar. 12, 2014. Each of the above applications is hereby expressly incorporated by reference, in its entirety, into the present application.

BACKGROUND OF THE INVENTION

Field of the Invention

The present invention relates to an organic thin film transistor, an organic semiconductor thin film, and an organic semiconductor material. More specifically, the invention relates to a compound having a naphthobisthiazine structure or an analog skeleton structure thereof, or a component having a naphthobisselenazin structure or an analog skeleton structure thereof, an organic thin film transistor containing the compound, an organic semiconductor material for a non-light emitting organic semiconductor device containing the compound, a material for an organic thin film transistor containing the compound, a coating solution for a non-light emitting organic semiconductor device containing the compound, and an organic semiconductor thin film for a non-light emitting organic semiconductor device containing the compound.

Background Art

A device using an organic semiconductor material is expected to have various advantages as compared to an ordinary device using an inorganic semiconductor material, such as silicon, and thus is receiving much attention. Examples of the device using an organic semiconductor material include a photoelectric conversion device, such as an organic thin film solar cell and a solid state image sensing device, using an organic semiconductor material as a photoelectric conversion material, and a non-light emitting organic transistor. The device using an organic semiconductor material has a possibility that a device having a large area may be produced at a low temperature and a low cost, as compared to a device using an inorganic semiconductor material. Furthermore, the characteristics of the material may be easily changed by changing the molecular structure thereof, and thus there is a wide range of variations in materials, by which functions and devices that have not been achieved by an inorganic semiconductor material may be realized.

For example, Patent Document 1 and Non-patent Document 1 describe a compound having a naphtobisthiazine structure, which is in needle shape and has surprisingly high electrical conductivities. Moreover, this compound having a naphtobisthiazine structure can be blended into plastic materials as electrically conductive fillers, or used for preparation of sensors. However, Patent Document 1 and Non-patent Document 1 do not describe or suggest the purpose of an organic transistor.

Patent Document 2 describes tetrachloronaphtothiazine derivates as plant protective agents and dye intermediate, and a method for efficiently preparing the tetrachloronaph- tothiazine derivates. However, Patent Document 2 does not describe or suggest the purpose of an organic transistor.

CITATION LIST

Patent DocumentS

[Patent Document 1] JP-A-6-73065
[Patent Document 2] DE 2224746 A

Non-Patent Document

[Non-patent Document 1] Journal of America Chemical Society, 116, 925 (1994)

SUMMARY OF INVENTION

Patent Document 1 and Non-patent Document 1 describe that a naphthobisthiazine substituted by an organic thio, oxy or seleno group is useful as electrically conductive fillers since it forms electrically conductive charge transfer complexes with inorganic anions. The electrically conductive fillers are generally an inorganic material such as carbon particles, metal power or metal oxide powder, and conductive ceramics power; or charge transfer complexes, which are difficult to be used as an active layer of a thin-film transistor independently or in combination with other substances. The electrically conductive fillers are a conductor, thus unsuitable for a switching element such as transistor.

Actually, the present inventors actually apply the polycyclic condensed compound in Patent Document 1, Non-patent Document 1 or Patent Document 2 having an aromatic heterocyclic ring applied to an organic EL device to an organic thin film transistor, but it has been found that there is a problem that sufficient transistor characteristics are not obtained. Specifically, in the case where the compounds that are described with specific structures thereof in Patent Document 1, Non-patent Document 1 and Patent Document 2 are applied as an organic semiconductor material to an organic thin film transistor, the investigations made by the inventors reveal that a high carrier mobility is not obtained. Furthermore, the investigations made by the inventors reveal that the change in the threshold voltage becomes large in repeated driving. The large change in the threshold voltage brings about a problem that the transistor is deteriorated in reliability and may not be used for a prolonged period of time. The change in the threshold voltage after repeated driving is a problem that has not been known in the art.

Under the circumstances, the inventors have made investigations for solving the problems in the related art. An object to be achieved by the invention is to provide an organic thin film transistor that has a high carrier mobility, a small change in the threshold voltage after repeated driving and a high solubility in an organic solvent.

As a result of earnest investigations for solving the problems, the inventors have found that an organic thin film that has advantageously a high carrier mobility may be obtained by such a manner that the particular substituent is introduced to the thiazine ring position and/or selenazine position and/or naphthalene position constituting a naphthobisthiazine and a ring of the analog skeleton thereof, or a naphthobisselenazine and a ring of the analog skeleton thereof. It has been found that an organic thin film transistor having a high carrier mobility is obtained thereby.

Furthermore, the inventors have found that an organic thin film transistor that uses a compound having a naphthobisthiazine structure or an analog skeleton structure thereof, or a component having a naphthobisselenazin structure or an analog skeleton structure thereof in a semiconductor active layer shows a small change in the threshold voltage after repeated driving, and thus have completed the invention.

The invention as a specific measure for solving the problems includes the following aspects.

[1] An organic thin film transistor containing a compound represented by the following formula (1) in a semiconductor active layer:

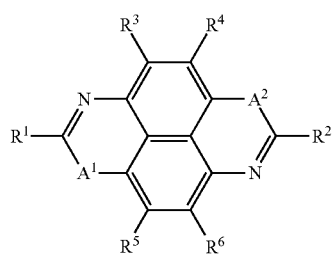

Formula (1)

wherein in the formula (1), $A^1$ and $A^2$ each independently represent a sulfur atom, an oxygen atom or a selenium atom; and $R^1$ to $R^6$ each independently represent a hydrogen atom or a substituent, provided that at least one of $R^1$ to $R^6$ represents a substituent represented by the following formula (W):

*-L-R   Formula (W)

wherein in the formula (W), * represents a position bonded to a naphthalene ring in the formula (1), or bonded to a ring containing $A^1$ or a ring containing $A^2$; L represents a divalent linking group represented by any one of the following formulae (L-1) to (L-10), or a divalent linking group consisting of 2 or more divalent linking groups each represented by any one of the following formulae (L-1) to (L-10) in which the 2 or more divalent linking groups are bonded sequentially; and R represents a hydrogen atom, a substituted or unsubstituted alkyl group, an oligooxyethylene group having a repeating number of an oxyethylene unit of 2 or more, an oligosiloxane group having 2 or more silicon atoms, or a substituted or unsubstituted trialkylsilyl group, provided that R represents a hydrogen atom only when L is represented by any one of the formulae (L-1) to (L-3) and (L-8) to (L-10), and R represents a substituted or unsubstituted trialkylsilyl group only when L bonded to R is a divalent linking group represented by the following formula (L-3);

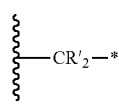
(L-1)

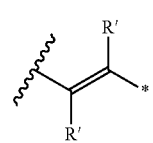
(L-2)

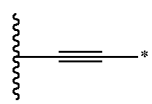
(L-3)

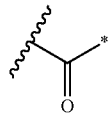
(L-4)

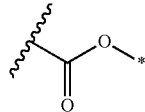
(L-5)

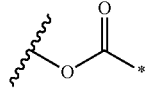
(L-6)

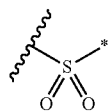
(L-7)

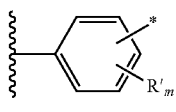
(L-8)

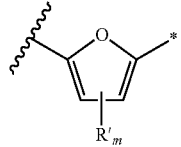
(L-9)

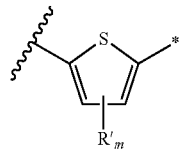
(L-10)

wherein in the formulae (L-1) to (L-10), the wavy line represents a position bonded to any one of a naphthalene ring, a ring containing $A^1$ and a ring containing $A^2$; and * represents a position bonded to R in the formula (W); in the formula (L-8), m represents 4; in the formulae (L-9) and (L-10), m represents 2; in the formulae (L-1), (L-2), (L-8), (L-9) and (L-10), R' each independently represents a hydrogen atom or a substituent, provided that, in the formulae (L-1) and (L-2), R' each independently may form a condensed ring with R bonded to L.

[2] In the organic thin film transistor according to the item [1], at least one of $R^1$ and $R^2$ in the formula (1) preferably represents a substituent represented by the formula (W).

[3] In the organic thin film transistor according to the item [1] or [2], the compound represented by the formula (1) is preferably a compound represented by the following formula (2):

Formula (2)

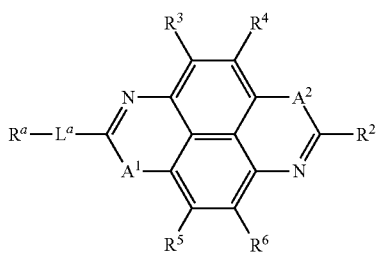

wherein in the formula (2), $A^1$ and $A^2$ each independently represent a sulfur atom, an oxygen atom or a selenium atom; $R^2$ to $R^6$ each independently represent a hydrogen atom or a substituent; $L^a$ represents a divalent linking group represented by any one of the following formulae (L-1) to (L-10), or a divalent linking group consisting of 2 or more divalent linking groups each represented by any one of the following formulae (L-1) to (L-10) in which the 2 or more divalent linking groups are bonded sequentially; and $R^a$ represents a hydrogen atom, a substituted or unsubstituted alkyl group, an oligooxyethylene group having a repeating number of an oxyethylene unit of 2 or more, an oligosiloxane group having 2 or more silicon atoms, or a substituted or unsubstituted trialkylsilyl group, provided that $R^a$ represents a hydrogen atom only when $L^a$ is represented by any one of the formulae (L-1) to (L-3) and (L-8) to (L-10), and $R^a$ represents a substituted or unsubstituted trialkylsilyl group only when $L^a$ bonded to $R^a$ is a divalent linking group represented by the following formula (L-3);

(L-1)

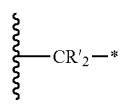

(L-2)

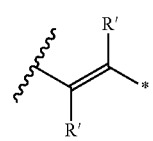

(L-3)

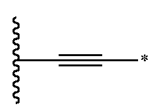

(L-4)

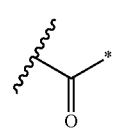

(L-5)

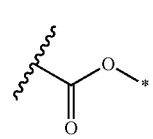

(L-6)

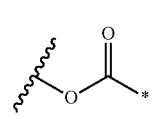

(L-7)

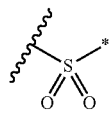

(L-8)

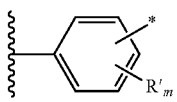

(L-9)

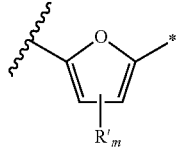

(L-10)

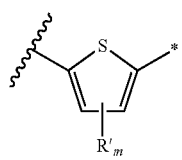

wherein in the formulae (L-1) to (L-10), the wavy line represents a position bonded to any one of a naphthalene ring, a ring containing $A^1$ and a ring containing $A^2$; and * represents a position bonded to $R^a$; in the formula (L-8), m represents 4; in the formulae (L-9) and (L-10), m represents 2; in the formulae (L-1), (L-2), (L-8), (L-9) and (L-10), R' each independently represents a hydrogen atom or a substituent, provided that, in the formulae (L-1) and (L-2), R' each independently may form a condensed ring with R bonded to L.

[4] In the organic thin film transistor according to any one of the items [1] to [3], the compound represented by the formula (1) is preferably a compound represented by the following formula (3):

Formula (3)

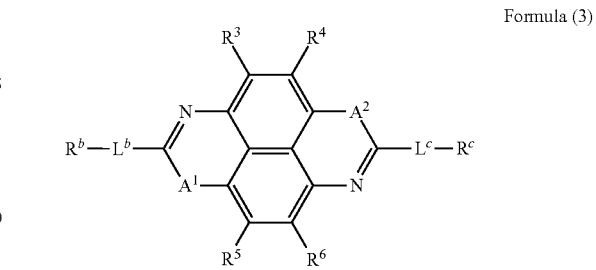

wherein in the formula (3), $A^1$ and $A^2$ each independently represent a sulfur atom, an oxygen atom or a selenium atom; $R^3$ to $R^6$ each independently represent a hydrogen atom or a substituent; $L^b$ and $L^c$ each independently represent a divalent linking group represented by any one of the following formulae (L-1) to (L-10), or a divalent linking group consisting of 2 or more divalent linking groups each represented by any one of the following formulae (L-1) to (L-10) in which the 2 or more divalent linking groups are bonded sequentially; and $R^b$ and $R^c$ each independently represent a hydrogen atom, a substituted or unsubstituted alkyl group, an oligooxyethylene group having a repeating number of an oxyethylene unit of 2 or more, an oligosiloxane group having 2 or more silicon atoms, or a substituted or unsubstituted trialkylsilyl group, provided that $R^b$ and $R^c$ represent a hydrogen atom only when $L^b$ and $L^c$ are represented by any one of the formulae (L-1) to (L-3) and (L-8) to (L-10), and $R^b$ and $R^c$ represent a substituted or unsubstituted trialkylsilyl group only when $L^b$ and $L^c$ each bonded to $R^b$ and $R^c$ are a divalent linking group represented by the following formula (L-3);

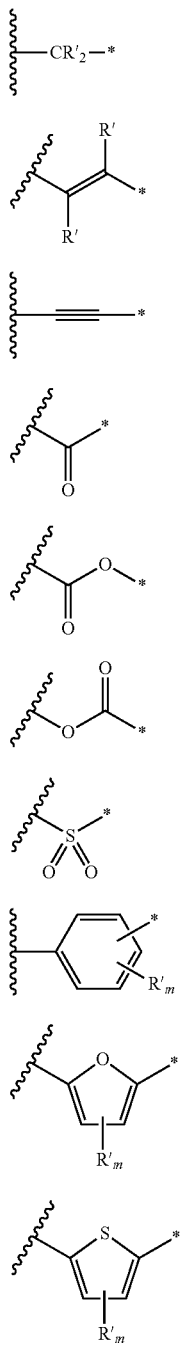

wherein in the formulae (L-1) to (L-10), the wavy line represents a position bonded to any one of a naphthalene ring, a ring containing $A^1$ and a ring containing $A^2$; and * represents a position bonded to $R^b$ or $R^c$; in the formula (L-8), m represents 4; in the formulae (L-9) and (L-10), m represents 2; in the formulae (L-1), (L-2), (L-8), (L-9) and (L-10), R' each independently represents a hydrogen atom or a substituent, provided that, in the formulae (L-1) and (L-2), R' each independently may form a condensed ring with R bonded to L.

[5] In the organic thin film transistor according to any one of the items [1] to [4], in the formula (1), $R^3$ to $R^6$ each independently represent a hydrogen atom, a fluorine atom, a substituted or unsubstituted alkyl group having from 1 to 3 carbon atoms, a substituted or unsubstituted alkynyl group having from 2 to 3 carbon atoms, a substituted or unsubstituted alkenyl group having from 2 to 3 carbon atoms, a substituted or unsubstituted alkoxy group having from 1 to 2 carbon atoms, or a substituted or unsubstituted methylthio group.

[6] In the organic thin film transistor according to any one of the items [3] to [5], in the formula (2) or (3), all of $L^a$, $L^b$ and $L^c$ each preferably represent a divalent linking group represented by any one of the formulae (L-1) to (L-3), (L-8), (L-9) or (L-10).

[7] In the organic thin film transistor according to any one of the items [3] to [6], in the formula (2) or (3), all of $L^a$, $L^b$ and $L^c$ each preferably represent a divalent linking group represented by any one of the formula (L-1) or (L-8).

[8] In the organic thin film transistor according to any one of the items [3] to [7], in the formula (2) or (3), all of $R^a$, $R^b$ and $R^c$ each preferably represent a substituted or unsubstituted alkyl group.

[9] In the organic thin film transistor according to any one of the items [3] to [8], in the formula (2) or (3), all of $R^a$, $R^b$ and $R^c$ each preferably represent a linear alkyl group.

[10] In the organic thin film transistor according to the item [1] or [2], the compound represented by the formula (1) is preferably a compound represented by the following formula (4):

Formula (4)

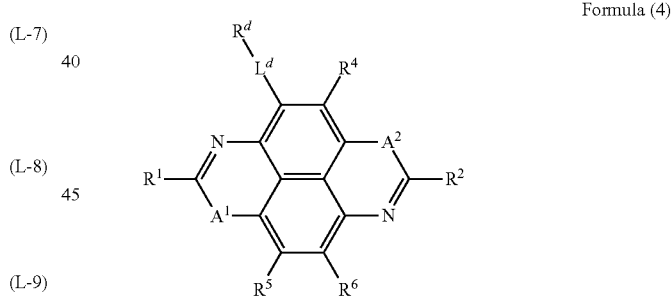

wherein in the formula (4), $A^1$ and $A^2$ each independently represent a sulfur atom, an oxygen atom or a selenium atom; $R^1$ and $R^2$ each independently represent a hydrogen atom or an aryl group, and $R^4$ to $R^6$ each independently represent a hydrogen atom or a substituent; $L^d$ represents a divalent linking group represented by any one of the following formulae (L-1) to (L-10), or a divalent linking group consisting of 2 or more divalent linking groups each represented by any one of the following formulae (L-1) to (L-10) in which the 2 or more divalent linking groups are bonded sequentially; and $R^d$ represents a hydrogen atom, a substituted or unsubstituted alkyl group, an oligooxyethylene group having a repeating number of an oxyethylene unit of 2 or more, an oligosiloxane group having 2 or more silicon atoms, or a substituted or unsubstituted trialkylsilyl group, provided that $R^d$ represents a hydrogen atom only when $L^d$ is represented by any one of the formulae (L-1) to (L-3) and (L-8) to (L-10), and $R^d$ represents a substituted or unsubstituted trialkylsilyl group only when $L^d$ bonded to $R^d$ is a divalent linking group represented by the following formula (L-3);

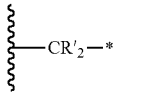 (L-1)

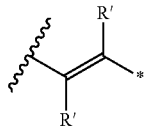 (L-2)

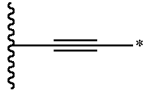 (L-3)

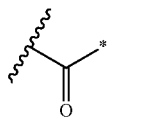 (L-4)

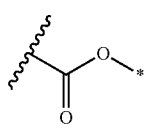 (L-5)

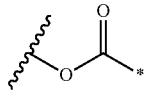 (L-6)

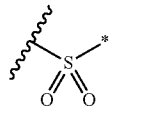 (L-7)

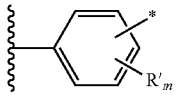 (L-8)

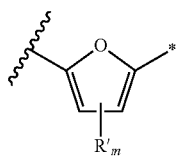 (L-9)

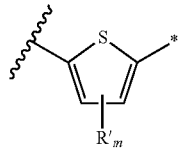 (L-10)

wherein in the formulae (L-1) to (L-10), the wavy line represents a position bonded to a naphthalene ring; and * represents a position bonded to $R^d$; in the formula (L-8), m represents 4; in the formulae (L-9) and (L-10), m represents 2; in the formulae (L-1), (L-2), (L-8), (L-9) and (L-10), R' each independently represents a hydrogen atom or a substituent, provided that, in the formulae (L-1) and (L-2), R' each independently may form a condensed ring with R bonded to L.

[11] In the organic thin film transistor according to any one of the items [1], [2] and [10], the compound represented by the formula (1) is preferably a compound represented by the following formula (5):

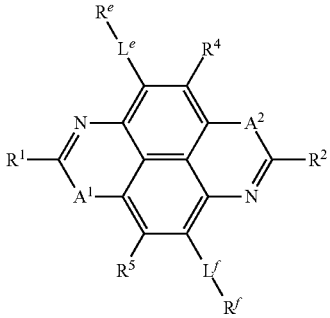

Formula (5)

wherein in the formula (5), $A^1$ and $A^2$ each independently represent a sulfur atom, an oxygen atom or a selenium atom; $R^4$ and $R^2$ each independently represent a hydrogen atom or an aryl group, and $R^4$ and $R^5$ each independently represent a hydrogen atom or a substituent; $L^e$ and $L^f$ each independently represent a divalent linking group represented by any one of the following formulae (L-1) to (L-10), or a divalent linking group consisting of 2 or more divalent linking groups each represented by any one of the following formulae (L-1) to (L-10) in which the 2 or more divalent linking groups are bonded sequentially; and $R^e$ and $R^f$ each independently represent a hydrogen atom, a substituted or unsubstituted alkyl group, an oligooxyethylene group having a repeating number of an oxyethylene unit of 2 or more, an oligosiloxane group having 2 or more silicon atoms, or a substituted or unsubstituted trialkylsilyl group, provided that $R^e$ and $R^f$ represent a hydrogen atom only when $L^e$ and $L^f$ are represented by any one of the formulae (L-1) to (L-3) and (L-8) to (L-10), and $R^e$ and $R^f$ represent a substituted or unsubstituted trialkylsilyl group only when $L^e$ and $L^f$ each bonded to $R^e$ and $R^f$ are a divalent linking group represented by the following formula (L-3);

 (L-1)

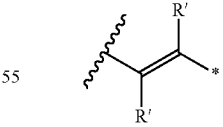 (L-2)

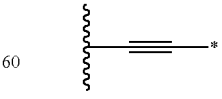 (L-3)

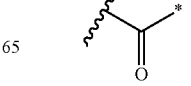 (L-4)

-continued

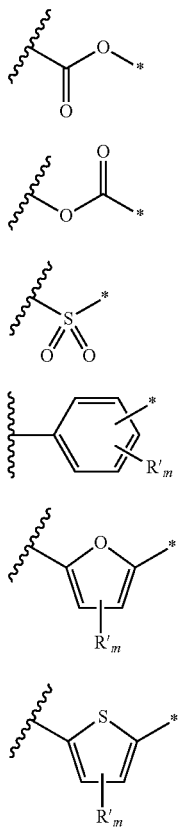

(L-5)

(L-6)

(L-7)

(L-8)

(L-9)

(L-10)

wherein in the formulae (L-1) to (L-10), the wavy line represents a position bonded to a naphthalene ring; and * represents a position bonded to $R^e$ or $R^f$; in the formula (L-8), m represents 4; in the formulae (L-9) and (L-10), m represents 2; in the formulae (L-1), (L-2), (L-8), (L-9) and (L-10), R' each independently represents a hydrogen atom or a substituent, provided that, in the formulae (L-1) and (L-2), R' each independently may form a condensed ring with R bonded to L.

[12] A compound represented by the following formula (1):

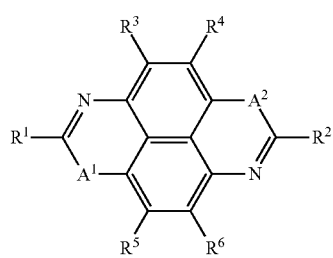

Formula (1)

wherein in the formula (1), $A^1$ and $A^2$ each independently represent a sulfur atom, an oxygen atom or a selenium atom; and $R^1$ to $R^6$ each independently represent a hydrogen atom or a substituent, provided that at least one of $R^1$ to $R^6$ represents a substituent represented by the following formula (W):

*-L-R    Formula (W)

wherein in the formula (W), * represents a position bonded to a naphthalene ring in the formula (1), or bonded to a ring containing $A^1$ or a ring containing $A^2$; L represents a divalent linking group represented by any one of the following formulae (L-1) to (L-10), or a divalent linking group consisting of 2 or more divalent linking groups each represented by any one of the following formulae (L-1) to (L-10) in which the 2 or more divalent linking groups are bonded sequentially; and R represents a hydrogen atom, a substituted or unsubstituted alkyl group, an oligooxyethylene group having a repeating number of an oxyethylene unit of 2 or more, an oligosiloxane group having 2 or more silicon atoms, or a substituted or unsubstituted trialkylsilyl group, provided that R represents a hydrogen atom only when L is represented by any one of the formulae (L-1) to (L-3) and (L-8) to (L-10), and R represents a substituted or unsubstituted trialkylsilyl group only when L bonded to R is a divalent linking group represented by the following formula (L-3);

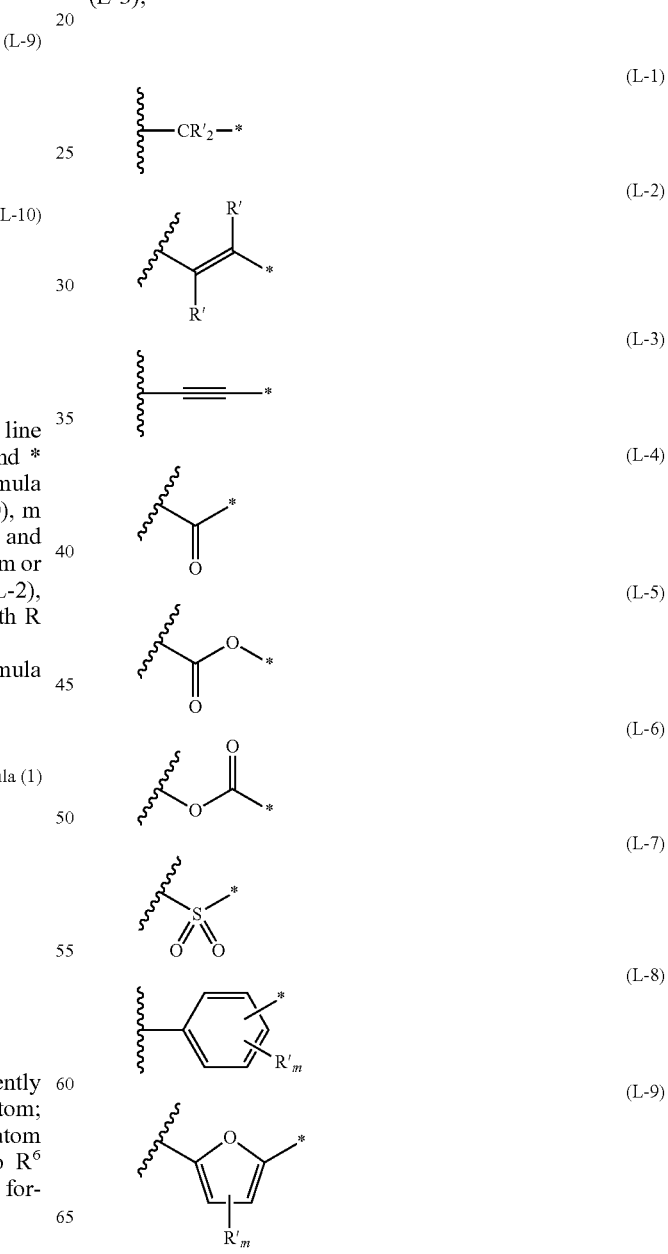

(L-1)

(L-2)

(L-3)

(L-4)

(L-5)

(L-6)

(L-7)

(L-8)

(L-9)

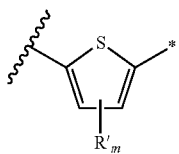
(L-10)

wherein in the formulae (L-1) to (L-10), the wavy line represents a position bonded to any one of a naphthalene ring, a ring containing $A^1$ and a ring containing $A^2$; and * represents a position bonded to R in the formula (W); in the formula (L-8), m represents 4; in the formulae (L-9) and (L-10), m represents 2; in the formulae (L-1), (L-2), (L-8), (L-9) and (L-10), R' each independently represents a hydrogen atom or a substituent, provided that, in the formulae (L-1) and (L-2), R' each independently may form a condensed ring with R bonded to L.

[13] In the compound according to the item [12], at least one of $R^1$ and $R^2$ in the formula (1) preferably represents a substituent represented by the formula (W).

[14] In the compound according to the item [12] or [13], the compound represented by the formula (1) is preferably a compound represented by the following formula (2):

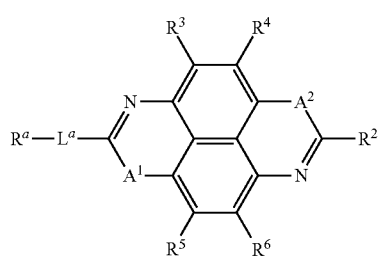

Formula (2)

wherein in the formula (2), $A^1$ and $A^2$ each independently represent a sulfur atom, an oxygen atom or a selenium atom; $R^2$ to $R^6$ each independently represent a hydrogen atom or a substituent; $L^a$ represents a divalent linking group represented by any one of the following formulae (L-1) to (L-10), or a divalent linking group consisting of 2 or more divalent linking groups each represented by any one of the following formulae (L-1) to (L-10) in which the 2 or more divalent linking groups are bonded sequentially; and $R^a$ represents a hydrogen atom, a substituted or unsubstituted alkyl group, an oligooxyethylene group having a repeating number of an oxyethylene unit of 2 or more, an oligosiloxane group having 2 or more silicon atoms, or a substituted or unsubstituted trialkylsilyl group, provided that $R^a$ represents a hydrogen atom only when $L^a$ is represented by any one of the formulae (L-1) to (L-3) and (L-8) to (L-10), and $R^a$ represents a substituted or unsubstituted trialkylsilyl group only when $L^a$ bonded to $R^a$ is a divalent linking group represented by the following formula (L-3);

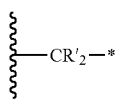
(L-1)

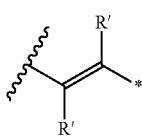
(L-2)

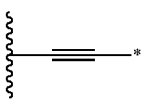
(L-3)

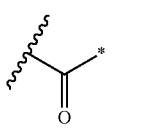
(L-4)

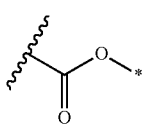
(L-5)

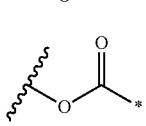
(L-6)

(L-7)

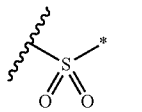
(L-8)

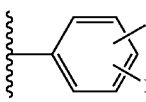
(L-9)

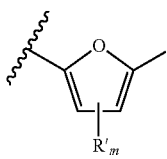
(L-10)

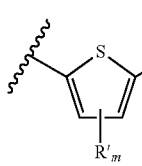

wherein in the formulae (L-1) to (L-10), the wavy line represents a position bonded to any one of a naphthalene ring, a ring containing $A^1$ and a ring containing $A^2$; and * represents a position bonded to $R^a$; in the formula (L-8), m represents 4; in the formulae (L-9) and (L-10), m represents 2; in the formulae (L-1), (L-2), (L-8), (L-9) and (L-10), R' each independently represents a hydrogen atom or a substituent, provided that, in the formulae (L-1) and (L-2), R' each independently may form a condensed ring with R bonded to L.

[15] In the compound according to the any one of items [12] to [14], the compound represented by the formula (1) is preferably a compound represented by the following formula (3):

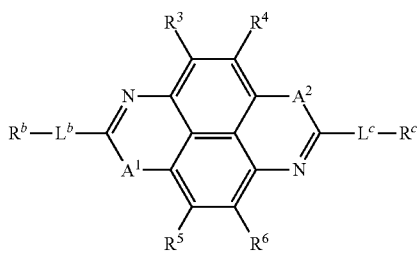

Formula (3)

wherein in the formula (3), $A^1$ and $A^2$ each independently represent a sulfur atom, an oxygen atom or a selenium atom; $R^3$ to $R^6$ each independently represent a hydrogen atom or a substituent; $L^b$ and $L^c$ each independently represent a divalent linking group represented by any one of the following formulae (L-1) to (L-10), or a divalent linking group consisting of 2 or more divalent linking groups each represented by any one of the following formulae (L-1) to (L-10) in which the 2 or more divalent linking groups are bonded sequentially; and $R^b$ and $R^c$ each independently represent a hydrogen atom, a substituted or unsubstituted alkyl group, an oligooxyethylene group having a repeating number of an oxyethylene unit of 2 or more, an oligosiloxane group having 2 or more silicon atoms, or a substituted or unsubstituted trialkylsilyl group, provided that $R^b$ and $R^c$ represent a hydrogen atom only when $L^b$ and $L^c$ are represented by any one of the formulae (L-1) to (L-3) and (L-8) to (L-10), and $R^b$ and $R^c$ represent a substituted or unsubstituted trialkylsilyl group only when $L^b$ and $L^c$ each bonded to $R^b$ and $R^c$ are a divalent linking group represented by the following formula (L-3);

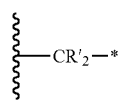 (L-1)

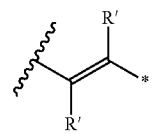 (L-2)

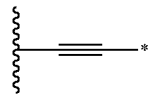 (L-3)

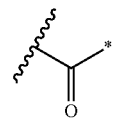 (L-4)

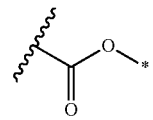 (L-5)

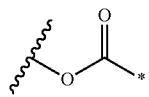 (L-6)

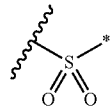 (L-7)

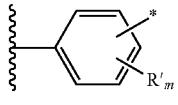 (L-8)

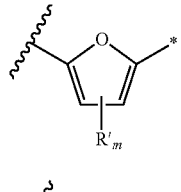 (L-9)

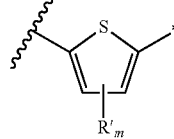 (L-10)

wherein in the formulae (L-1) to (L-10), the wavy line represents a position bonded to any one of a naphthalene ring, a ring containing $A^1$ and a ring containing $A^2$; and * represents a position bonded to $R^b$ or $R^c$; in the formula (L-8), m represents 4; in the formulae (L-9) and (L-10), m represents 2; in the formulae (L-1), (L-2), (L-8), (L-9) and (L-10), R' each independently represents a hydrogen atom or a substituent, provided that, in the formulae (L-1) and (L-2), R' each independently may form a condensed ring with R bonded to L.

[16] In the compound according to any one of the items [12] to [15], in the formula (1), $R^3$ to $R^6$ each independently represent a hydrogen atom, a fluorine atom, a substituted or unsubstituted alkyl group having from 1 to 3 carbon atoms, a substituted or unsubstituted alkynyl group having from 2 to 3 carbon atoms, a substituted or unsubstituted alkenyl group having from 2 to 3 carbon atoms, a substituted or unsubstituted alkoxy group having from 1 to 2 carbon atoms, or a substituted or unsubstituted methylthio group.

[17] In the compound according to any one of the items [14] to [16], in the formula (2) or (3), all of $L^a$, $L^b$ and $L^c$ each preferably represent a divalent linking group represented by anyone of the formulae (L-1) to (L-3), (L-8), (L-9) or (L-10).

[18] In the compound according to any one of the items [14] to [17], in the formula (2) or (3), all of $L^a$, $L^b$ and $L^c$ each preferably represent a divalent linking group represented by any one of the formula (L-1) or (L-8).

[19] In the compound according to any one of the items [14] to [18], in the formula (2) or (3), all of $R^a$, $R^b$ and $R^c$ each preferably represent a substituted or unsubstituted alkyl group.

[20] In the compound according to any one of the items [14] to [19], in the formula (2) or (3), all of $R^a$, $R^b$ and $R^c$ each preferably represent a linear alkyl group.

[21] In the compound according to the item [12] or [13], the compound represented by the formula (1) is preferably a compound represented by the following formula (4):

Formula (4)

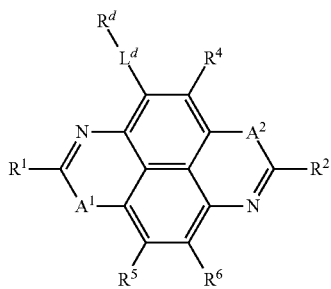

wherein in the formula (4), $A^1$ and $A^2$ each independently represent a sulfur atom, an oxygen atom or a selenium atom; $R^1$ and $R^2$ each independently represent a hydrogen atom or an aryl group, and $R^4$ to $R^6$ each independently represent a hydrogen atom or a substituent; $L^d$ represents a divalent linking group represented by any one of the following formulae (L-1) to (L-10), or a divalent linking group consisting of 2 or more divalent linking groups each represented by any one of the following formulae (L-1) to (L-10) in which the 2 or more divalent linking groups are bonded sequentially; and $R^d$ represents a hydrogen atom, a substituted or unsubstituted alkyl group, an oligooxyethylene group having a repeating number of an oxyethylene unit of 2 or more, an oligosiloxane group having 2 or more silicon atoms, or a substituted or unsubstituted trialkylsilyl group, provided that $R^d$ represents a hydrogen atom only when $L^d$ is represented by any one of the formulae (L-1) to (L-3) and (L-8) to (L-10), and $R^d$ represents a substituted or unsubstituted trialkylsilyl group only when $L^d$ bonded to $R^d$ is a divalent linking group represented by the following formula (L-3);

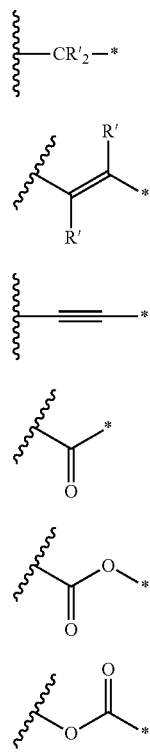

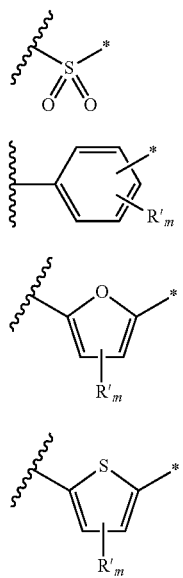

wherein in the formulae (L-1) to (L-10), the wavy line represents a position bonded to a naphthalene ring; and * represents a position bonded to $R^d$; in the formula (L-8), m represents 4; in the formulae (L-9) and (L-10), m represents 2; in the formulae (L-1), (L-2), (L-8), (L-9) and (L-10), R' each independently represents a hydrogen atom or a substituent, provided that, in the formulae (L-1) and (L-2), R' each independently may form a condensed ring with R bonded to L.

[22] In the compound according to any one of the items [12], [13] and [21], the compound represented by the formula (1) is preferably a compound represented by the following formula (5):

Formula (5)

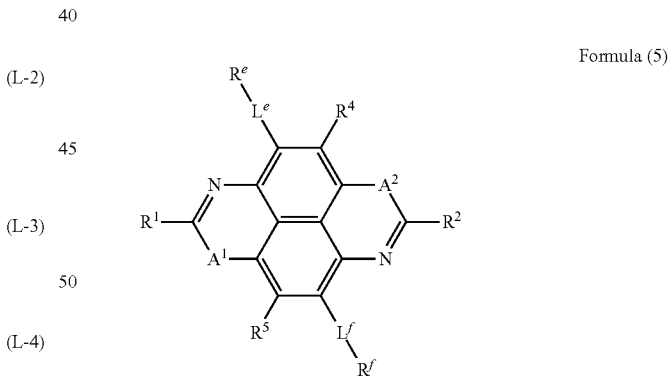

wherein in the formula (5), $A^1$ and $A^2$ each independently represent a sulfur atom, an oxygen atom or a selenium atom; $R^1$ and $R^2$ each independently represent a hydrogen atom or an aryl group, and $R^4$ and $R^5$ each independently represent a hydrogen atom or a substituent; $L^e$ and $L^f$ each independently represent a divalent linking group represented by any one of the following formulae (L-1) to (L-10), or a divalent linking group consisting of 2 or more divalent linking groups each represented by any one of the following formulae (L-1) to (L-10) in which the 2 or more divalent linking groups are bonded sequentially; and $R^e$ and $R^f$ each independently represent a hydrogen atom, a substituted or unsubstituted alkyl group, an oligooxyethylene group having a repeating number of an oxyethylene unit of 2 or more, an oligosiloxane group having 2 or more silicon atoms, or a substituted or unsubstituted trialkylsilyl group, provided that $R^e$ and $R^f$ represent a hydrogen atom only when $L^e$ and $L^f$ are represented by any one of the formulae (L-1) to (L-3) and (L-8) to (L-10), and $R^e$ and $R^f$ represent a substituted or unsubstituted trialkylsilyl group only when $L^e$ and $L^f$ each bonded to $R^e$ and $R^f$ are a divalent linking group represented by the following formula (L-3);

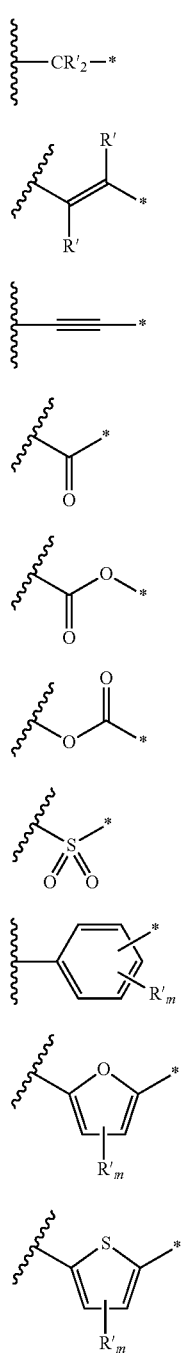

wherein in the formulae (L-1) to (L-10), the wavy line represents a position bonded to a naphthalene ring; and represents a position bonded to $R^e$ or $R^f$; in the formula (L-8), m represents 4; in the formulae (L-9) and (L-10), m represents 2; in the formulae (L-1), (L-2), (L-8), (L-9) and (L-10), R' each independently represents a hydrogen atom or a substituent, provided that, in the formulae (L-1) and (L-2), R' each independently may form a condensed ring with R bonded to L.

[23] An organic semiconductor material for a non-light emitting organic semiconductor device, containing the compound according to any one of the items [12] to [22].

[24] A material for an organic thin film transistor, containing the compound according to any one of the items [12] to [22].

[25] A coating solution for a non-light emitting organic semiconductor device, containing the compound according to any one of the items [12] to [22].

[26] A coating solution for a non-light emitting organic semiconductor device, containing the compound according to any one of the items [12] to [22], and a polymer binder.

[27] An organic semiconductor thin film for a non-light emitting organic semiconductor device, containing the compound according to any one of the items [12] to [22].

[28] An organic semiconductor thin film for a non-light emitting organic semiconductor device, containing the compound according to any one of the items [12] to [22], and a polymer binder.

[29] The organic semiconductor thin film for a non-light emitting organic semiconductor device according to the item [27] or [28] is preferably produced by a solution coating method.

According to the invention, an organic thin film transistor may be provided that has a high carrier mobility, a small change in the threshold voltage after repeated driving and a high solubility in an organic solvent.

Figure 1:
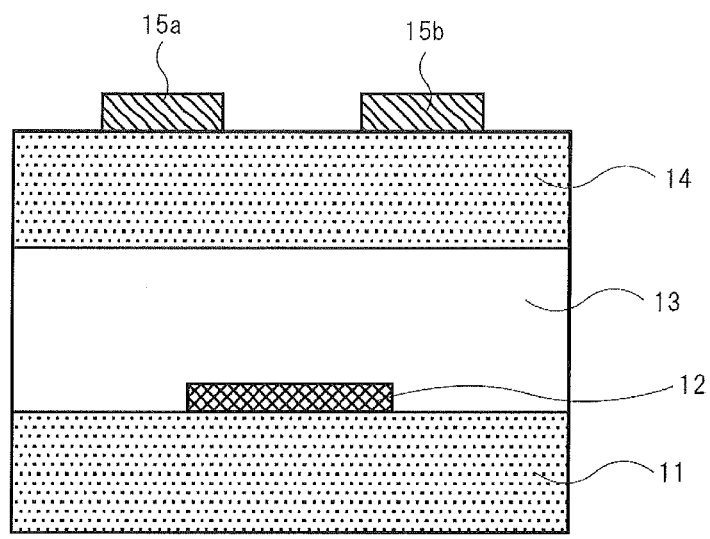
FIG. 1 is a schematic illustration showing a cross sectional structure of one example of the organic thin film transistor of the invention.

In the drawings, 11 is substrate, 12 is electrode, 13 is insulating layer, 14 is semiconductor active layer (organic material layer or organic semiconductor layer), 15a, 15b are electrode, 31 is substrate, 32 is electrode, 33 is insulating layer, 34a, 34b are electrode, and 35 is semiconductor active layer (organic material layer or organic semiconductor layer).

DESCRIPTION OF EMBODIMENTS

The invention will be described in detail below. The description for the constitutional components shown below may be made with reference to representative embodiments and specific examples, but the invention is not limited to the embodiments and the examples. In the description, a numerical range expressed with reference to an upper limit and/or a lower limit means a range that includes the upper limit and/or the lower limit.

In the invention, the hydrogen atom that is referred without any particular discrimination in the description of the formulae herein includes isotopes thereof (such as a deuterium atom). The atoms constituting the substituents also include isotopes thereof.

[Organic Thin Film Transistor]

The organic thin film transistor of the invention contains a compound represented by the following formula (1) in a semiconductor active layer:

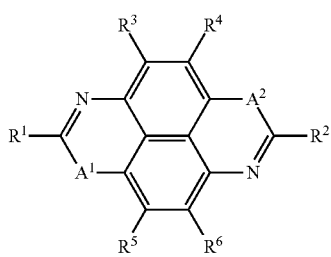

Formula (1)

wherein in the formula (1), $A^1$ and $A^2$ each independently represent a sulfur atom, an oxygen atom or a selenium atom; and $R^1$ to $R^6$ each independently represent a hydrogen atom or a substituent, provided that at least one of $R^1$ to $R^6$ represents a substituent represented by the following formula (W):

*-L-R  Formula (W)

wherein in the formula (W), * represents a position bonded to a naphthalene ring in the formula (1), or bonded to a ring containing $A^1$ or a ring containing $A^2$; L represents a divalent linking group represented by any one of the following formulae (L-1) to (L-10), or a divalent linking group consisting of 2 or more divalent linking groups each represented by any one of the following formulae (L-1) to (L-10) in which the 2 or more divalent linking groups are bonded sequentially; and R represents a hydrogen atom, a substituted or unsubstituted alkyl group, an oligooxyethylene group having a repeating number of an oxyethylene unit of 2 or more, an oligosiloxane group having 2 or more silicon atoms, or a substituted or unsubstituted trialkylsilyl group, provided that R represents a hydrogen atom only when L is represented by any one of the formulae (L-1) to (L-3) and (L-8) to (L-10), and R represents a substituted or unsubstituted trialkylsilyl group only when L bonded to R is a divalent linking group represented by the following formula (L-3);

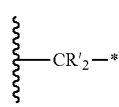

(L-1)

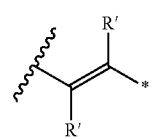

(L-2)

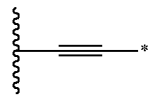

(L-3)

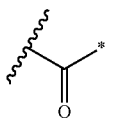

(L-4)

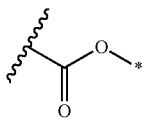

(L-5)

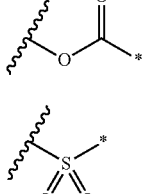

(L-6)

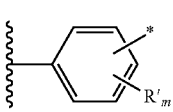

(L-7)

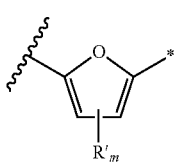

(L-8)

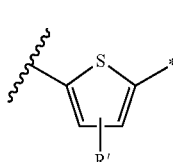

(L-9)

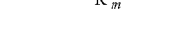

(L-10)

wherein in the formulae (L-1) to (L-10), the wavy line represents a position bonded to any one of a naphthalene ring, a ring containing $A^1$ and a ring containing $A^2$; and * represents a position bonded to R in the formula (W); in the formula (L-8), m represents 4; in the formulae (L-9) and (L-10), m represents 2; in the formulae (L-1), (L-2), (L-8), (L-9) and (L-10), R' each independently represents a hydrogen atom or a substituent, provided that, in the formulae (L-1) and (L-2), R' each independently may form a condensed ring with R bonded to L.

According to the constitution, the organic thin film transistor of the invention has a high carrier mobility and a small change in the threshold voltage after repeated driving.

The compound represented by the formula (1) has a substituent represented by the formula (W) as at least one of $R^1$ to $R^6$, and thus is preferred from the standpoint of the applicability of the material to a solution process and the molecular orientation in the film. According to the structure, the production efficiency of the organic thin film that is applicable to an organic thin film transistor may be increased to suppress the production cost. Furthermore, the carrier transport property including the carrier mobility, and the chemical stability and the physical stability of the thin film may also be enhanced. Accordingly, an organic thin film transistor having a high carrier mobility may be obtained.

For reducing the change in the threshold voltage after repeated driving, there are such requirements as chemical stability of the organic semiconductor material (particularly, air oxidation resistance and redox stability), thermal stability in the form of a thin film, a large film density capable of preventing air and water from invading, a film quality with less defects capable of preventing charges from being accumulated, and the like. It is considered that the compound represented by the formula (1) satisfies these requirements and thus has a small change in the threshold voltage after repeated driving. Accordingly, the organic thin film transistor of the invention having a less change in the threshold voltage after repeated driving has a semiconductor active layer that has a high chemical stability, a high film density, and the like, and thus effectively functions as a transistor for a prolonged period of time.

Patent Document 1, Non-patent Document 1 and Patent Document 2 fail to describe a compound the same as the compound represented by the formula (1). The compounds described in those literatures have a low carrier mobility. In the invention, on the other hand, the advantageous effects of the invention may be obtained by using, as an organic semiconductor material, the compound that has a skeleton represented by the formula (1) and has at least one substituent represented by the formula (W).

Preferred embodiments of the compound of the invention, the organic thin film transistor of the invention, and the like will be described below.

<Compound Represented by Formula (1)>

The compound of the invention is represented by the following formula (1). The compound of the invention is contained in a semiconductor active layer described later in the organic thin film transistor of the invention. Thus, the compound of the invention may be used as a material for an organic thin film transistor.

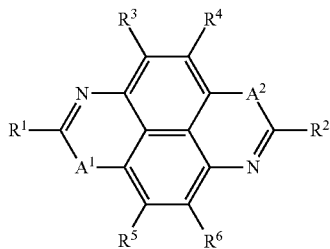

Formula (1)

wherein in the formula (1), $A^1$ and $A^2$ each independently represent a sulfur atom, an oxygen atom or a selenium atom; and $R^1$ to $R^6$ each independently represent a hydrogen atom or a substituent, provided that at least one of $R^1$ to $R^6$ represents a substituent represented by the following formula (W):

*-L-R                    Formula (W)

wherein in the formula (W), * represents a position bonded to a naphthalene ring in the formula (1), or bonded to a ring containing $A^1$ or a ring containing $A^2$; L represents a divalent linking group represented by any one of the following formulae (L-1) to (L-10), or a divalent linking group consisting of 2 or more divalent linking groups each represented by any one of the following formulae (L-1) to (L-10) in which the 2 or more divalent linking groups are bonded sequentially; and R represents a hydrogen atom, a substituted or unsubstituted alkyl group, an oligooxyethylene group having a repeating number of an oxyethylene unit of 2 or more, an oligosiloxane group having 2 or more silicon atoms, or a substituted or unsubstituted trialkylsilyl group, provided that R represents a hydrogen atom only when L is represented by any one of the formulae (L-1) to (L-3) and (L-8) to (L-10), and R represents a substituted or unsubstituted trialkylsilyl group only when L bonded to R is a divalent linking group represented by the following formula (L-3);

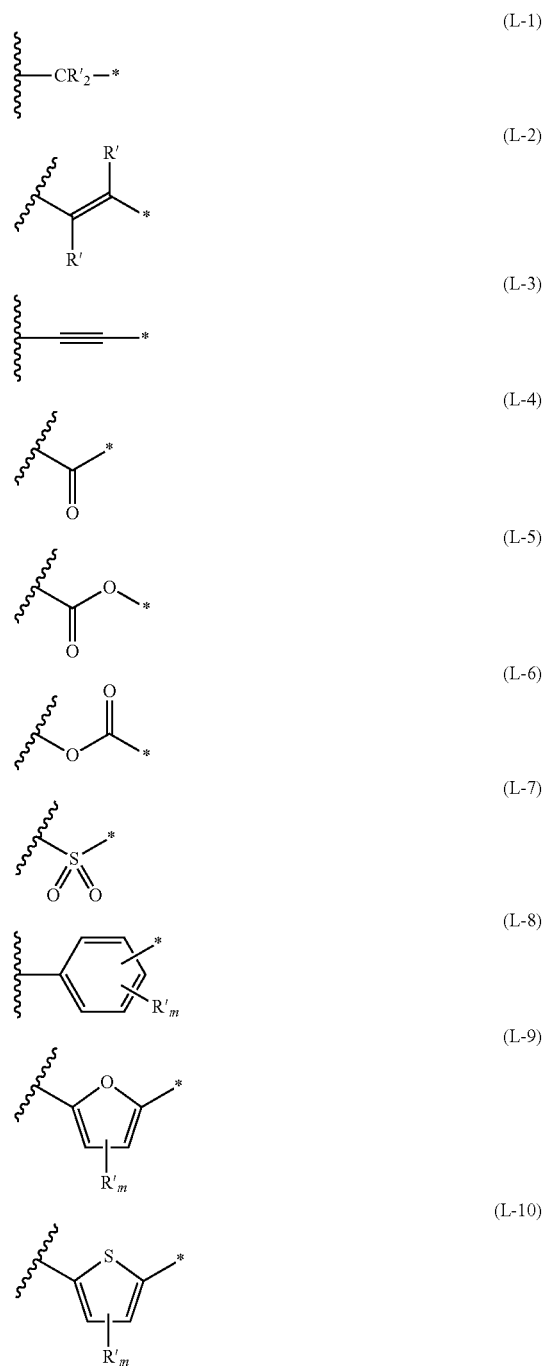

wherein in the formulae (L-1) to (L-10), the wavy line represents a position bonded to any one of a naphthalene ring, a ring containing $A^1$ and a ring containing $A^2$; and * represents a position bonded to R in the formula (W); in the formula (L-8), m represents 4; in the formulae (L-9) and (L-10), m represents 2; in the formulae (L-1), (L-2), (L-8), (L-9) and (L-10), R' each independently represents a hydrogen atom or a substituent, provided that, in the formulae (L-1) and (L-2), R' each independently may form a condensed ring with R bonded to L.

In the formula (1), $A^1$ and $A^2$ each independently represent a sulfur atom, an oxygen atom or a selenium atom. $A^1$ and $A^2$ preferably represents a sulfur atom or and oxygen atom. $A^1$ and $A^2$ may be the same or different, but preferably the same.

In the formula (1), $R^1$ to $R^6$ each independently represent a hydrogen atom or a substituent, provided that at least one of $R^1$ to $R^6$ represents a substituent represented by the formula (W).

The compound represented by the formula (1) may contain a substituent other than the substituent represented by the formula (W).

Examples of the substituent that may be $R^1$ to $R^6$ in the formula (1) include a halogen atom, an alkyl group (including a cycloalkyl group, a bicycloalkyl group and a tricycloalkyl group), an alkenyl group (including a cycloalkenyl group and a bicycloalkenyl group), an alkynyl group, an aryl group, a heterocyclic group, a cyano group, a hydroxyl group, a nitro group, a carboxyl group, an alkoxy group, an aryloxy group, a silyloxy group, a heterocyclic oxy group, an acyloxy group, a carbamoyloxy group, an alkoxycarbonyloxy group, an aryloxycarbonyloxy group, an amino group (including an anilino group), an ammonio group, an acylamino group, an aminocarbonylamino group, an alkoxycarbonylamino group, an aryloxycarbonylamino group, a sulfamoylamino group, an alkyl- or arylsulfonylamino group, a mercapto group, an alkylthio group, an arylthio group, a heterocyclic thio group, a sulfamoyl group, a sulfo group, an alkyl- or arylsulfinyl group, an alkyl- or arylsulfonyl group, an acyl group, an aryloxycarbonyl group, an alkoxycarbonyl group, a carbamoyl group, an aryl- or heterocyclic azo group, an imide group, a phosphino group, a phosphinyl group, a phosphinyloxy group, a phosphinylamino group, a phosphono group, a silyl group, a hydrazino group, a ureido group, a boronic acid group ($—B(OH)_2$), a phosphato group ($—PO(OH)_2$), a sulphato group ($—OSO_3H$), and other known groups.

Among these, a halogen atom, an alkyl group and an aryl group are preferred. A fluorine atom, an alkyl group having from 1 to 3 carbon atoms, an alkynyl group having from 2 to 3 carbon atoms, an alkenyl group having from 2 to 3 carbon atoms, an alkoxy group having from 1 to 2 carbon atoms, a methylthio group, a phenyl group, an 1-naphthyl group and a 2-naphthyl group are more preferred. A fluorine atom, a substituted or unsubstituted alkyl group having from 1 to 3 carbon atoms, a substituted or unsubstituted alkynyl group having from 2 to 3 carbon atoms, a substituted or unsubstituted alkenyl group having from 2 to 3 carbon atoms, a substituted or unsubstituted alkoxy group having from 1 to 2 carbon atoms, a substituted or unsubstituted methylthio group are particularly preferred.

In the compound represented by the formula (1), the number of the substituent other than the substituent represented by the formula (W) in $R^4$ to $R^6$ is preferably from 0 to 4, more preferably from 0 to 2, particularly preferably 0 in the case where both $R^3$ and $R^6$ are not the substituent represented by the formula (W), and further particularly preferably 0 or 2 in the case where at least one of $R^3$ and $R^6$ is the substituent represented by the formula (W).

These substituents may further have the substituents stated above.

In the case where the either $R^3$ or $R^6$ is not the substituent represented by the formula (W), it is preferred that $R^3$ to $R^6$ each independently represent a hydrogen atom, a fluorine atom, a substituted or unsubstituted alkyl group having from 1 to 3 carbon atoms, a substituted or unsubstituted alkynyl group having from 2 to 3 carbon atoms, a substituted or unsubstituted alkenyl group having from 2 to 3 carbon atoms, a substituted or unsubstituted alkoxy group having from 1 to 2 carbon atoms, or a substituted or unsubstituted methylthio group. In the case where the at least one of $R^3$ and $R^6$ is the substituent represented by the formula (W), it is preferred that $R^4$ and $R^5$ each independently represent a hydrogen atom, a fluorine atom, a substituted or unsubstituted alkyl group having from 1 to 3 carbon atoms, an alkynyl group having from 2 to 3 carbon atoms, an alkenyl group having from 2 to 3 carbon atoms, an alkoxy group having from 1 to 2 carbon atoms, or a substituted or unsubstituted methylthio group; and that $R^4$ and $R^2$ each independently represent a hydrogen atom or an aryl group (preferably a phenyl group, an 1-naphthyl group or a 2-naphthyl group).

The substituent represented by the formula (W) will be described.

In the formula (W), L represents a divalent linking group represented by any one of the following formulae (L-1) to (L-10), or a divalent linking group consisting of 2 or more divalent linking groups each represented by any one of the following formulae (L-1) to (L-10) in which the 2 or more divalent linking groups are bonded sequentially.

(L-1)

(L-2)

(L-3)

(L-4)

(L-5)

(L-6)

(L-7)

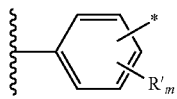
(L-8)

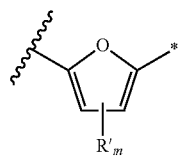
(L-9)

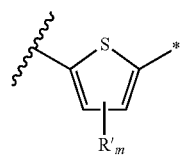
(L-10)

In the formulae (L-1) to (L-10), the wavy line represents a position bonded to any one of a naphthalene ring, a ring containing $A^1$ and a ring containing $A^2$; and * represents a position bonded to R in the formula (W); in the formula (L-8), m represents 4; in the formulae (L-9) and (L-10), m represents 2; in the formulae (L-1), (L-2), (L-8), (L-9) and (L-10), R' each independently represents a hydrogen atom or a substituent, provided that, in the formulae (L-1) and (L-2), R' each independently may form a condensed ring with R bonded to L.

In the case where L represents a divalent linking group containing divalent linking groups each represented by any one of the formulae (L-1) to (L-10) in which the divalent linking groups are bonded sequentially, the number of the divalent linking groups each represented by any one of the formulae (L-1) to (L-10) in which the divalent linking groups are bonded sequentially is preferably from 2 to 4, and more preferably 2 or 3.

Particularly in the formulae (L-8) to (L-10), it is also preferred that anyone of the formulae (L-1) to (L-10) is further inserted between * and R to form L that represents a linking group containing divalent linking groups each represented by any one of the formulae (L-1) to (L-10) in which the divalent linking groups are bonded sequentially.

Examples of the substituent R' in the formulae (L-1), (L-2), (L-8), (L-9) and (L-10) include the groups that are shown as examples of the other substituent that may be $R^1$ to $R^6$ in the formula (1).

In the formula (L-8), m represents 4; and in the formulae (L-9) and (L-10), m represents 2.

L preferably represents a divalent linking group represented by any one of the formulae (L-1) to (L-2), (L-5) to (L-8), (L-9) and (L-10), or a divalent linking group consisting of 2 or more of the divalent linking groups bonded sequentially, more preferably a divalent linking group represented by any one of the formulae (L-1) to (L-3), (L-8), (L-9) and (L-10) or a divalent linking group consisting of 2 or more of the divalent linking groups bonded sequentially from the standpoint of the chemical stability and the carrier transport property, particularly preferably a divalent linking group represented by the formula (L-1) or (L-8).

In the formula (W), R represents a hydrogen atom, a substituted or unsubstituted alkyl group, an oligooxyethylene group having a repeating number of an oxyethylene unit of 2 or more, an oligosiloxane group having 2 or more silicon atoms, or substituted or unsubstituted trialkylsilyl group.

In the case where R in the formula (W) represents a substituted or unsubstituted alkyl group, the number of carbon atoms thereof is preferably from 2 to 18, more preferably from 3 to 12 from the standpoint of the chemical stability and the carrier transport property, and further preferably from 4 to 10.

In the compound represented by the formula (1), in the case where the group represented by the formula (W) contains an alkyl group, a high carrier mobility may be obtained when the alkyl group represented by R has a carbon number that is the lower limit of the aforementioned range or more. In the case where L contains the formula (L-1) bonded to R, a high carrier mobility may be obtained when the alkyl group formed by bonding the alkylene group represented by the formula (L-1) and the alkyl group represented by R has a carbon number that is the lower limit of the aforementioned range or more.

The alkyl group that may be R may be any one of linear, branched and cyclic, and is preferably a linear alkyl group from the standpoint of the enhancement of the carrier mobility, particularly in the case where either $R^3$ or $R^6$ is not a substituent represented by the formula (W), preferably a linear alkyl group having from 1 to 12 carbon atoms, more preferably a linear alkyl group having from 3 to 12 carbon atoms, and particularly preferably a linear alkyl group having from 4 to 10 carbon atoms. In the case where R represents an alkyl group having a substituent, examples of the substituent include a halogen atom, and a fluorine atom is preferred. In the case where R represents an alkyl group having a fluorine atom, the alkyl group may be a perfluoroalkyl group, in which all the hydrogen atoms of the alkyl group are replaced by fluorine atoms. Meanwhile, in the case where at least one of $R^3$ and $R^6$ is the substituent represented by the formula (W), the alkyl group is preferably a branched alkyl group from the standpoint of the enhancement of the solubility, more preferably a branched alkyl group having from 3 to 12 carbon atoms, and particularly preferably a branched alkyl group having 4 to 10 carbon atoms.

In the case where R in the formula (W) represents an oligooxyethylene group having a repeating number of an oxyethylene group of 2 or more, the oxyethylene group represented by R herein means a group represented by —$(CH_2CH_2)_xOY$ (wherein the repeating number of an oxyethylene unit x is an integer of 2 or more, and Y as the terminal group represents a hydrogen atom or a substituent). In the case where Y as the terminal group of the oligooxyethylene group is a hydrogen atom, the group is a hydroxyl group. The repeating number of an oxyethylene unit x is preferably from 2 to 4, and more preferably from 2 to 3. The terminal hydroxyl group of the oligooxyethylene group is preferably blocked, i.e., Y preferably represents a substituent. In this case, the hydroxyl group is preferably blocked with an alkyl group having from 1 to 3 carbon atoms, i.e., Y preferably represents an alkyl group having from 1 to 3 carbon atoms, and Y more preferably represents a methyl group or an ethyl group, and particularly preferably a methyl group.

In the case where R in the formula (W) represents an oligosiloxane group having 2 or more silicon atoms, the repeating number of a siloxane unit is preferably from 2 to 4, and more preferably from 2 to 3. The Si atom is preferably bonded to a hydrogen atom or an alkyl group. In the case where the Si atom is bonded to an alkyl group, the number of carbon atoms of the alkyl group is preferably from 1 to 3, and for example, a methyl group or an ethyl group is preferably bonded thereto. The Si atom may be bonded to the same alkyl groups or may be bonded to different alkyl groups or a hydrogen atom. The siloxane units constituting the oligosiloxane group may be all the same as each other or different from each other, and are preferably all the same as each other.

Only in the case where L bonded to R is a divalent linking group represented by the formula (L-3), R may represent a substituted or unsubstituted trialkylsilyl group. In the case where R represents a substituted or unsubstituted trialkylsilyl group, the number of carbon atoms of the alkyl group bonded to the Si atom is preferably from 1 to 3, and for example, a methyl group, an ethyl group or an isopropyl group is preferably bonded thereto. The Si atom may be bonded to the same alkyl groups or may be bonded to different alkyl groups or a hydrogen atom. In the case where the R represents a trialkylsilyl group having a substituent, the substituent is not particularly limited.

In the compound represented by the formula (1), the number of the substituent that is represented by the formula (W) in $R^1$ to $R^6$ is preferably from 1 to 4 in the case where either $R^3$ or $R^6$ is not a substituent represented by the formula (W), more preferably from 1 to 2, and particularly preferably 2. In the compound represented by the formula (1), the number of the substituent that is represented by the formula (W) in $R^1$ to $R^6$ is preferably from 1 to 4 in the case where at least one of $R^3$ and $R^6$ is a substituent represented by the formula (W), and more preferably from 2 to 4.

In the formula (1) in the invention, at least one of $R^1$ and $R^2$ preferably represents a substituent represented by the formula (W). Especially in the case where either $R^3$ or $R^6$ is not a substituent represented by the formula (W), at least one of $R^1$ and $R^2$ preferably represents a substituent represented by the formula (W).

It is considered that the reason why these positions are preferred as the substitution positions in the formula (1) is that the compound is excellent in chemical stability and is preferred from the standpoint of the HOMO level and the molecular packing in the film. In particular, in the formula (1), when two positions of $R^1$ and $R^2$ each represent a substituent, a high carrier concentration may be obtained.

Moreover, in the formula (1), it is preferred that $R^3$ and $R^6$ each independently represent a hydrogen atom, a fluorine atom, a substituted or unsubstituted alkyl group having from 1 to 3 carbon atoms, a substituted or unsubstituted alkynyl group having from 2 to 3 carbon atoms, a substituted or unsubstituted alkenyl group having from 2 to 3 carbon atoms, a substituted or unsubstituted alkoxy group having from 1 to 2 carbon atoms, or a substituted or unsubstituted methylthio group in the case where the either $R^3$ or $R^6$ is not the substituent represented by the formula (W).

Meanwhile, it is also preferred that at least one of $R^3$ and $R^6$ is a substituent represented by the formula (W), and more preferred that at least one of $R^3$ and $R^6$ is a substituent represented by the formula (W) while $R^1$ and $R^2$ each independently represent a hydrogen atom or an aryl group (preferably a phenyl group, an 1-naphthyl group or a 2-naphthyl group). It is considered that the reason why these positions are preferred as the substitution positions in the formula (1) is that the compound is excellent in chemical stability and is preferred from the standpoint of the HOMO level and the molecular packing in the film. In the case where at least one of $R^3$ and $R^6$ is a substituent represented by the formula (W), $R^4$ and $R^5$ each independently represent a hydrogen atom, a fluorine atom, a substituted or unsubstituted alkyl group having from 1 to 3 carbon atoms, a substituted or unsubstituted alkynyl group having from 2 to 3 carbon atoms, a substituted or unsubstituted alkenyl group having from 2 to 3 carbon atoms, a substituted or unsubstituted alkoxy group having from 1 to 2 carbon atoms, or a substituted or unsubstituted methylthio group.

In the invention, the compound represented by the formula (1) is preferably a compound represented by the following formula (2).

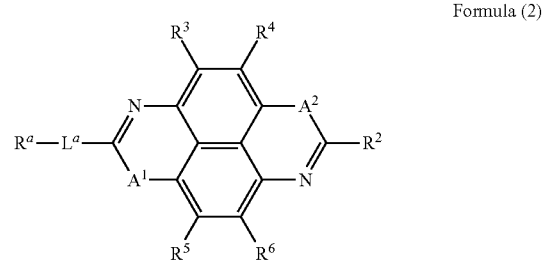

Formula (2)

wherein in the formula (2), $A^1$ and $A^2$ each independently represent a sulfur atom, an oxygen atom or a selenium atom; $R^2$ to $R^6$ each independently represent a hydrogen atom or a substituent; $L^a$ represents a divalent linking group represented by any one of the following formulae (L-1) to (L-10), or a divalent linking group consisting of 2 or more divalent linking groups each represented by any one of the following formulae (L-1) to (L-10) in which the 2 or more divalent linking groups are bonded sequentially; and $R^a$ represents a hydrogen atom, a substituted or unsubstituted alkyl group, an oligooxyethylene group having a repeating number of an oxyethylene unit of 2 or more, an oligosiloxane group having 2 or more silicon atoms, or a substituted or unsubstituted trialkylsilyl group, provided that $R^a$ represents a hydrogen atom only when $L^a$ is represented by any one of the formulae (L-1) to (L-3) and (L-8) to (L-10), and $R^a$ represents a substituted or unsubstituted trialkylsilyl group only when $L^a$ bonded to $R^a$ is a divalent linking group represented by the following formula (L-3);

(L-1)

(L-2)

(L-3)

(L-4)

(L-5)

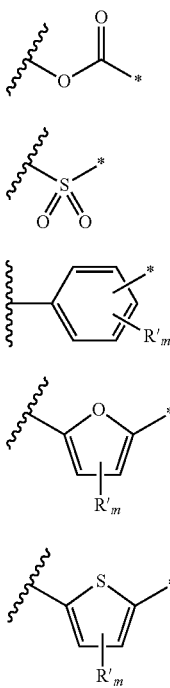

(L-6)

(L-7)

(L-8)

(L-9)

(L-10)

wherein in the formulae (L-1) to (L-10), the wavy line represents a position bonded to any one of a naphthalene ring, a ring containing $A^1$ and a ring containing $A^2$; and * represents a position bonded to $R^a$; in the formula (L-8), m represents 4; in the formulae (L-9) and (L-10), m represents 2; in the formulae (L-1), (L-2), (L-8), (L-9) and (L-10), R' each independently represents a hydrogen atom or a substituent, provided that, in the formulae (L-1) and (L-2), R' each independently may form a condensed ring with R bonded to L.

In the formula (2), $A^1$ and $A^2$ each independently represent a sulfur atom, an oxygen atom or a selenium atom, which have the same meanings and the same preferred ranges of $A^1$ and $A^2$ in the formula (1).

In the formula (2), $R^2$ to $R^6$ each independently represent a hydrogen atom or a substituent. The preferred ranges of the substituents represented by $R^2$ to $R^6$ are the same as the preferred ranges of the substituents represented by $R^1$ to $R^6$ in the formula (1) other than the substituent represented by the formula (W). In the formula (2), $R^2$ preferably represents the substituent represented by the formula (W).

In the formula (2), $L^a$ represents a divalent linking group represented by any one of the formulae (L-1) to (L-10), or a divalent linking group consisting of 2 or more divalent linking groups each represented by any one of the formulae (L-1) to (L-10) in which the 2 or more divalent linking groups are bonded sequentially. The preferred ranges of $L^a$ are the same as the preferred ranges of L in the formula (W).

In the formula (2), $R^a$ represents a hydrogen atom, a substituted or unsubstituted alkyl group, an oligooxyethylene group having a repeating number of an oxyethylene unit of 2 or more, an oligosiloxane group having 2 or more silicon atoms, or a substituted or unsubstituted trialkylsilyl group, provided that $R^a$ represents a hydrogen atom only when $L^a$ is represented by any one of the formulae (L-1) to (L-3) and (L-8) to (L-10), and $R^a$ represents a substituted or unsubstituted trialkylsilyl group only when $L^a$ bonded to $R^a$ is a divalent linking group represented by the following formula (L-3). The preferred ranges of $R^a$ are the same as the preferred ranges of R in the formula (W).

In the invention, the compound represented by the formula (1) is preferably a compound represented by the following formula (3).

Formula (3)

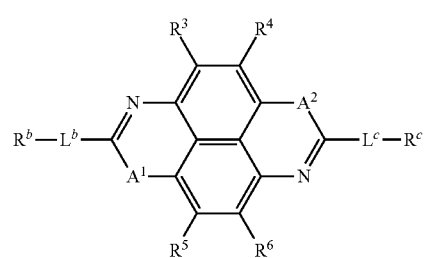

wherein in the formula (3), $A^1$ and $A^2$ each independently represent a sulfur atom, an oxygen atom or a selenium atom; $R^3$ to $R^6$ each independently represent a hydrogen atom or a substituent; $L^b$ and $L^c$ each independently represent a divalent linking group represented by any one of the following formulae (L-1) to (L-10), or a divalent linking group consisting of 2 or more divalent linking groups each represented by any one of the following formulae (L-1) to (L-10) in which the 2 or more divalent linking groups are bonded sequentially; and $R^b$ and $R^c$ each independently represent a hydrogen atom, a substituted or unsubstituted alkyl group, an oligooxyethylene group having a repeating number of an oxyethylene unit of 2 or more, an oligosiloxane group having 2 or more silicon atoms, or a substituted or unsubstituted trialkylsilyl group, provided that $R^b$ and $R^c$ represent a hydrogen atom only when $L^b$ and $L^c$ are represented by any one of the formulae (L-1) to (L-3) and (L-8) to (L-10), and $R^b$ and $R^c$ represent a substituted or unsubstituted trialkylsilyl group only when $L^b$ and $L^c$ each bonded to $R^b$ and $R^c$ are a divalent linking group represented by the following formula (L-3);

(L-1)

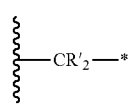

(L-2)

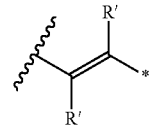

(L-3)

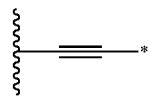

(L-4)

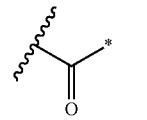

(L-5)

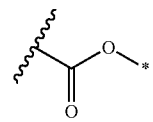

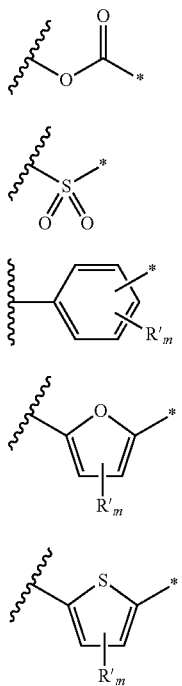

wherein in the formulae (L-1) to (L-10), the wavy line represents a position bonded to any one of a naphthalene ring, a ring containing $A^1$ and a ring containing $A^2$; and * represents a position bonded to $R^b$ or $R^c$; in the formula (L-8), m represents 4; in the formulae (L-9) and (L-10), m represents 2; in the formulae (L-1), (L-2), (L-8), (L-9) and (L-10), R' each independently represents a hydrogen atom or a substituent, provided that, in the formulae (L-1) and (L-2), R' each independently may form a condensed ring with R bonded to L.

In the formula (3), $A^1$ and $A^2$ each independently represent a sulfur atom, an oxygen atom or a selenium atom, which have the same meanings and the same preferred ranges of $A^1$ and $A^2$ in the formula (1).

In the formula (3), $R^3$ to $R^6$ each independently represent a hydrogen atom or a substituent. The preferred ranges of the substituents represented by $R^3$ to $R^6$ are the same as the preferred ranges of the substituents represented by $R^1$ to $R^6$ in the formula (1) other than the substituent represented by the formula (W).

In the formula (3), $L^b$ and $L^c$ each independently represent a divalent linking group represented by any one of the formulae (L-1) to (L-10), or a divalent linking group consisting of 2 or more divalent linking groups each represented by any one of the formulae (L-1) to (L-10) in which the 2 or more divalent linking groups are bonded sequentially. The preferred ranges of $L^b$ and $L^c$ are the same as the preferred ranges of L in the formula (W). $L^b$ and $L^c$ are preferably the same as each other.

In the formula (3), $R^b$ and $R^c$ each independently represent a hydrogen atom, a substituted or unsubstituted alkyl group, an oligooxyethylene group having a repeating number of an oxyethylene unit of 2 or more, an oligosiloxane group having 2 or more silicon atoms, or a substituted or unsubstituted trialkylsilyl group, provided that $R^b$ and $R^c$ represent a hydrogen atom only when $L^b$ and $L^c$ are represented by any one of the formulae (L-1) to (L-3) and (L-8) to (L-10), and $R^b$ and $R^c$ represent a substituted or unsubstituted trialkylsilyl group only when $L^b$ and $L^c$ each bonded to $R^b$ and $R^c$ are a divalent linking group represented by the following formula (L-3). The preferred ranges of $R^b$ and $R^c$ are the same as the preferred ranges of R in the formula (W). $R^b$ and $R^c$ are preferably the same as each other.

In the formulae (2) and (3), all of $R^a$, $R^b$ and $R^c$ each preferably represent a substituted or unsubstituted alkyl group, more preferably a substituted or unsubstituted linear alkyl group, further preferably a linear alkyl group having from 1 to 12 carbon atoms, still further preferably a linear alkyl group having from 3 to 12 carbon atoms, and particularly preferably a linear alkyl group having from 4 to 10 carbon atoms.

In the formulae (2) and (3), all of $L^a$, $L^b$ and $L^c$ each preferably represent a group represented by any one of the formulae (L-1) to (L-3), (L-8), (L-9) and (L-10), more preferably any one of the formulae (L-1) to (L-3), (L-8) and (L-10) from the standpoint of the chemical stability and the carrier transport property, and particularly preferably any one of the formula (L-1) or (L-8).

In the invention, the compound represented by the formula (1) is preferably a compound represented by the following formula (4).

Formula (4)

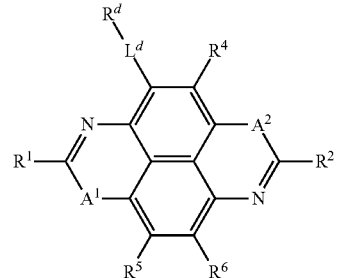

wherein in the formula (4), $A^1$ and $A^2$ each independently represent a sulfur atom, an oxygen atom or a selenium atom; $R^4$ and $R^2$ each independently represent a hydrogen atom or an aryl group, and $R^4$ to $R^6$ each independently represent a hydrogen atom or a substituent; $L^d$ represents a divalent linking group represented by any one of the following formulae (L-1) to (L-10), or a divalent linking group consisting of 2 or more divalent linking groups each represented by any one of the following formulae (L-1) to (L-10) in which the 2 or more divalent linking groups are bonded sequentially; and $R^d$ represents a hydrogen atom, a substituted or unsubstituted alkyl group, an oligooxyethylene group having a repeating number of an oxyethylene unit of 2 or more, an oligosiloxane group having 2 or more silicon atoms, or a substituted or unsubstituted trialkylsilyl group, provided that $R^d$ represents a hydrogen atom only when $L^d$ is represented by any one of the formulae (L-1) to (L-3) and (L-8) to (L-10), and $R^d$ represents a substituted or unsubstituted trialkylsilyl group only when $L^d$ bonded to $R^d$ is a divalent linking group represented by the following formula (L-3);

(L-1)

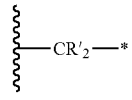

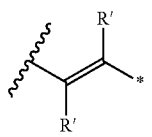
(L-2)

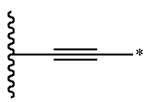
(L-3)

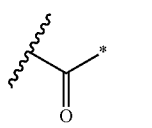
(L-4)

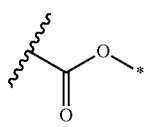
(L-5)

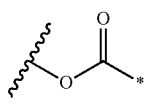
(L-6)

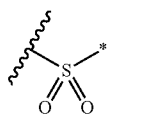
(L-7)

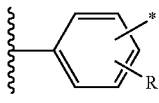
(L-8)

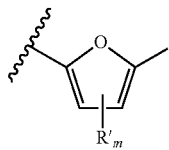
(L-9)

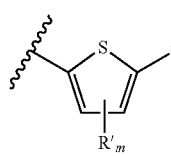
(L-10)

wherein in the formulae (L-1) to (L-10), the wavy line represents a position bonded to a naphthalene ring; and * represents a position bonded to $R^d$; in the formula (L-8), m represents 4; in the formulae (L-9) and (L-10), m represents 2; in the formulae (L-1), (L-2), (L-8), (L-9) and (L-10), R' each independently represents a hydrogen atom or a substituent, provided that, in the formulae (L-1) and (L-2), R' each independently may form a condensed ring with R bonded to L.

In the formula (4), $A^1$ and $A^2$ each independently represent a sulfur atom, an oxygen atom or a selenium atom, which have the same meanings and the same preferred ranges of $A^1$ and $A^2$ in the formula (1).

In the formula (4), $R^1$, $R^2$ and $R^4$ to $R^6$ each independently represent a hydrogen atom or a substituent. The preferred ranges of the substituents represented by $R^1$, $R^2$ and $R^4$ to $R^6$ are the same as the preferred ranges of the substituents represented by $R^4$, $R^2$ and $R^4$ to $R^6$ in the case where at least one of $R^3$ and $R^6$ is the substituent represented by the formula (W). In the formula (4), $R^6$ preferably represents the substituent represented by the formula (W).

In the formula (4), $L^d$ represents a divalent linking group represented by any one of the formulae (L-1) to (L-10), or a divalent linking group consisting of 2 or more divalent linking groups each represented by any one of the formulae (L-1) to (L-10) in which the 2 or more divalent linking groups are bonded sequentially. The preferred ranges of $L^d$ are the same as the preferred ranges of L in the formula (W).

In the formula (4), $R^d$ represents a hydrogen atom, a substituted or unsubstituted alkyl group, an oligooxyethylene group having a repeating number of an oxyethylene unit of 2 or more, an oligosiloxane group having 2 or more silicon atoms, or a substituted or unsubstituted trialkylsilyl group, provided that $R^d$ represents a hydrogen atom only when $L^d$ is represented by any one of the formulae (L-1) to (L-3) and (L-8) to (L-10), and $R^d$ represents a substituted or unsubstituted trialkylsilyl group only when $L^d$ bonded to $R^d$ is a divalent linking group represented by the following formula (L-3). The preferred ranges of $R^d$ are the same as the preferred ranges of R in the formula (W).

In the invention, the compound represented by the formula (1) is preferably a compound represented by the following formula (5).

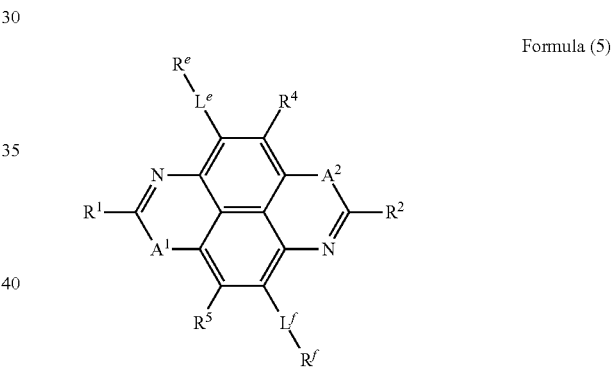

Formula (5)

wherein in the formula (5), $A^1$ and $A^2$ each independently represent a sulfur atom, an oxygen atom or a selenium atom; $R^4$ and $R^2$ each independently represent a hydrogen atom or an aryl group, and $R^4$ and $R^5$ each independently represent a hydrogen atom or a substituent; $L^e$ and $L^f$ each independently represent a divalent linking group represented by any one of the following formulae (L-1) to (L-10), or a divalent linking group consisting of 2 or more divalent linking groups each represented by any one of the following formulae (L-1) to (L-10) in which the 2 or more divalent linking groups are bonded sequentially; and $R^e$ and $R^f$ each independently represent a hydrogen atom, a substituted or unsubstituted alkyl group, an oligooxyethylene group having a repeating number of an oxyethylene unit of 2 or more, an oligosiloxane group having 2 or more silicon atoms, or a substituted or unsubstituted trialkylsilyl group, provided that $R^e$ and $R^f$ represent a hydrogen atom only when $L^e$ and $L^f$ are represented by any one of the formulae (L-1) to (L-3) and (L-8) to (L-10), and $R^e$ and $R^f$ represent a substituted or unsubstituted trialkylsilyl group only when $L^e$ and $L^f$ each bonded to $R^e$ and $R^f$ are a divalent linking group represented by the following formula (L-3);

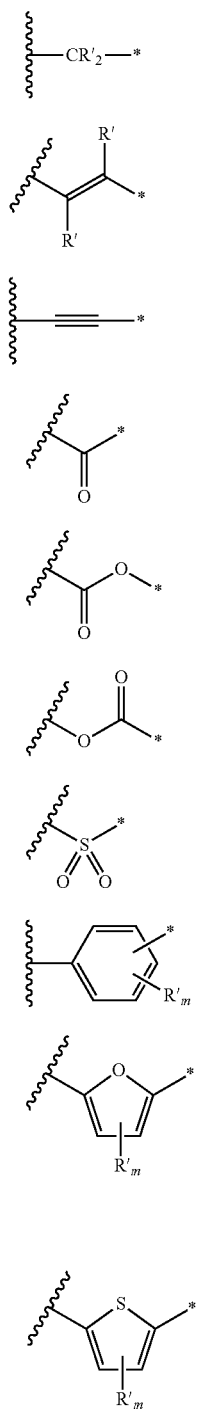

wherein in the formulae (L-1) to (L-10), the wavy line represents a position bonded to a naphthalene ring; and * represents a position bonded to $R^e$ or $R^f$; in the formula (L-8), m represents 4; in the formulae (L-9) and (L-10), m represents 2; in the formulae (L-1), (L-2), (L-8), (L-9) and (L-10), R' each independently represents a hydrogen atom or a substituent, provided that, in the formulae (L-1) and (L-2), R' each independently may form a condensed ring with R bonded to L.

In the formula (5), $A^1$ and $A^2$ each independently represent a sulfur atom, an oxygen atom or a selenium atom, which have the same meanings and the same preferred ranges of $A^1$ and $A^2$ in the formula (1).

In the formula (5), $R^1$, $R^2$, $R^4$ and $R^5$ each independently represent a hydrogen atom or a substituent. The preferred ranges of the substituents represented by $R^1$, $R^2$, $R^4$ and $R^5$ are the same as the preferred ranges of the substituents represented by $R^1$, $R^2$, $R^4$ and $R^5$ in the case where at least one of $R^3$ and $R^6$ in the formula (1) is the substituent represented by the formula (W).

In the formula (5), $L^e$ and $L^f$ each independently represent a divalent linking group represented by any one of the formulae (L-1) to (L-10), or a divalent linking group consisting of 2 or more divalent linking groups each represented by any one of the formulae (L-1) to (L-10) in which the 2 or more divalent linking groups are bonded sequentially. The preferred ranges of $L^e$ and $L^f$ are the same as the preferred ranges of L in the formula (W). $L^e$ and $L^f$ are preferably the same as each other.

In the formula (5), $R^e$ and $R^f$ each independently represent a hydrogen atom, a substituted or unsubstituted alkyl group, an oligooxyethylene group having a repeating number of an oxyethylene unit of 2 or more, an oligosiloxane group having 2 or more silicon atoms, or a substituted or unsubstituted trialkylsilyl group, provided that $R^e$ and $R^f$ represent a hydrogen atom only when $L^e$ and $L^f$ are represented by any one of the formulae (L-1) to (L-3) and (L-8) to (L-10), and $R^e$ and $R^f$ represent a substituted or unsubstituted trialkylsilyl group only when $L^e$ and $L^f$ each bonded to $R^e$ and $R^f$ are a divalent linking group represented by the following formula (L-3). The preferred ranges of $R^e$ and $R^f$ are the same as the preferred ranges of R in the formula (W). $R^e$ and $R^f$ are preferably the same as each other.

In the formulae (4) and (5), all of $R^d$, $R^e$ and $R^f$ each preferably represent a substituted or unsubstituted alkyl group or an oligosiloxane group having 2 or more silicon atoms, more preferably a substituted or unsubstituted branched alkyl group or an oligosiloxane group having 2 or more silicon atoms, particularly preferably a branched alkyl group having from 3 to 12 carbon atoms or an oligosiloxane group having from 2 to 4 silicon atoms, and further particularly preferably a branched alkyl group having from 4 to 10.

In the formulae (4) and (5), all of $L^d$, $L^e$ and $L^f$ each preferably represent a group represented by any one of the formulae (L-1) to (L-3), (L-8), (L-9) and (L-10), more preferably any one of the formulae (L-1) to (L-3), (L-8) and (L-10) from the standpoint of the chemical stability and the carrier transport property, and particularly preferably any one of the formula (L-1) or (L-8).

Specific examples of the compound represented by the formula (1) are shown below, but the compound represented by the formula (1) capable of being used in the invention is not construed as being limited to the specific examples.

| Compound 1 | Compound 2 |
|---|---|
| Compound 3 | Compound 4 |
| Compound 5 | Compound 6 |
| Compound 7 | Compound 8 |
| Compound 9 | Compound 10 |
| Compound 11 | Compound 12 |
| Compound 13 | Compound 14 |
| Compound 15 | Compound 16 |
| Compound 17 | Compound 18 |

-continued
Compound 19
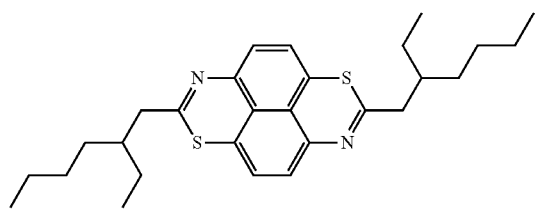
Compound 20
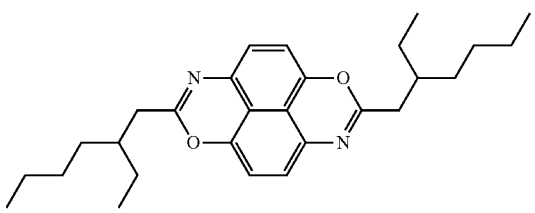
Compound 21
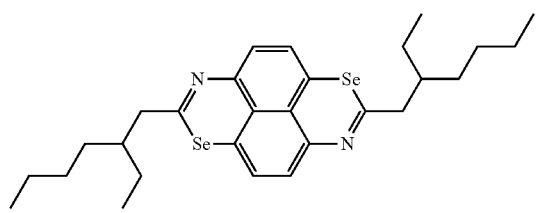
Compound 22
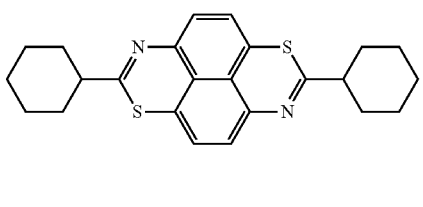
Compound 23
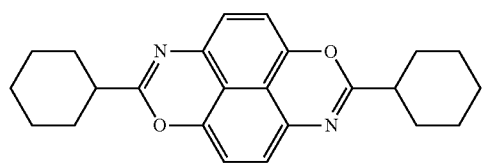
Compound 24
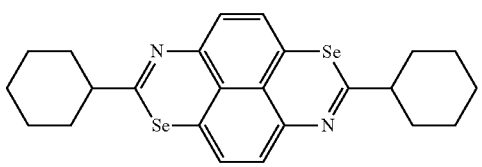
Compound 25
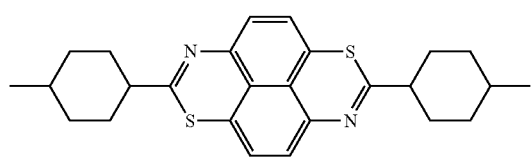
Compound 26
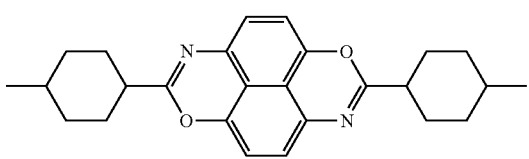
Compound 27
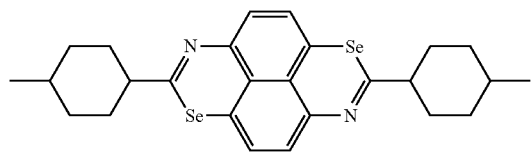
Compound 28
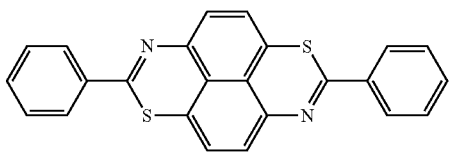
Compound 29
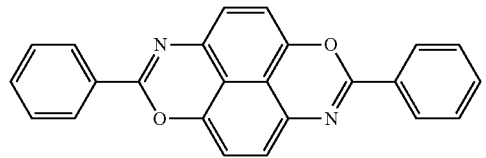
Compound 30
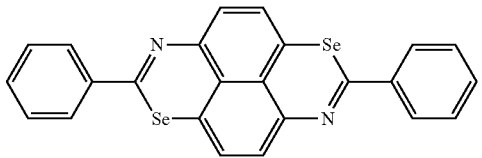
Compound 31
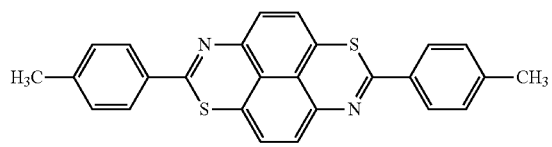
Compound 32
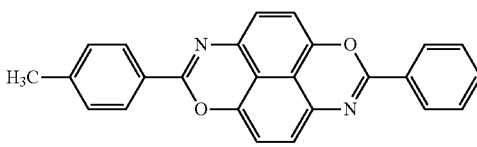
Compound 33
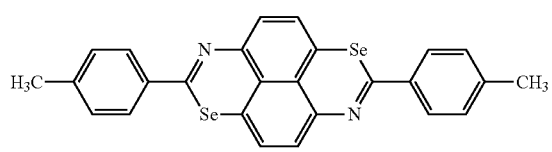
Compound 34
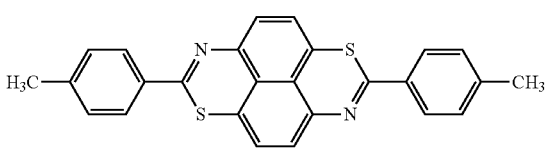

-continued
Compound 35
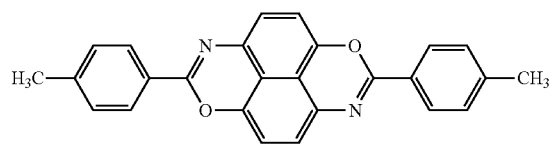
Compound 36
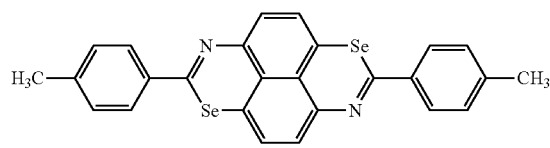
Compound 37
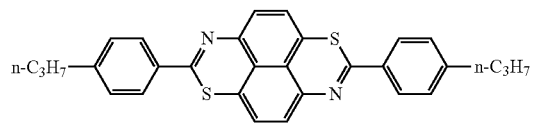
Compound 38
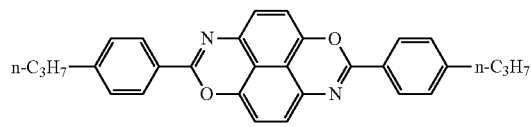
Compound 39
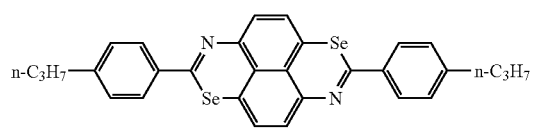
Compound 40
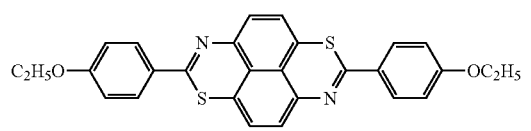
Compound 41
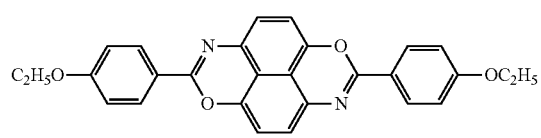
Compound 42
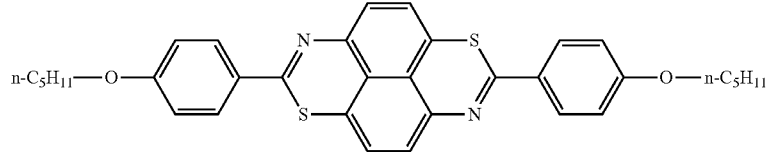
Compound 43
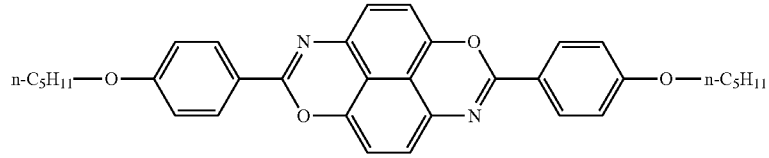
Compound 44
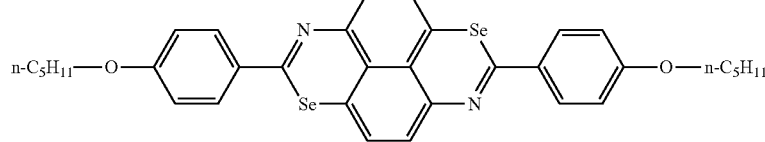
Compound 45
Compound 46
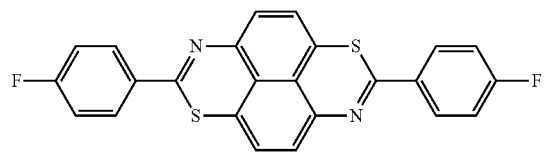
Compound 47
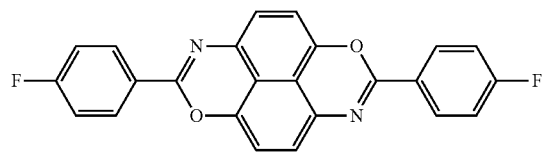
Compound 48
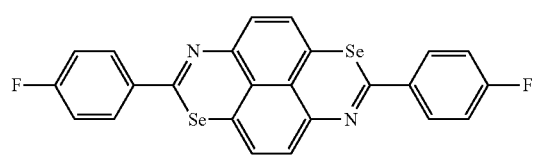
Compound 49
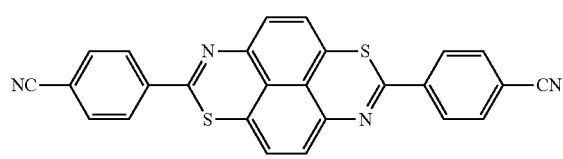

-continued
Compound 50
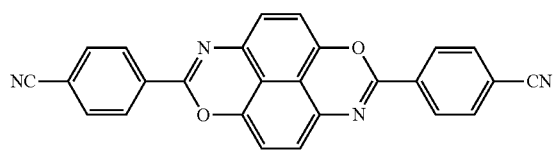
Compound 51
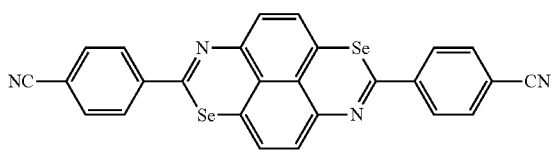
Compound 52
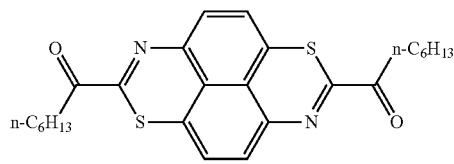
Compound 53
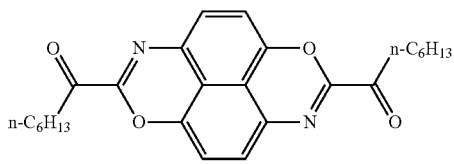
Compound 54
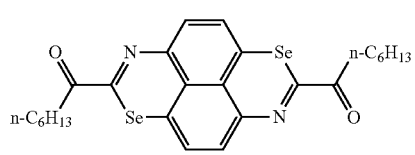
Compound 55
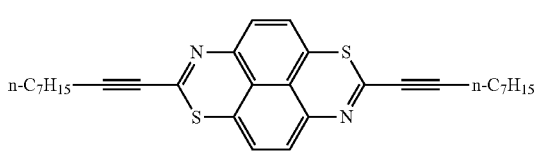
Compound 56
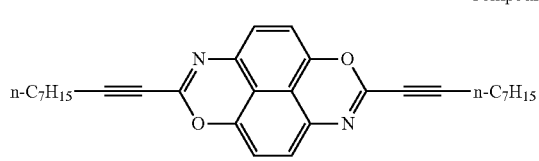
Compound 57
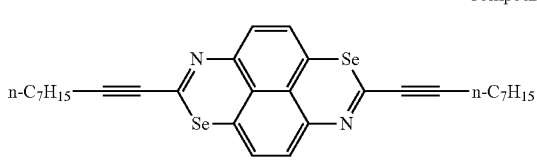
Compound 58
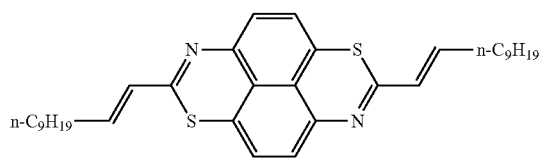
Compound 59
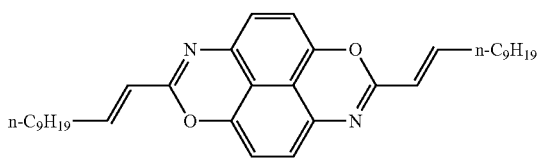
Compound 60
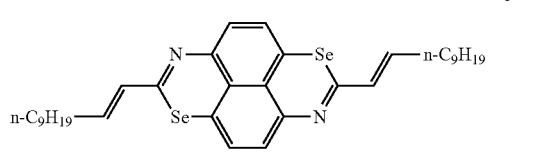
Compound 61
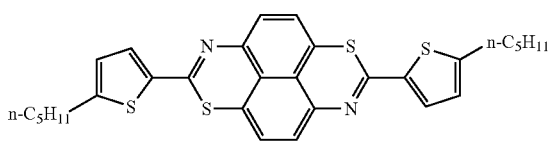
Compound 62
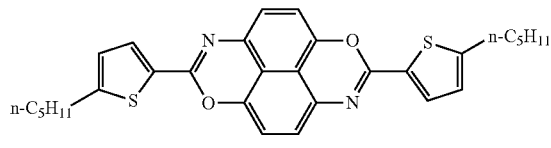
Compound 63
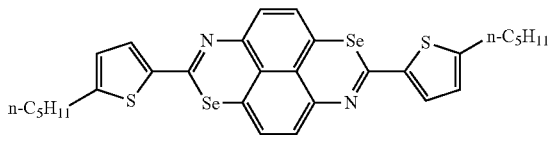
Compound 64
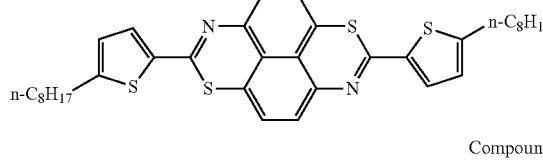
Compound 65
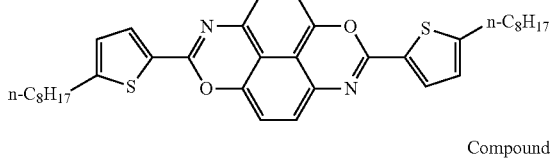
Compound 66
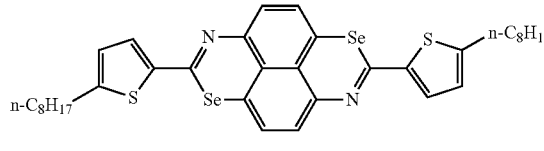
Compound 67
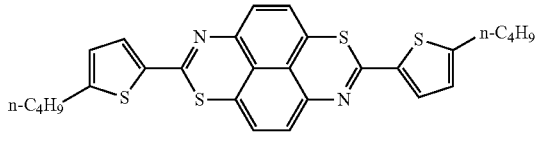

-continued
Compound 68
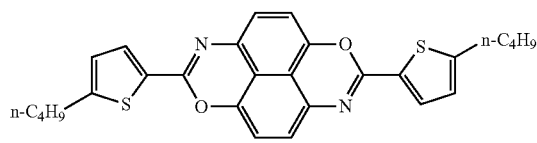
Compound 69
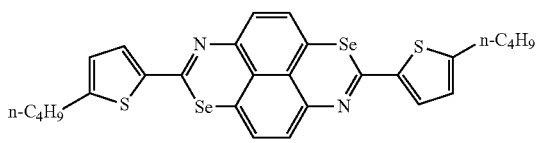
Compound 70
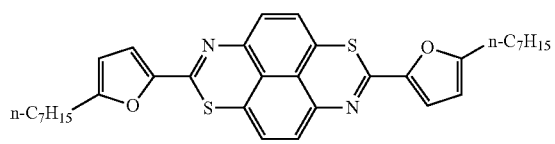
Compound 71
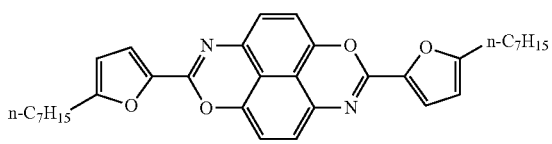
Compound 72
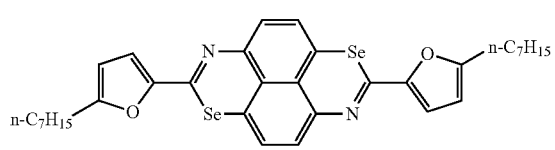
Compound 73
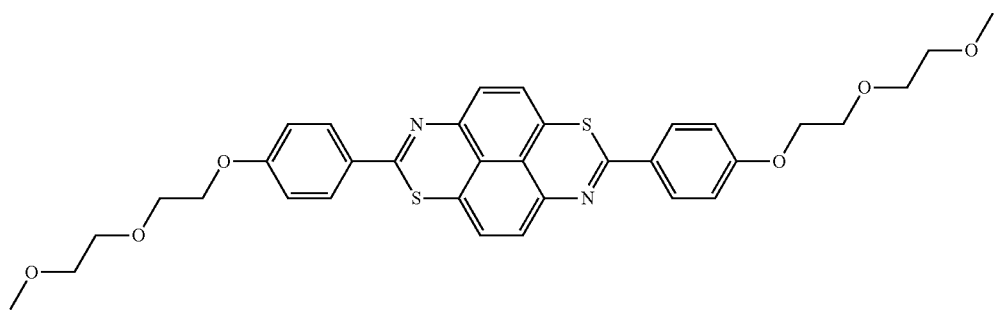
Compound 74
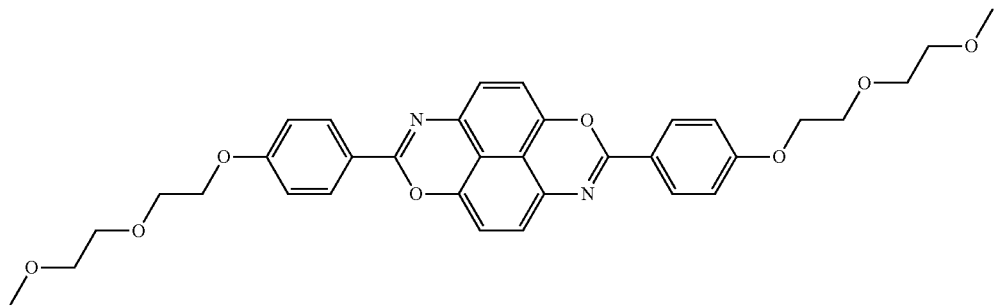
Compound 75
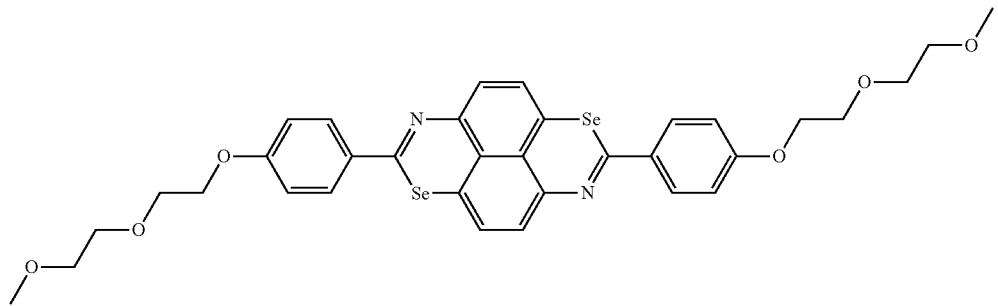

-continued
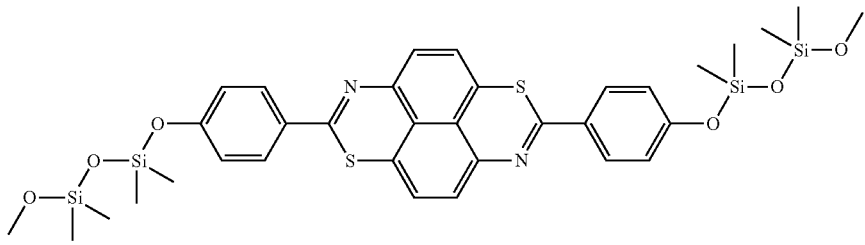
Compound 76
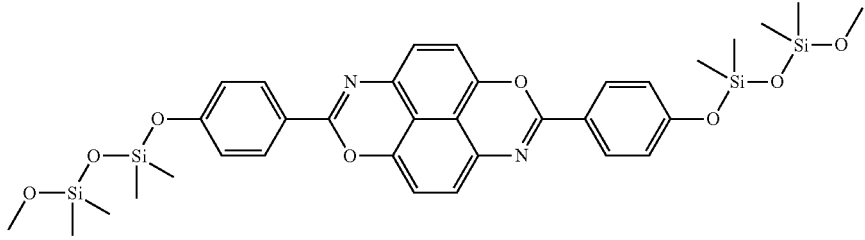
Compound 77
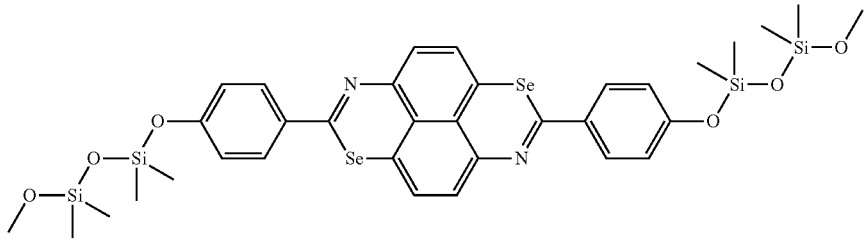
Compound 78
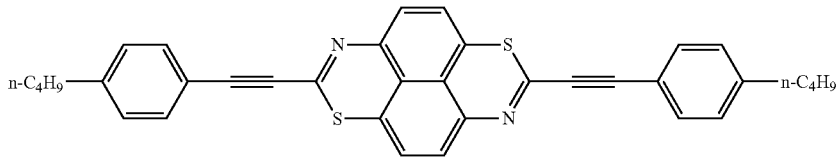
Compound 79
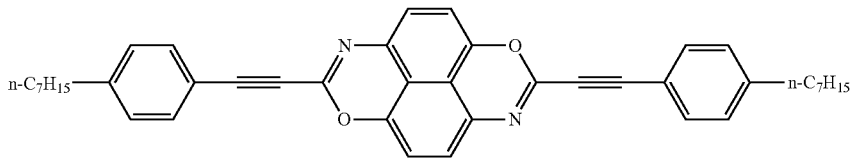
Compound 80
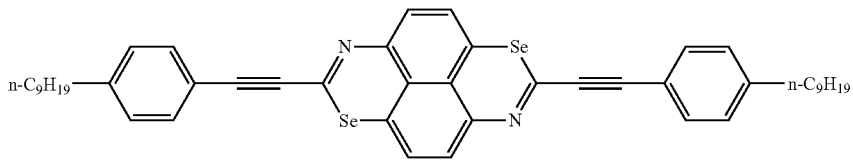
Compound 81
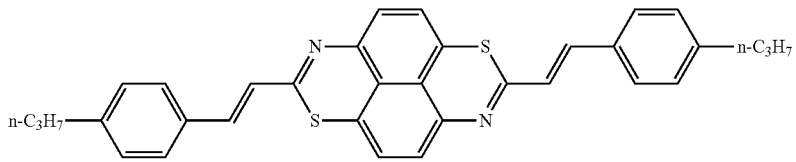
Compound 82
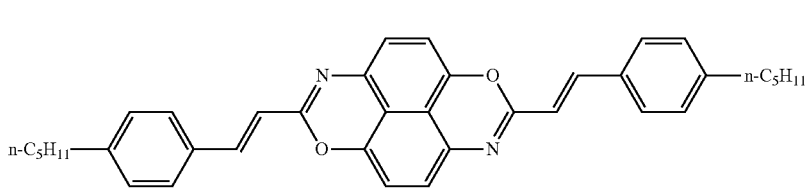
Compound 83

-continued
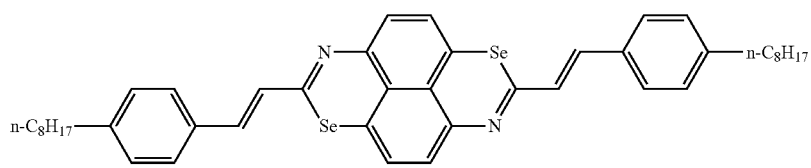
Compound 84
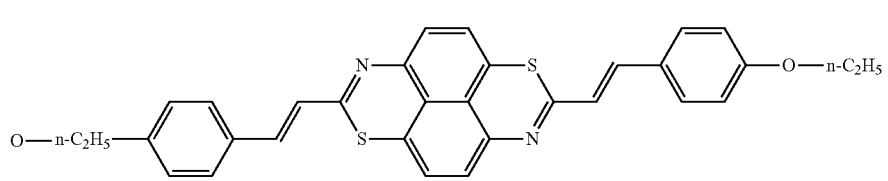
Compound 85
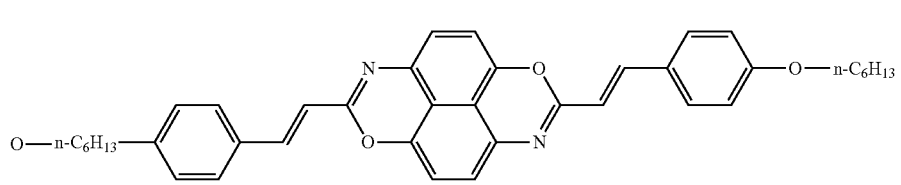
Compound 86
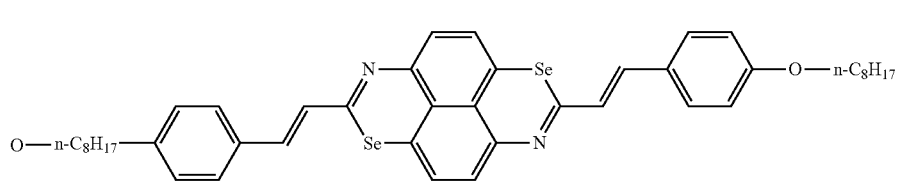
Compound 87
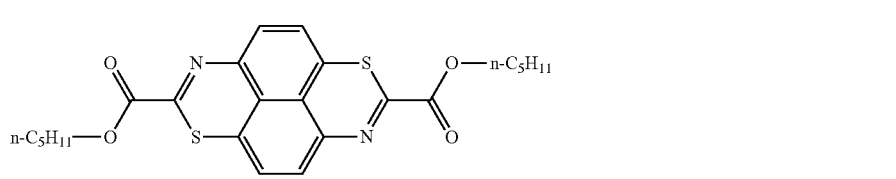
Compound 88
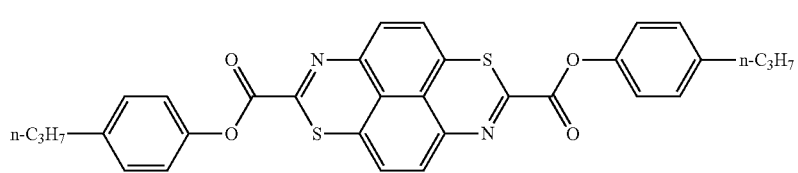
Compound 89
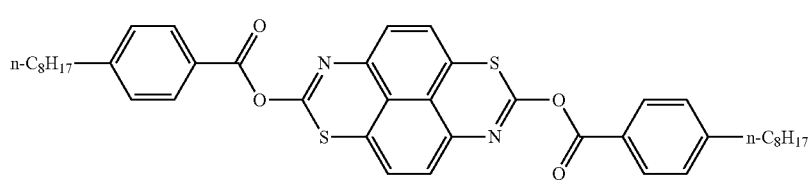
Compound 90
Compound 91
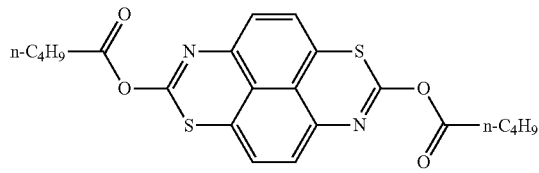
Compound 92
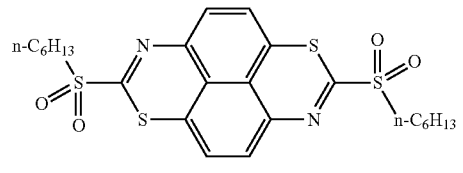

-continued
Compound 93
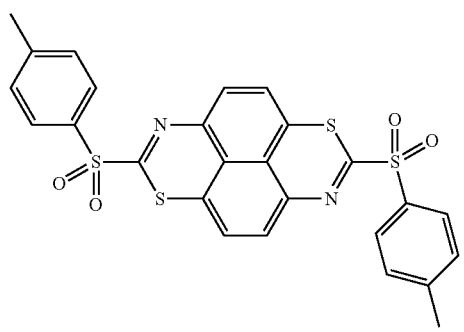
Compound 94
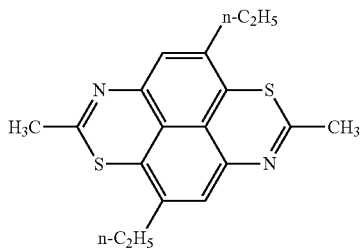
Compound 95
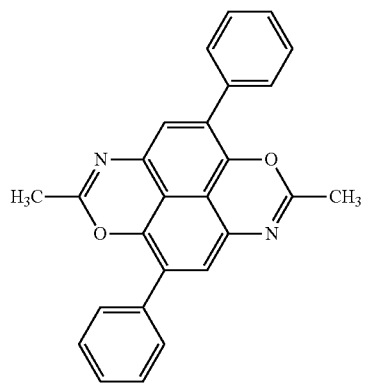
Compound 96
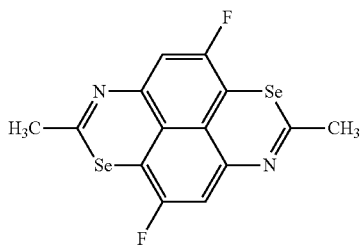
Compound 97
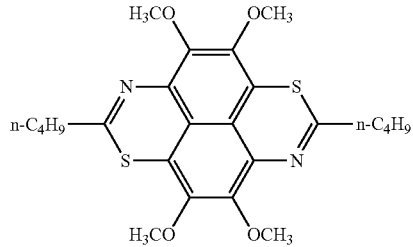
Compound 98
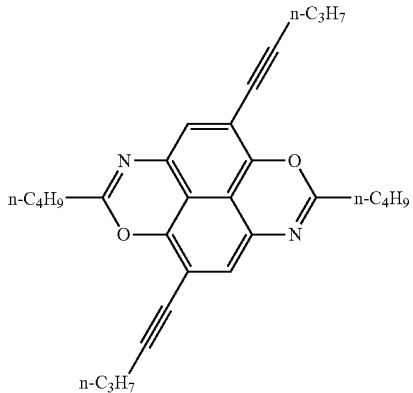
Compound 99
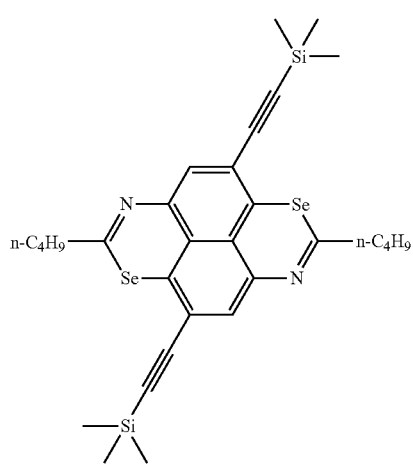
Compound 100
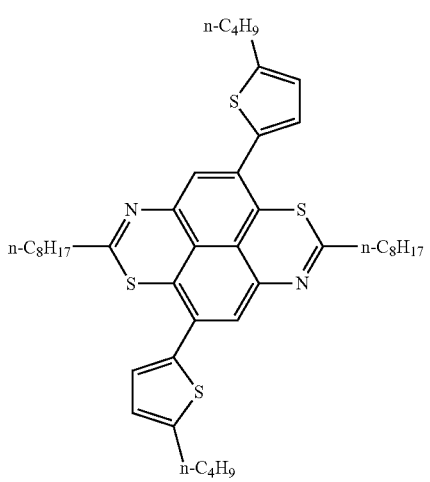

-continued
Compound 101
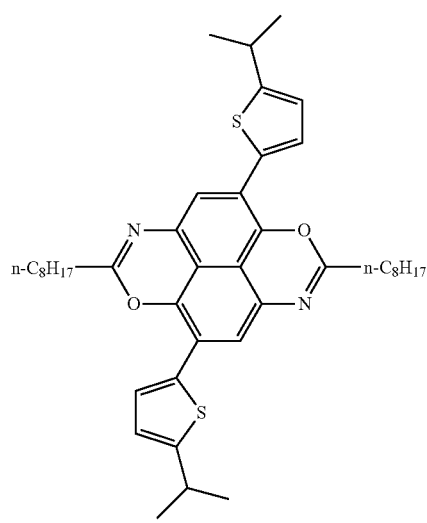
Compound 102
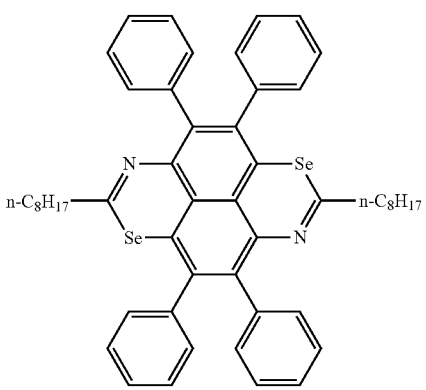
Compound 103
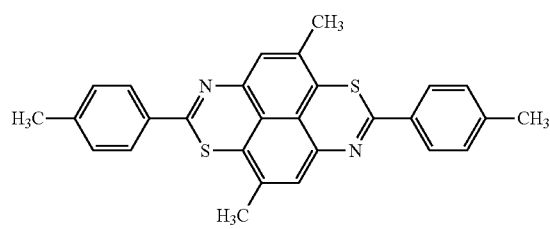
Compound 104
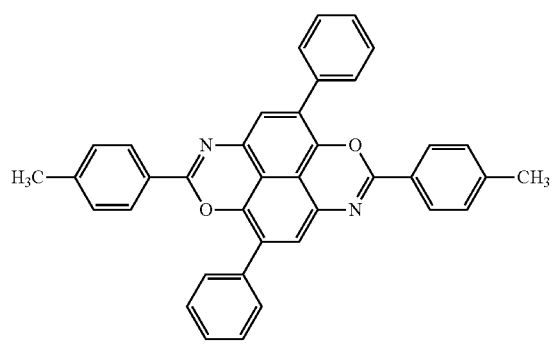
Compound 105
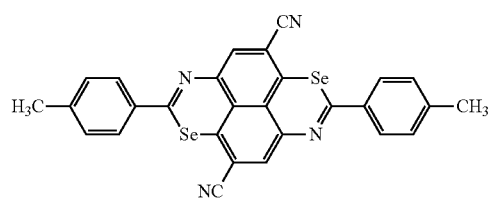
Compound 106
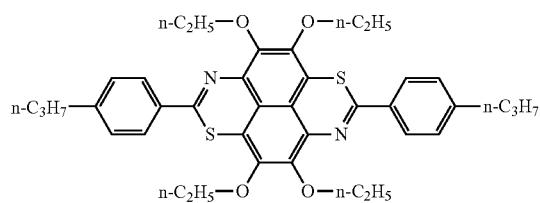
Compound 107
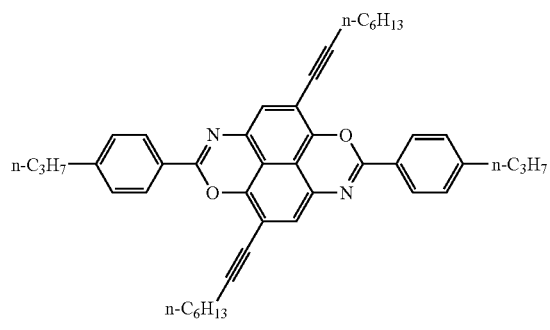
Compound 108
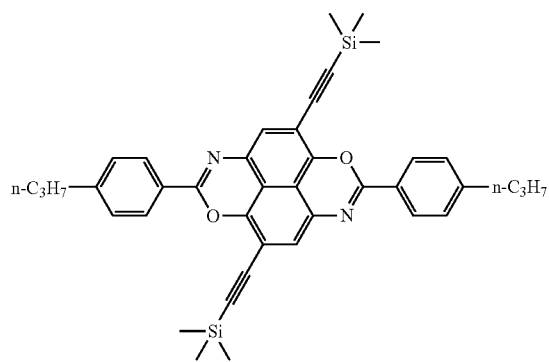

Compound 109
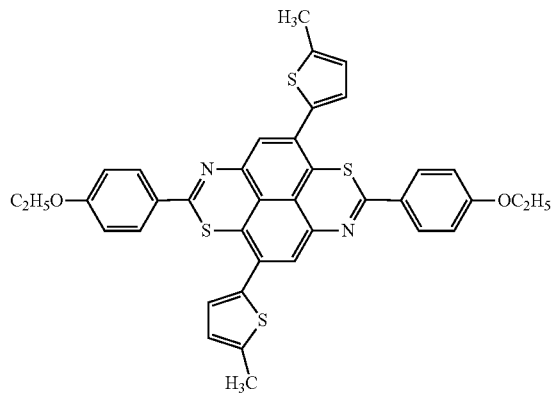
Compound 110
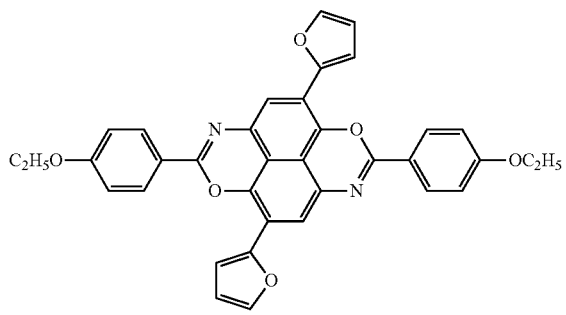
Compound 111
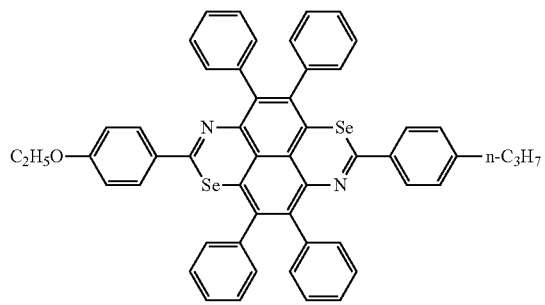
Compound 112
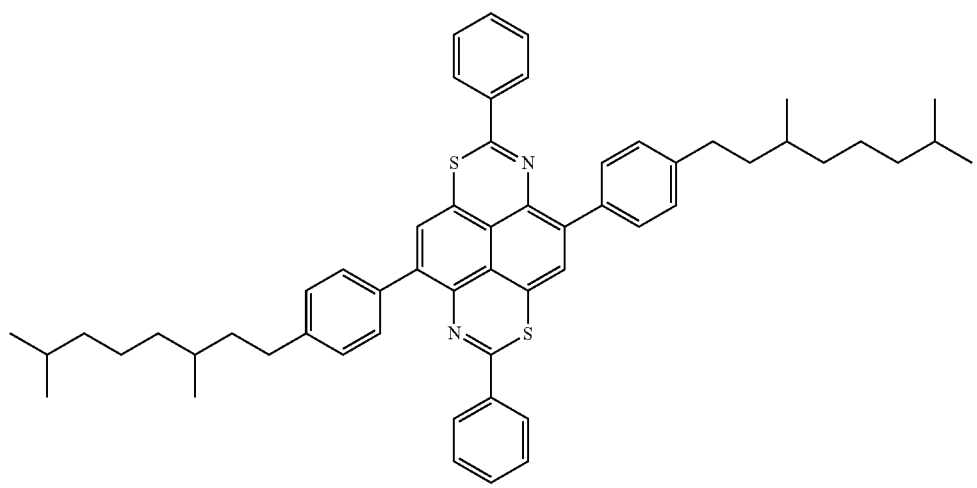

-continued
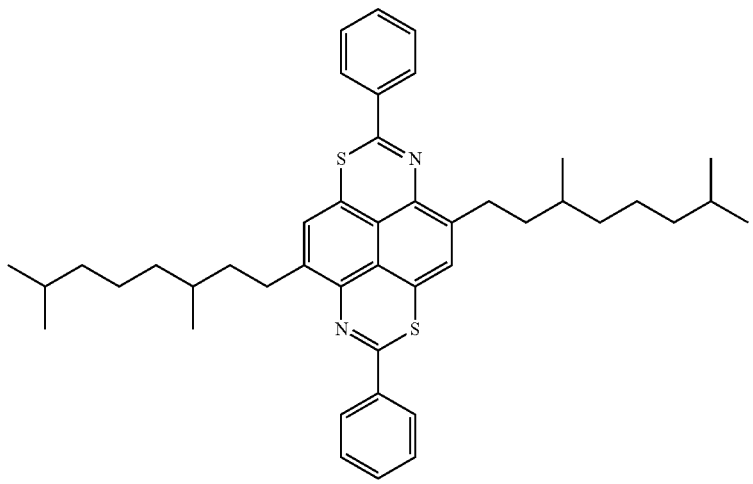
Compound 113
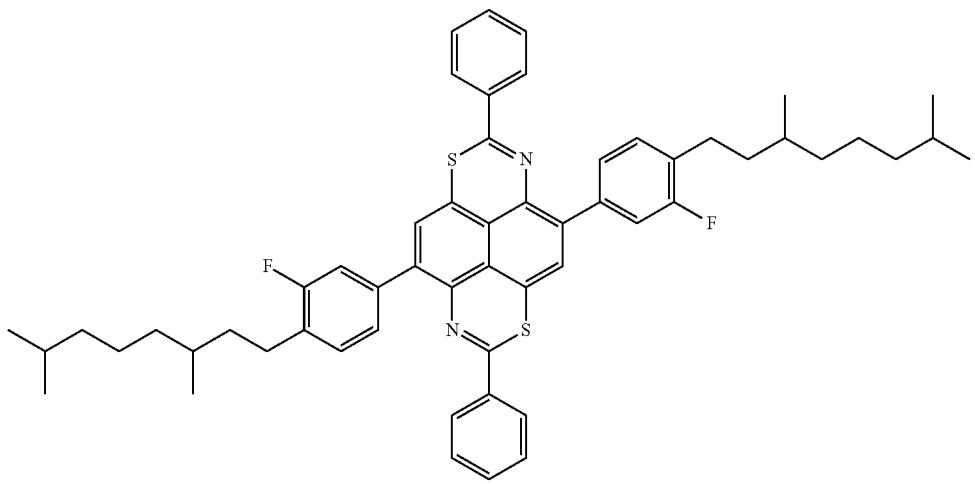
Compound 114
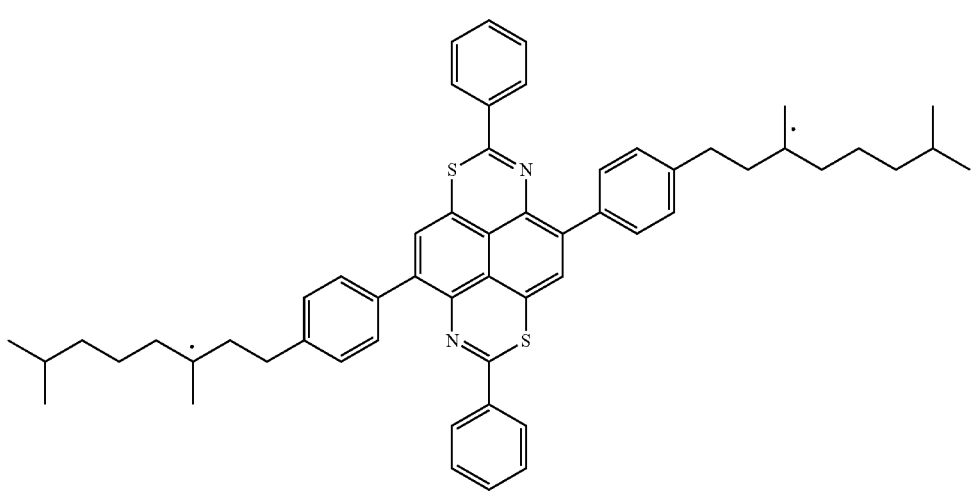
Compound 115

Compound 116
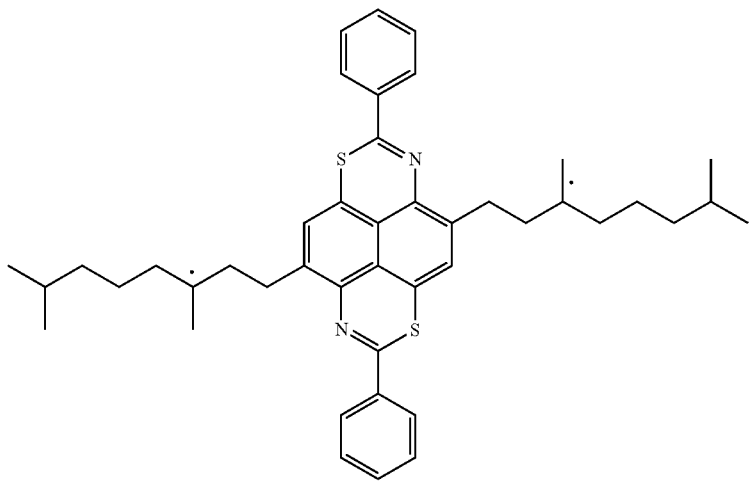
Compound 117
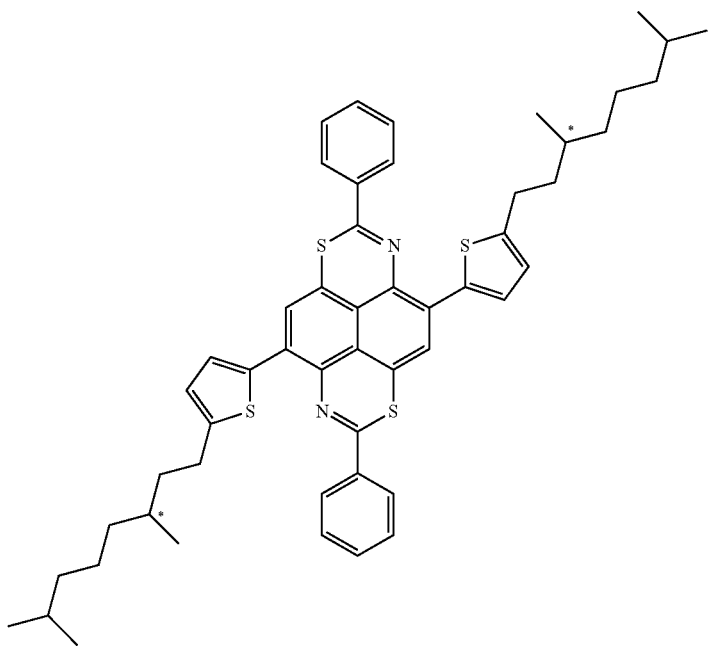
Compound 118
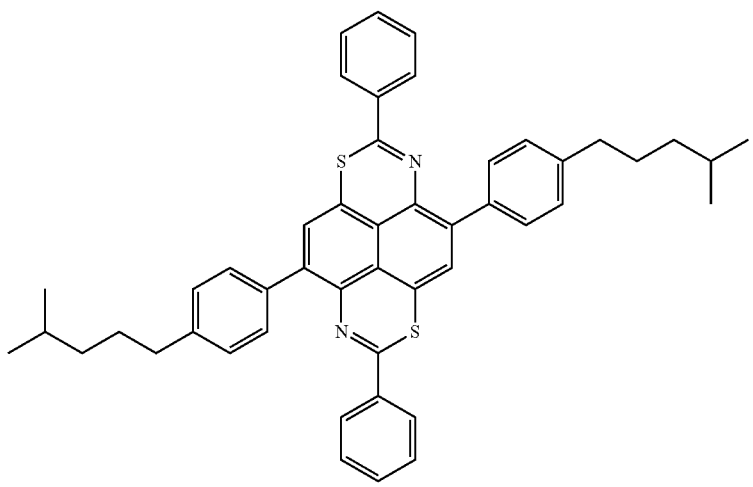

-continued
Compound 119
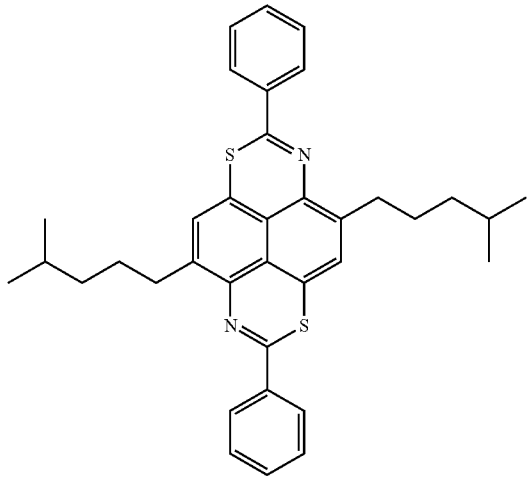
Compound 120
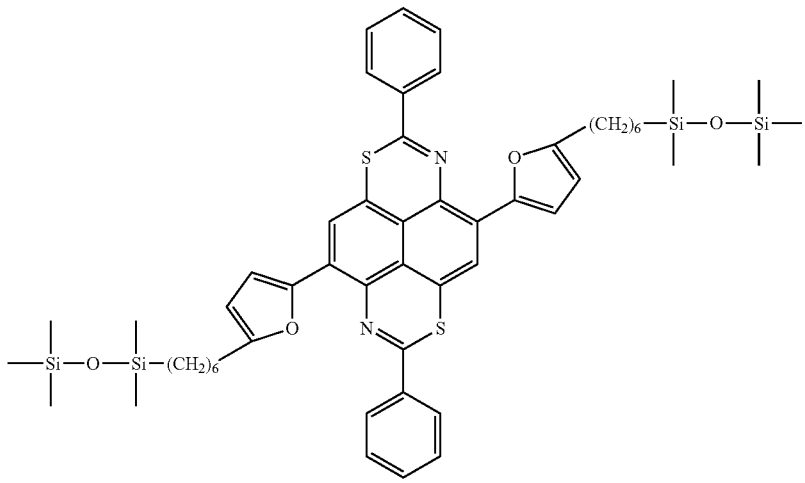
Compound 121
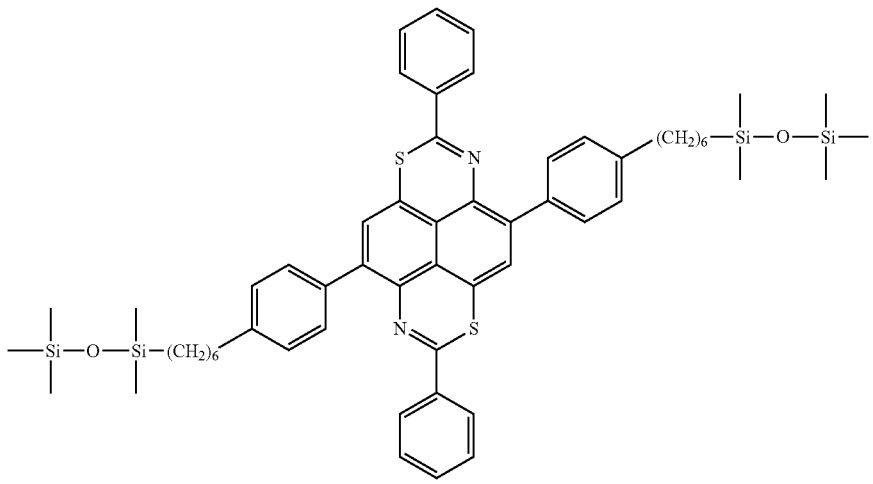

Compound 122
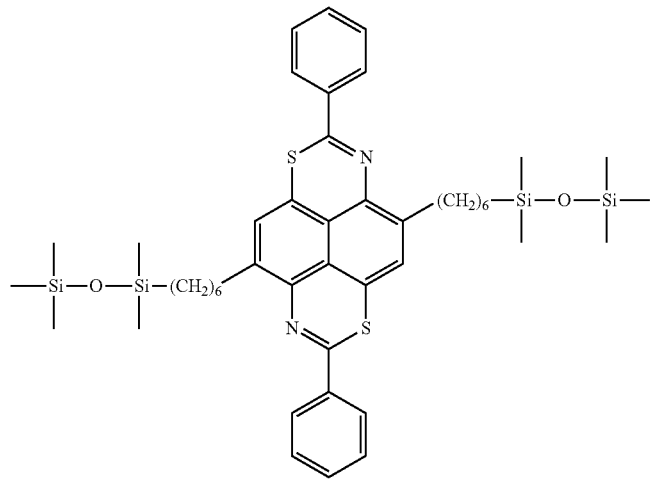
Compound 123
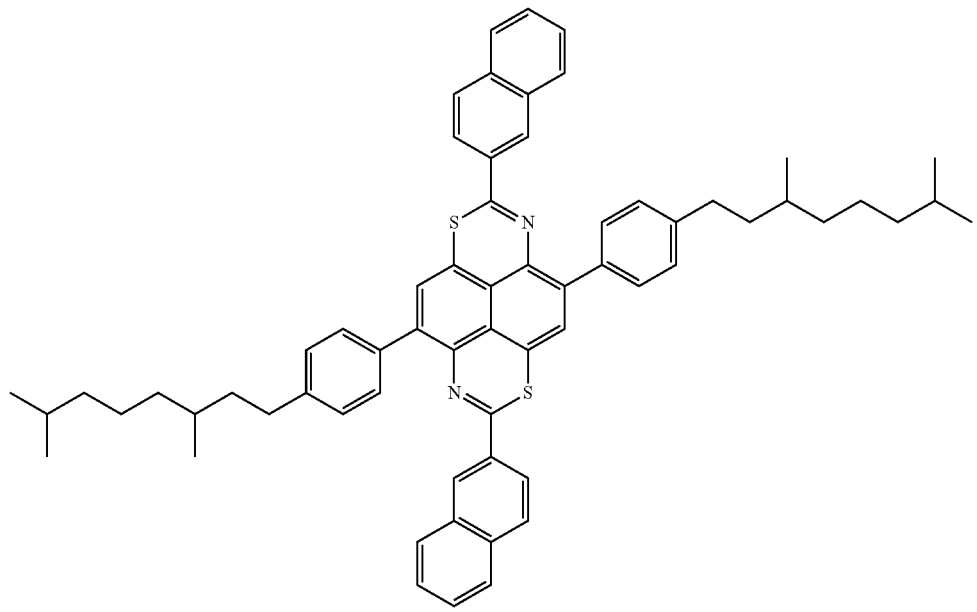
Compound 124
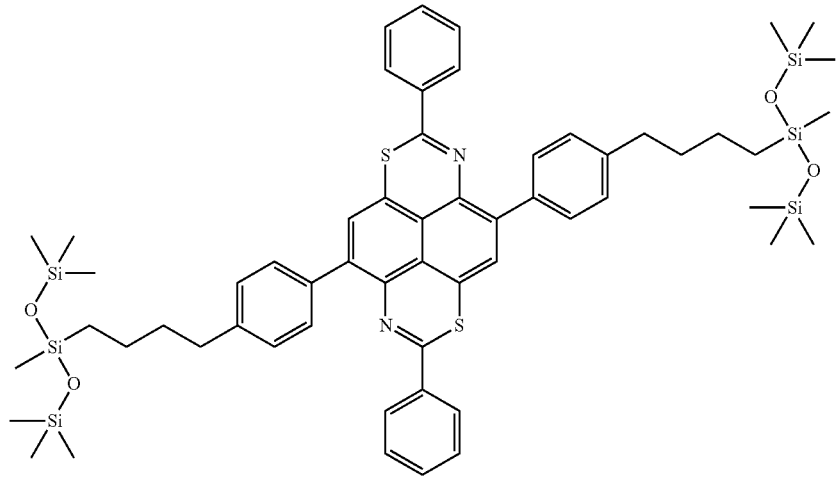

Compound 125

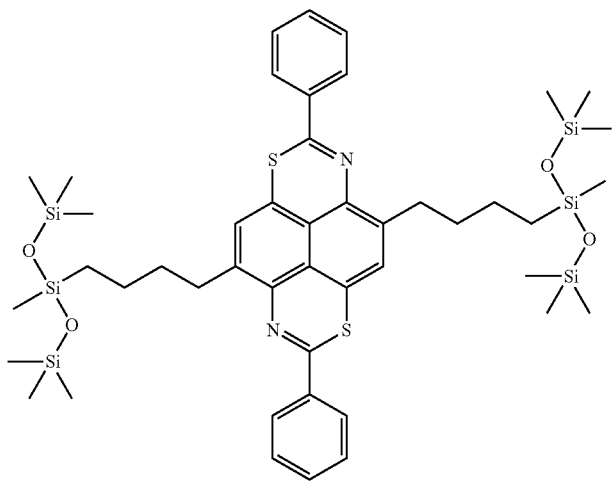

Compound 126

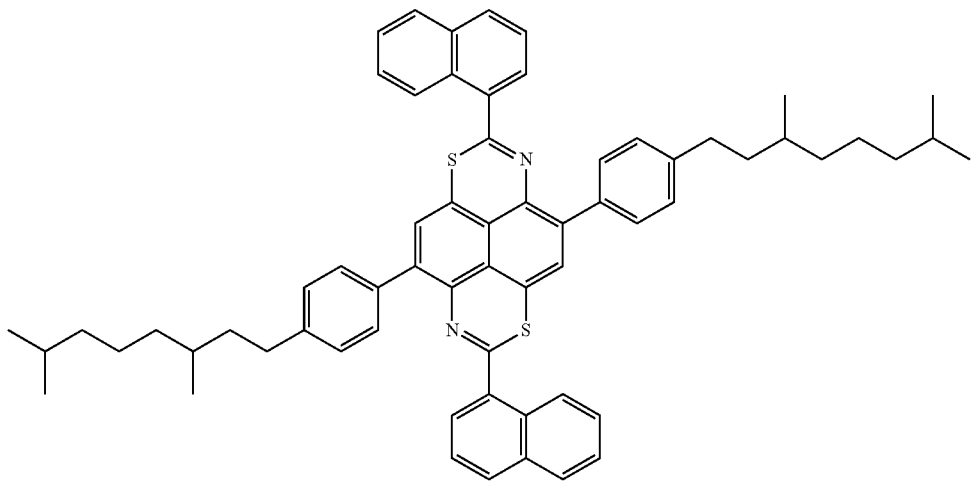

The compound represented by the formula (1) preferably has a molecular weight of 3,000 or less, more preferably 2,000 or less, further preferably 1,000 or less, and particularly preferably 850 or less. The molecular weight that is the upper limit or less is preferred since the compound has increased solubility in a solvent.

The molecular weight of the compound is preferably 300 or more, more preferably 350 or more, and further preferably 400 or more, from the standpoint of the stability of the film quality of the thin film.

In the case where the compound represented by the formula (1) is a high molecular weight compound having a repeating structure, a weight-average molecular weight is preferably 30,000 or more, more preferably 50,000 or more, and further preferably 100,000 or more. In the case where the compound represented by the formula (1) is a high molecular weight compound having a repeating structure, the weight-average molecular weight is preferably set to be equal to or more than the lower limit stated above, thereby enhancing the intermolecular interaction and achieving a high mobility.

Examples of the high molecular weight compound having a repeated structure include a π-conjugated polymer in which the compound represented by the formula (1) represents at least one of an arylene group and a heteroarylene group (thiophen or bithiophen) to express a repeating structure, and a pendant type polymer in which the compound represented by the formula (1) is bonded to a polymer main chain via aside chain. The polymer main chain is preferably polyacrylate, polyvinyl or polysiloxane, and the side chain is preferably an alkylene group or a polyethylene oxide group.

The compound represented by the formula (1) may be synthesized with reference to the methods described in Journal or American Chemical Society, 116, 925 (1994); Journal of Chemical Society, 221, (1951), etc.

In the reaction of forming the compound of the invention, any reaction condition may be used. The reaction solvent used may be any solvent. An acid or a base is preferably used for promoting the ring-forming reaction, and particularly a base is preferably used. The optimum reaction condition may vary depending on the structure of the target naphthobisthiazine derivatives or derivatives of a compound having naphthobisthiazine analog structure, or target naphthobisselenazin derivatives or derivatives of a compound having naphthobisselenazin analog structure, and may be determined with reference to the specific reaction shown in the aforementioned literature.

The synthesis intermediates having the various substituents may be synthesized by combining known reactions. The substituents may be introduced in any stage of the intermediates. The intermediates after synthesis is preferably purified by column chromatography, re-crystallization or the like, and then purified by sublimation. The sublimation purification not only isolates organic impurities, but also effectively removes an inorganic salt, a residual solvent and the like.

<Structure of Organic Thin Film Transistor>

The organic thin film transistor of the invention has a semiconductor active layer containing the compound represented by the formula (1).

The organic thin film transistor of the invention may further contain other layers in addition to the semiconductor active layer.

The organic thin film transistor of the invention is preferably used as an organic field effect transistor (FET), and is more preferably used as an insulated gate FET, in which the gate and the channel are insulated from each other.

Preferred embodiments of the organic thin film transistor of the invention will be described below with reference to the drawings, but the invention is not limited to the embodiments.

(Laminated Structure)

The laminated structure of the organic field effect transistor is not particularly limited, and various known structures may be used.

One example of the structure of the organic thin film transistor of the invention is a bottom-gate top-contact structure having a substrate as the lowermost layer having disposed thereon an electrode, an insulating layer, a semiconductor active layer (organic semiconductor layer), and two electrodes, in this order. In this structure, the electrode on the upper surface of the substrate as the lowermost layer is provided on apart of the substrate, and the insulating layer is disposed to be in contact with the substrate in the portion other than the electrode. The two electrodes disposed on the upper surface of the semiconductor active layer are disposed to be separated from each other.

A structure of a bottom-gate top-contact device is shown in FIG. 1. FIG. 1 is a schematic illustration showing a cross sectional structure of one example of the organic thin film transistor of the invention. The organic thin film transistor shown in FIG. 1 has a substrate 11 disposed as the lowermost layer, an electrode 12 disposed on a part of the upper surface of the substrate 11, and an insulating layer 13 disposed to cover the electrode 12 and to be in contact with the substrate 11 in the portion other than the electrode 12. A semiconductor active layer 14 is provided on the upper surface of the insulating layer 13, and two electrodes 15a and 15b, which are separated from each other, are disposed on parts of the semiconductor active layer 14.

In the organic thin film transistor shown in FIG. 1, the electrode 12 is a gate, and the electrodes 15a and 15b each are a drain or a source. The organic thin film transistor shown in FIG. 1 is an insulated gate FET, in which the channel, which is an electric current path between the drain and the source, and the gate are insulated from each other.

Another example of the structure of the organic thin film transistor of the invention is a bottom-gate bottom-contact device.

Figure 2:
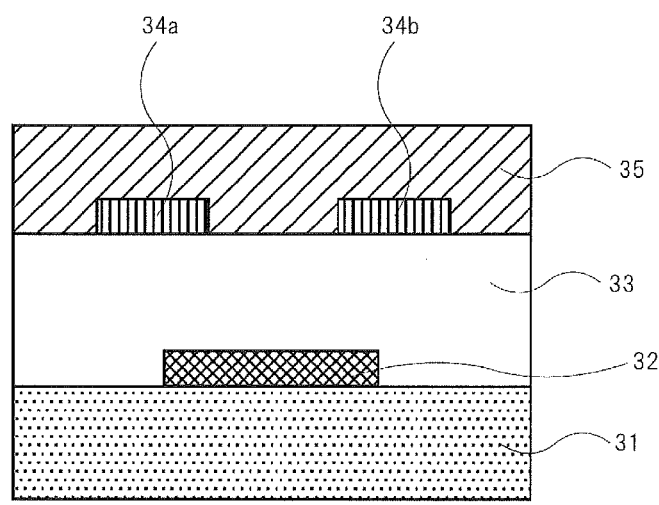
FIG. 2 is a schematic illustration showing a cross sectional structure of an organic thin film transistor that is produced as a substrate for measuring FET characteristics in the example of the invention.

A structure of a bottom-gate bottom-contact device is shown in FIG. 2. FIG. 2 is a schematic illustration showing a cross sectional structure of an organic thin film transistor that is produced as a substrate for measuring FET characteristics in the example of the invention. The organic thin film transistor shown in FIG. 2 has a substrate 31 disposed as the lowermost layer, an electrode 32 disposed on a part of the upper surface of the substrate 31, and an insulating layer 33 disposed to cover the electrode 32 and to be in contact with the substrate 31 in the portion other than the electrode 32.

A semiconductor active layer 35 is provided on the upper surface of the insulating layer 33, and electrodes 34a and 34b are disposed under the semiconductor active layer 35.

In the organic thin film transistor shown in FIG. 2, the electrode 32 is a gate, and the electrodes 34a and 34b each are a drain or a source. The organic thin film transistor shown in FIG. 2 is an insulated gate FET, in which the channel, which is an electric current path between the drain and the source, and the gate are insulated from each other.

Other preferred examples of the structure of the organic thin film transistor of the invention include a top-gate top-contact device and a top-gate bottom-contact device, in which an insulator and a gate electrode are disposed above a semiconductor active layer.

(Thickness)

The organic thin film transistor of the invention preferably has a total thickness of the transistor, for example, of from 0.1 to 0.5 µm, in the case where a thinner transistor is demanded.

(Sealing)

For shielding the organic thin film transistor device from the air and water to enhance the storage stability of the organic thin film transistor device, the entire organic thin film transistor device may be sealed with a metallic sealing canister, an inorganic material, such as glass and silicon nitride, a polymer material, such as parylene, a low molecular weight material, and the like.

Preferred embodiments of the layers of the organic thin film transistor of the invention will be described below, but the invention is not limited to the embodiments.

<Substrate>

(Material)

The organic thin film transistor of the invention preferably contains a substrate.

The material for the substrate is not particularly limited, and known materials may be used. Examples of the material include a polyester film, such as polyethylene naphthoate (PEN) and polyethylene terephthalate (PET), a cycloolefin polymer film, a polycarbonate film, a triacetyl cellulose (TAC) film, a polyimide film, these polymer films having an ultrathin glass layer laminated thereon, ceramics, silicone, quartz, glass, and the like, and silicone is preferred.

<Electrode>

(Material)

The organic thin film transistor of the invention preferably contains an electrode.

Examples of the material for the electrode include known electroconductive materials, for example, a metal material, such as Cr, Al, Ta, Mo, Nb, Cu, Ag, Au, Pt, Pd, In, Ni and Nd, an alloy material of the metal materials, a carbon material, and an electroconductive polymer, which may be used without particular limitation.

(Thickness)

The thickness of the electrode is not particularly limited and is preferably from 10 to 50 nm.

The gate width (or the channel width) W and the gate length (or the channel length) L are not particularly limited, and the ratio W/L is preferably 10 or more, and more preferably 20 or more.

<Insulating Layer>

(Material)

The material for the insulating layer is not particularly limited as far as the necessary insulating effect is obtained, and examples thereof include silicon dioxide, silicon nitride, a fluorine polymer insulating material, such as PTFE and CYTOP, a polyester insulating material, a polycarbonate insulating material, an acrylic polymer insulating material, an epoxy resin insulating material, a polyimide insulating material, a polyvinylphenol resin insulating material, and a poly-p-xylylene resin insulating material.

The upper surface of the insulating layer may be surface-treated, and preferred examples thereof used include an insulating layer formed of silicon dioxide, the surface of which is surface-treated by coating hexamethyldisilazane (HMDS) or octadecyltrichlorosilane (OTS) thereon.

(Thickness)

The thickness of the insulating layer is not particularly limited, and in the case where a thin insulating layer is demanded, the thickness thereof is preferably from 10 to 400 nm, more preferably from 20 to 200 nm, and particularly preferably from 50 to 200 nm.

<Semiconductor Active Layer>

(Material) The organic thin film transistor of the invention contains the compound represented by the formula (1), i.e., the compound of the invention, in the semiconductor active layer.

The semiconductor active layer may be a layer that is formed of the compound of the invention, or a layer containing a polymer binder described later in addition to the compound of the invention. The semiconductor active layer may contain a residual solvent used on forming the film.

The content of the polymer binder in the semiconductor active layer is not particularly limited, and the polymer binder is preferably used in a range of from 0 to 95% by mass, more preferably used in a range of from 10 to 90% by mass, further preferably used in a range of from 20 to 80% by mass, and particularly preferably used in a range of from 30 to 70% by mass.

(Thickness)

The thickness of the semiconductor active layer is not particularly limited, and in the case where a thin semiconductor active layer is demanded, the thickness thereof is preferably from 10 to 400 nm, more preferably from 10 to 200 nm, and particularly preferably from 10 to 100 nm.

[Organic Semiconductor Material for Non-Light Emitting Organic Semiconductor Device]

The invention also relates to an organic semiconductor material for a non-light emitting organic semiconductor device containing the compound represented by the formula (1), i.e., the compound of the invention.

(Non-Light Emitting Organic Semiconductor Device)

The non-light emitting organic semiconductor device referred herein means a device that is not intended to emit light. The non-light emitting organic semiconductor device is preferably a non-light emitting organic semiconductor device that uses an electronic element having a layer structure of thin films. The non-light emitting organic semiconductor device encompasses an organic thin film transistor, an organic photoelectric conversion device (such as a solid state imaging device for a photosensor, and a solar cell for energy conversion), a gas sensor, an organic rectifying device, an organic inverter, an information recording device, and the like. The organic photoelectric conversion device may be used for both a photosensor (i.e., a solid state imaging device) and energy conversion (i.e., a solar cell). Preferred examples of the device include an organic photoelectric conversion device and an organic thin film transistor, and more preferred examples thereof include an organic thin film transistor. Accordingly, the organic semiconductor device for a non-light emitting organic semiconductor device of the invention is preferably a material for an organic thin film transistor as described above.

(Organic Semiconductor Material)

The organic semiconductor material referred herein means an organic material that shows characteristics of a semiconductor. The organic semiconductor material includes a p-type (hole transporting) organic semiconductor, which shows conductivity with holes as a carrier, and an n-type (electron transporting) organic semiconductor, which shows conductivity with electrons as a carrier, as similar to a semiconductor material formed of an inorganic material.

The compound of the invention may be used as any of a p-type organic semiconductor material and an n-type organic semiconductor material, and is preferably used as a p-type organic semiconductor material. The flowability of a carrier in an organic semiconductor is shown by a carrier mobility $\mu$. The carrier mobility $\mu$ is preferably as large as possible, and is preferably $1\times10^{-3}$ cm$^2$/Vs or more, more preferably $5\times10^{-3}$ cm$^2$/Vs or more, particularly preferably $1\times10^{-2}$ cm$^2$/Vs or more, further particularly preferably $1\times10^{-1}$ cm$^2$/Vs or more, and still further particularly preferably 1 cm$^2$/Vs or more. The carrier mobility $\mu$ may be obtained from the characteristics of a field effect transistor (FET) device produced or by a time-of-flight (TOF) measurement method.

[Organic Semiconductor Thin Film for Non-Light Emitting Organic Semiconductor Device]

(Material)

The invention also relates to an organic semiconductor thin film for a non-light emitting organic semiconductor device containing the compound represented by the formula (1), i.e., the compound of the invention.

The organic semiconductor thin film for a non-light emitting organic semiconductor device of the invention contains the compound represented by the formula (1), i.e., the compound of the invention, and an embodiment thereof that contains no polymer binder is also preferred.

The organic semiconductor thin film for a non-light emitting organic semiconductor device of the invention may contain the compound represented by the formula (1), i.e., the compound of the invention, and a polymer binder.

Examples of the polymer binder include an insulating polymer, such as polystyrene, polycarbonate, polyarylate, polyester, polyamide, polyimide, polyurethane, polysiloxane, polysulfone, polymethyl methacrylate, polymethyl acrylate, cellulose, polyethylene and polypropylene, copolymers thereof, a photoconductive polymer, such as polyvinylcarbazole and polysilane, and an electroconductive polymer and a semiconductor polymer, such as polythiophene, polypyrrole, polyaniline and poly-p-phenylenevinylene.

The polymer binder may be used solely or as a combination of plural kinds thereof.

The organic semiconductor material and the polymer binder may be uniformly mixed, or a part or the whole thereof may be phase-separated, and from the standpoint of the charge mobility, such a structure that the organic semiconductor and the binder are phase-separated in the thickness direction in the film is most preferred since the charge migration of the organic semiconductor may not be inhibited by the binder.

Taking the mechanical strength of the thin film into consideration, a polymer binder having a high glass transition temperature is preferred, and taking the charge mobility into consideration, a polymer binder having a structure that contains no polar group, a photoconductive polymer, and an electroconductive polymer are preferred.

The amount of the polymer binder used is not particularly limited, and the polymer binder may be preferably used in a range of from 0 to 95% by mass, more preferably used in a range of from 10 to 90% by mass, further preferably used in a range of from 20 to 80% by mass, and particularly preferably used in a range of from 30 to 70% by mass, in the organic semiconductor thin film for a non-light emitting organic semiconductor device of the invention.

In the invention, an organic thin film having good film quality may be obtained by using the compound having the aforementioned structure. Specifically, the compound of the invention has good crystallinity to enable formation of a film having a sufficient thickness, and thus the organic semiconductor thin film for a non-light emitting organic semiconductor device of the invention thus obtained may have good quality.

(Film Forming Method)

The compound of the invention may be formed as a film on a substrate by any method.

On forming the film, the substrate may be heated or cooled, and the film quality and the molecular packing in the film may be controlled by changing the temperature of the substrate. The temperature of the substrate is not particularly limited, and is preferably in a range of from 0 to 200° C., more preferably in a range of from 15 to 100° C., and particularly preferably in a range of from 20 to 95° C.

On forming a film of the compound of the invention on a substrate, the film may be formed by a vacuum process or a solution process, both of which are preferred.

Specific examples of the film formation by a vacuum process include a physical vapor phase growing method, such as a vacuum vapor deposition method, a sputtering method, an ion plating method and a molecular beam epitaxy (MBE) method, and a chemical vapor deposition (CVD) method, such as plasma polymerization, and a vacuum vapor deposition method is preferably used.

The film formation by a solution process means a method, in which an organic compound is dissolved in a solvent capable of dissolving the same, and a film is formed by using the resulting solution. Specific examples thereof used include ordinary methods, for example, a coating method, such as a casting method, a dip coating method, a die coater method, a roll coater method, a bar coater method and a spin coating method, a printing method, such as an ink-jet method, a screen printing method, a gravure printing method, a flexography printing method, an offset printing method and a microcontact printing method, and a Langmuir-Blodgett (LB) method, and a casting method, a spin coating method, an ink-jet method, a gravure printing method, a flexography printing method, an offset printing method and a microcontact printing method are particularly preferably used.

The organic semiconductor thin film for a non-light emitting organic semiconductor device of the invention is preferably produced by a solution coating method. In the case where the organic semiconductor thin film for a non-light emitting organic semiconductor device of the invention contains a polymer binder, the thin film is preferably formed such a method that the material for forming the layer and the polymer binder are dissolved or dispersed in a suitable solvent to prepare a coating liquid, which is then coated by various coating methods to form the thin film.

The coating solution for a non-light emitting organic semiconductor device of the invention capable of being used for film formation by a solution process will be described below.

[Coating Solution for Non-Light Emitting Organic Semiconductor Device]

The invention also relates to a coating solution for a non-light emitting organic semiconductor device containing the compound represented by the formula (1), i.e., the compound of the invention.

In the case where the film is formed on a substrate by a solution process, the material for forming the layer may be dissolved or dispersed in a suitable organic solvent (for example, a hydrocarbon solvent, such as hexane, octane, decane, toluene, xylene, mesitylene, ethylbenzene, decalin and 1-methylnaphthalene, a ketone solvent, such as acetone, methyl ethyl ketone, methyl isobutyl ketone and cyclohexanone, a halogenated hydrocarbon solvent, such as dichloromethane, chloroform, tetrachloromethane, dichloroethane, trichloroethane, tetrachloroethane, chlorobenzene, dichlorobenzene and chlorotoluene, an ester solvent, such as ethyl acetate, butyl acetate and amyl acetate, an alcohol solvent, such as methanol, propanol, butanol, pentanol, hexanol, cyclohexanol, methyl cellosolve, ethyl cellosolve and ethylene glycol, an ether solvent, such as dibutyl ether, tetrahydrofuran, dioxane and anisole, an amide or imide solvent, such as N, N-dimethylformamide, N, N-dimethylacetamide, 1-methyl-2-pyrrolidone and 1-methyl-2-imidazolidinone, a sulfoxide solvent, such as dimethylsulfoxide, and a nitrile solvent, such as acetonitrile) and/or water to prepare a coating liquid, which may be then coated by various coating methods to form the thin film. The solvent may be used solely or as a combination of plural kinds thereof. Among these, a hydrocarbon solvent, a halogenated hydrocarbon solvent and an ether solvent are preferred, toluene, xylene, mesitylene, tetralin, dichlorobenzene and anisole are more preferred, and toluene, xylene, tetralin and anisole are particularly preferred. The concentration of the compound represented by the formula (1) in the coating liquid is preferably from 0.1 to 80% by mass, more preferably from 0.1 to 10% by mass, and particularly preferably from 0.5 to 10% by mass, by which a film having an arbitrary thickness may be formed.

For forming a film by a solution process, it is necessary to dissolve the materials in the aforementioned solvent, but it is insufficient that the materials are simply dissolved in the solvent. In general, a material to be formed into a film by a vacuum process may be dissolved in a solvent in a certain extent. However, the solution process includes a step of evaporating the solvent to form a thin film, after coating the materials dissolved in a solvent, and most of materials that are not suitable for forming a film by a solution process have high crystallinity, and thus may be disadvantageously crystallized (agglomerated) in the step to fail to provide a favorable thin film. The compound represented by the formula (1) is advantageous also in such a point that the compound may not cause the disadvantageous crystallization (agglomeration).

As the coating solution for a non-light emitting organic semiconductor device of the invention, such an embodiment is also preferred that contains the compound represented by the formula (1), i.e., the compound of the invention, and contains no polymer binder.

The coating solution for a non-light emitting organic semiconductor device of the invention may contain the compound represented by the formula (1), i.e., the compound of the invention, and a polymer binder. In this case, the thin film may be formed in such a manner that the material for forming the layer and the polymer binder are dissolved or dispersed in the suitable solvent described above to prepare a coating liquid, which is then coated by various coating method to form the thin film. The polymer binder may be selected from those described above.

EXAMPLE

The features of the invention will be described more specifically with reference to examples and comparative examples below. The materials, the amounts used, the ratios, the contents of processes, the procedures of processes, and the like shown in the examples may be appropriately changed unless they deviate the substance of the invention. Accordingly, the scope of the invention is not construed as being limited to the following examples.

Example 1

Synthesis Example 1

Synthesis of Compound 7

The Compound 7 as the compound represented by the formula (1) was synthesized by the specific synthesis procedures shown by the following scheme.

The Compound 7c was synthesized with reference to the following literatures:

Journal or American Chemical Society, 116, 925 (1994); and Journal of Chemical Society, 221, (1951).

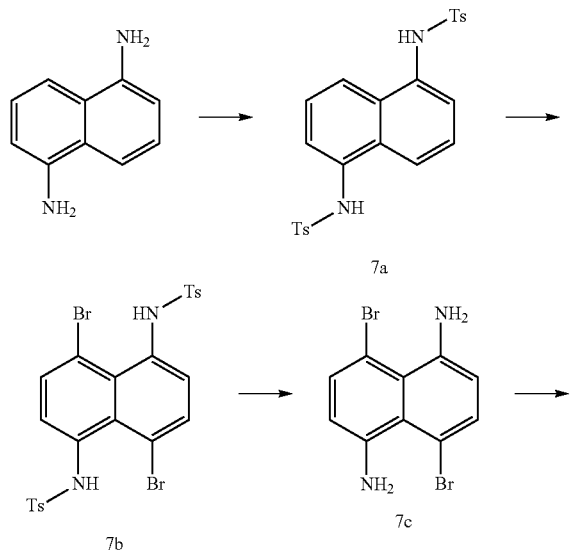

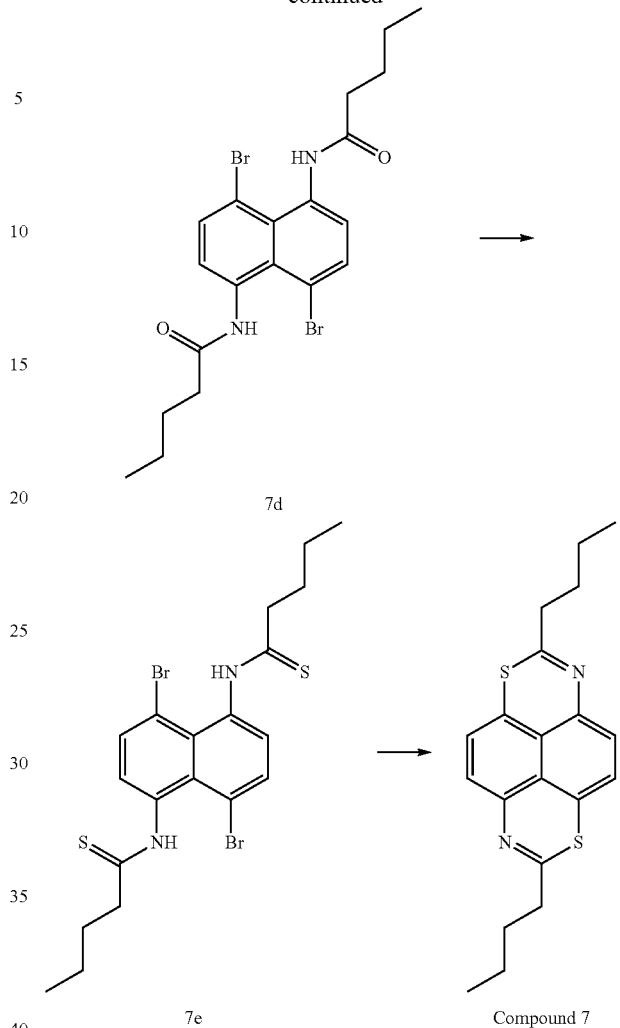

Synthesis of Compound 7a p-Toluenesulfonylchloride (34 g) was slowly added to pyrinze solution (125 ml) of 1,5-diaminonaphtalene (10 g), and the mixture was stirred at the room temperature for 2 hours. The reaction liquid was poured into the ice water, and the solid matter thus deposited was collected by filtration. The obtained crude crystals were rinsed with ethanol to provide Compound 7a (29 g).

Synthesis of Compound 7b

A glacial acetic acid solution of the Compound 7a (10 g) was heated and stirred at 95° C., and bromine (2 mL) diluted with a glacial acetic acid solution (10 mL) was dropped thereto. The mixture was reacted for 10 minutes, cooled down and then filtered to provide crude crystals as a gray solid. The crude crystals were re-crystallized in nitrobenzene to provide Compound 7b (6.8 g).

Synthesis of Compound 7c

A concentrated sulfuric acid of the Compound 7b (5 g) was stirred at the room temperature for 24 hours. The reaction liquid was poured into the ice water, and then the solid matter thus deposited was collected by filtration. The solid matter was dispersed again in the ice water and neutralized with the aqueous ammonia to provided Compound 7c (0.5 g).

Synthesis of Compound 7d

At the room temperature, butyryl chloride (2.6 mL) was dropped to a pyridine solution of the Compound 7c (2 g), and the mixture was stirred for 2 hours. The reaction liquid was poured into the ice water, and the solid matter was filtered under reduced pressure. The resultant matter was dispersed in methanol, stirred for 1 hour, and then filtered to provide Compound 7d (1.39 g).

Synthesis of Compound 7e

The Compound 7d (1.2 g) and Lawsson Reagent (1.48 g) were add to a mixture solution of THF (360 mL) and toluene (72 mL), and the mixture was stirred under heating to reflux for 3 hours. Toluene was remained in the solution by evaporating THF only. The resultant toluene solution was stirred at 60° C. for 1 hour. The insoluble matter was filtered to provide Compound 7e (0.5 g).

Synthesis of Compound 7

The Compound 7e (0.4 g) and cesium carbonate (1.33 g) were reacted in dimethylacetamide at 120° C. for 2 hours. The reaction liquid was poured into the ice water, and the solid matter thus deposited was collected by filtration. The filtrate was subjected to repeated re-crystallization in THF to synthesize target Compound 7 (0.12 g). The compound was identified by elemental analysis, NMR and mass spectrum.

Synthesis Example 2

Synthesis of Compound 112

The Compound 112 as the compound represented by the formula (1) was synthesized by the specific synthesis procedures shown by the following scheme.

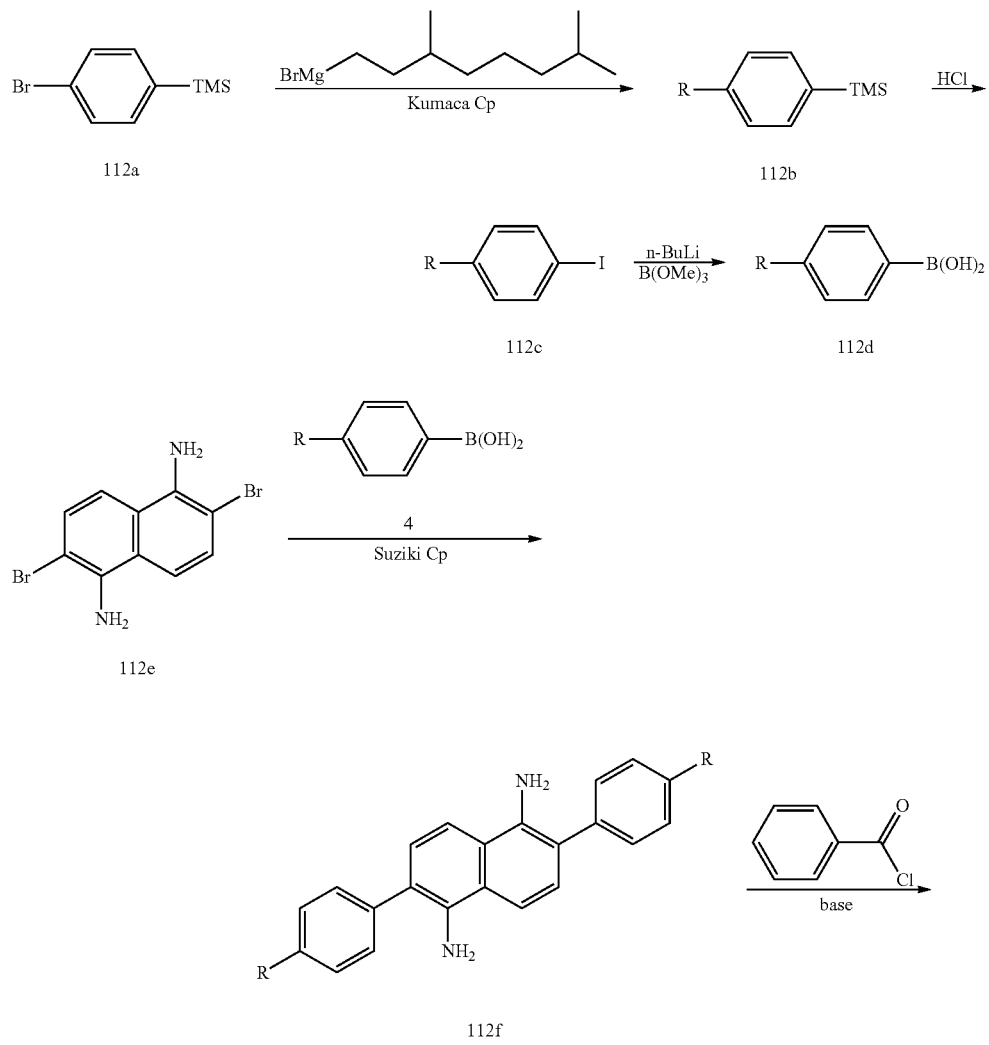

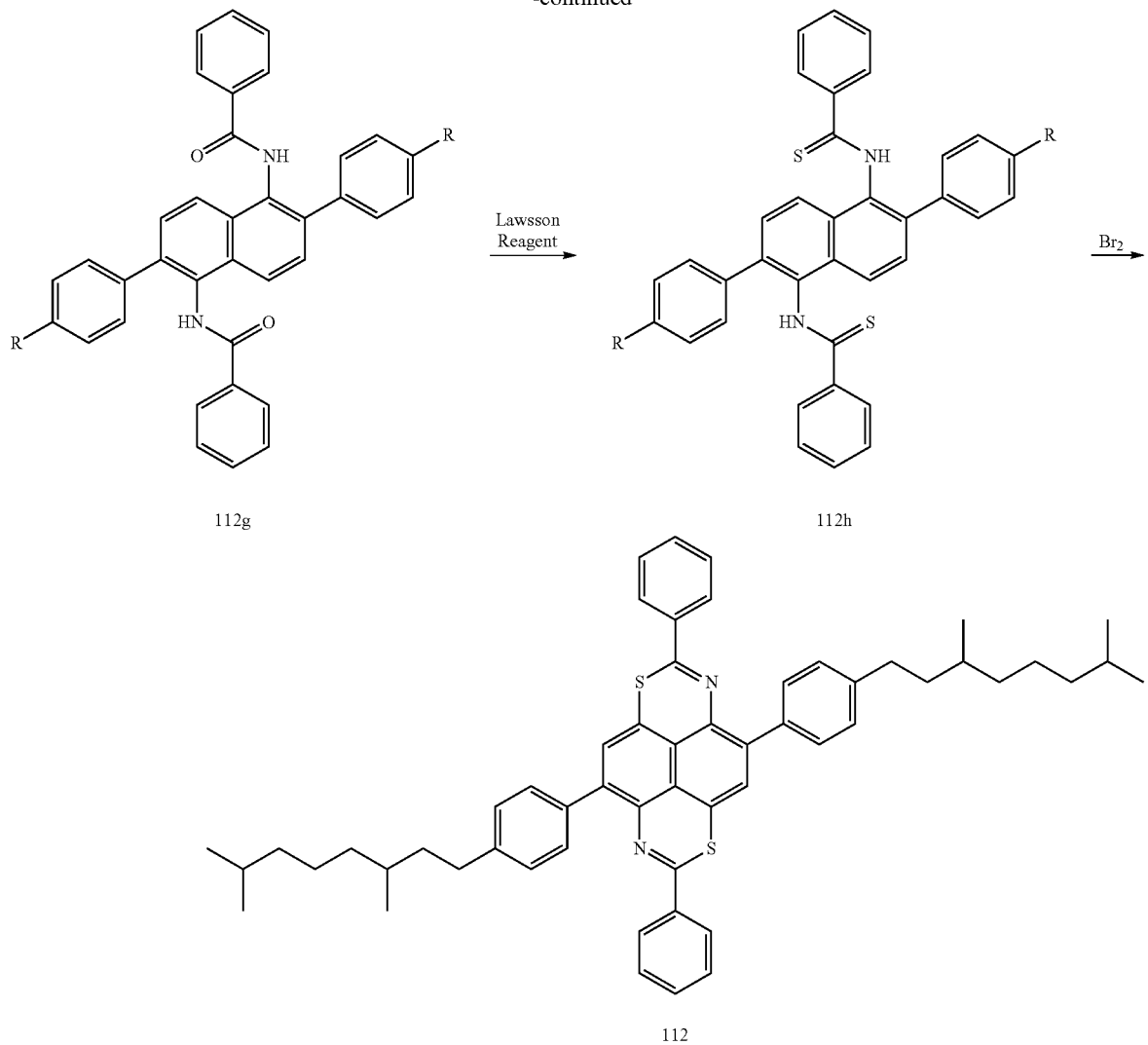

Synthesis of Compound 112b

Magnesium (8.5 g, 354 mmol) and dimethylether (50 ml) were placed in a 1 L three-necked flask, and stirred at the room temperature. Iodine and dibromoethane were added thereto, and then the mixture was reacted until no foam was created any more. A solution of 3,7-dimethyloctane (65 g, 295 mmol) in diethylether (=245 mL) was dropped to thereto. The mixture was reacted at the room temperature for 1 hour to provide a Grignard reagent (0.81 M)

The Compound 112a (6.85 g, 30 mmol), $PdCl_2$ (dppf).$CH_2Cl_2$ (0.73 g, 0.9 mmol) and THF were placed in a 2 L three-necked flask and substituted with nitrogen very carefully. Then, the Grignard reagent (75 mL) was slowly dropped thereto. The mixture was reacted for 12 hours under reflux, and 500 mL of water was added to the mixture. The resultant mixture was quenched. The reaction liquid was filtered with Celite, separated (extracted three times in ethyl acetate), purified by a silica gel column (hexane). Compound 112b was obtained as white solid (8.7 g, yield: 97%).

Synthesis of Compound 112c

The Compound 112b (33.5 g, 115 mmol) and dichloromethane (780 ml) were placed in a 2 L three-necked flask. A solution of dicholoromethan (=120 mL) in 1-Cl (19.7 g, 121 mmol) was dropped thereto at −78° C. The mixture was reacted for 30 minutes, and then the reaction liquid was slowly poured into an aqueous solution of sodium bisulfite (=1 L) which was cooled in an ice bath. The liquid was stirred at the room temperature for 1 hour, and extracted two times with dichloromethane to provide Compound 112c as while solid (39 g, yield: 97%).

Synthesis of Compound 112d

The Compound 112c (15 g, 43.6 mmol) and THF (150 mL) were placed in a 1 L three-necked flask. n-BuLi (1.6M in hexane, 33 mL, 52.3 mmol) was slowly dropped thereto at −78° C. The mixture was reacted at −78° C. for 20 minutes, and then, a solution of trimethoxyborane (13.6 g, 131 mmol) in THF (=14 mL) was dropped to the mixture. The mixture was reacted at the room temperature for 1 hour, quenched with 1N HCl solution, separated (extracted three times in ethyl acetate), and purified by a silica gel column (hexane/ethyl acetate=20/1, hexane/ethyl acetate=4/1, and ethyl acetate only), thereby obtaining Compound 112d as white solid (6 g, yield: 43%).

Synthesis of Compound 112f

The Compound 112d (18.2 g, 69.3 mmol), Compound 112e (7.3 g, 23.1 mmol) and 2-(dicyclohexylphosphino)-2',6'-dimethoxybiphenyl (Sphos) (2.3 g, 5.54 mmol), postassium phosphate (24.4 g, 115 mmol), THF/water (200 mL/400 mL) and palladium acetate (0.52 g, 2.31 mmol) were placed in a 1 L three-necked flask. The mixture was refluxed for 3 hours in a nitrogen atmosphere. The resultant was filtered with Celite, separated (extracted three times in toluene) and re-crystallized in toluene/hexane to provide Compound 112f as white solid (9.4 g, yield: 69%).

Synthesis of Compound 112g

The Compound 112f (4 g, 6.78 mmol) and pyridine (=40 mL) were placed in a 300 mL eggplant flask, and dissolved completely at the room temperature. After benzoyl chloride (2.86 g, 20.3 mmol) was dropped thereto, the mixture was reacted for 10 minutes. The powder, which was deposited by pouring the water, was filtered and rinsed with methanol to provide Compound 112g as white solid (5.1 g, yield: 94%).

Synthesis of Compound 112h

The Compound 112g (5.1 g, 6.38 mmol), Lawsson reagent (3.1 g, 7.66 mmol) and THF/toluene (45 mL/9 mL) were placed in a 500 mL eggplant flask, and refluxed for 1 hour. After the reaction, THF was removed by evaporation. The resultant was purified by a silica gel column (toluene) to provide Compound 112h (3.97 g, yield: 95%).

Synthesis of Compound 112

The Compound 112h (4.85 g, 5.8 mmol) and chloroform (=200 mL) were place in a 1 L three-necked eggplant flask. After bromine (2.78 g, 17.4 mmol) was dropped thereto at 0° C., the mixture was reacted for 10 minutes. The reaction liquid was quenched by pouring an aqueous solution of sodium bisulfite (=20 mL), and extracted two times in chloroform. The resultant was purified by a silica gel column (hexane/toluene=90/10) to synthesize Compound 112h as red solid (4.22 g, yield: 88%).

Figure 3:
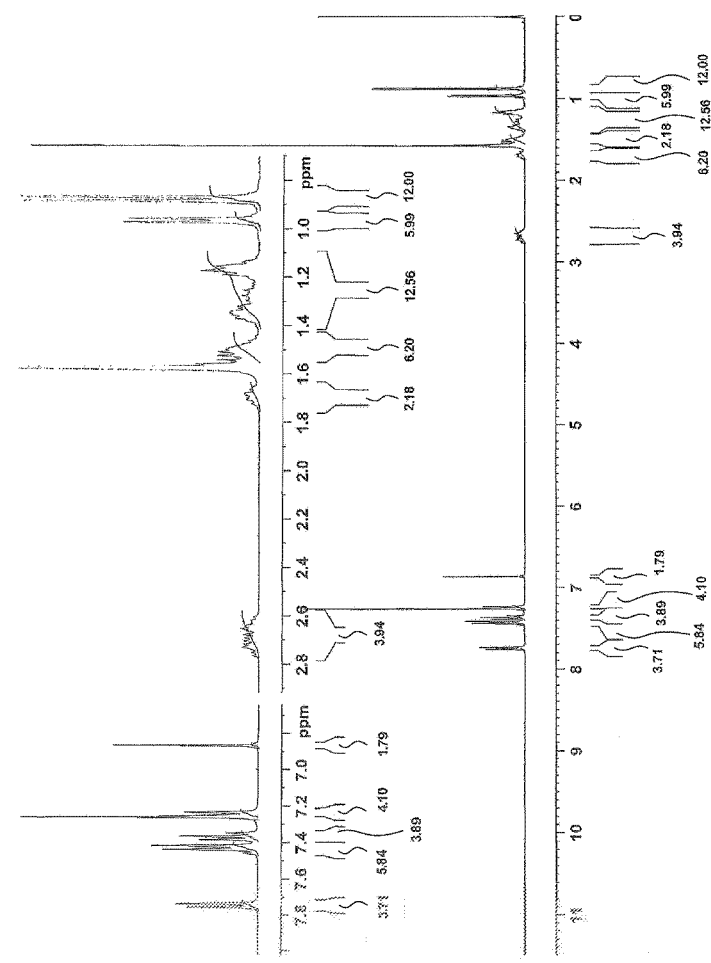
FIG. 3 shows the $^1$H-NMR chart of the compound 112.

The result of the identification of the structure of the Compound 112 by $^1$H-NMR is shown below and in FIG. 3.

The other compounds represented by the formula (1) were synthesized in the similar manner as for the Compound 7 or 112.

Comparative compounds 1 to 3 used in a semiconductor active layer (organic semiconductor layer) of comparative devices were synthesized according to the methods described in the literatures. The structures of the comparative compounds 1 to 3 are shown below.

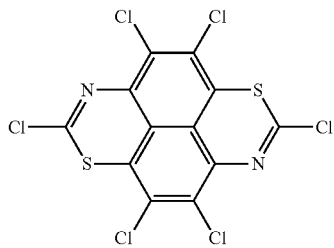

Comparative Compound 1 described in DE 2224746

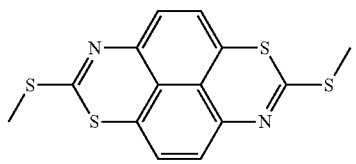

Comparative Compound 2 described in Japanese Patent Aplication No. 5-160798

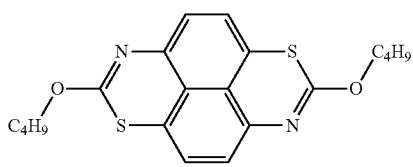

Comparative Compound 3 described in Japanese Patent Aplication No. 5-160798

<Production and Evaluation of Devices>

All the materials used for producing devices were purified by sublimation, and were confirmed to have a purity (absorption intensity area ratio at 254 nm) of 99.5% or more by high-performance liquid chromatography (TSKgel ODS-100Z, available from Tosoh Corporation).

Example 2

Formation of Semiconductor Active Layer (Organic Semiconductor Layer) only with Compound The compound of the invention or the comparative compound (1 mg each) and toluene (1 mL) were mixed and heated to 100° C. to prepare a coating solution for a non-light emitting organic semiconductor device. The coating solution was cast on a substrate for measuring FET characteristics thermal annealed at 120° C. for 30 minutes to form an organic semiconductor thin film for a non-light emitting organic semiconductor device, thereby providing an organic thin film transistor device of Example 1 for measuring FET characteristics. The substrate for measuring FET characteristics used was a silicon substrate having a bottom-gate bottom-contact structure having chromium/gold electrodes (gate width W=100 mm, gate length L=100 μm) disposed in an interdigitated form as source and drain electrodes, and SiO$_2$ (thickness: 200 nm) as an insulating film (the schematic structural illustration shown in FIG. 2).

The FET characteristics of the organic thin film transistor device of Example 2 were evaluated in terms of the carrier mobility and the change in the threshold voltage after repeated driving by using a semiconductor parameter analyzer (4156C, produced by Agilent Technologies, Inc.) having a semi-automatic prober (AX-2000, produced by Vector Semiconductor Co., Ltd.) connected thereto under a normal pressure nitrogen atmosphere.

The results obtained are shown in Table 1 below.

(a) Carrier Mobility

While applying a voltage of −80 V between the source electrode and the drain electrode of the organic thin film transistor device (FET device), the gate voltage was changed within a range of from 20 to −100 V, and the carrier mobility μ was calculated by the following expression showing the drain current $I_d$.

$$I_d = (W/2L)\mu C_i (V_g - V_{th})^2$$

wherein L represents the gate length, W represents the gate width, $C_i$ represents the capacity of the insulating layer per unit area, $V_g$ represents the gate voltage, and $V_{th}$ represents the threshold voltage. A device that exhibited a carrier mobility of less than $1 \times 10^{-5}$ cm$^2$/Vs was not subjected to the subsequent evaluation of (b) the change in the threshold voltage after repeated driving due to the too low property thereof.

(b) Change in Threshold Voltage after Repeated Driving

While applying a voltage of −80 V between the source electrode and the drain electrode of the organic thin film transistor device (FET device), the gate voltage was changed 100 times within a range of from 20 to −100 V, and the same measurement as in the measurement (a) above to evaluate the difference ($|V_1-V_0|$) between the threshold voltage $V_0$ before repeated driving and the threshold voltage $V_1$ after repeated driving according to the following three grades. A smaller value thereof shows higher repeated driving stability of the device and thus is preferred.

A: $|V_1-V_0| \leq 5$ V
B: $5 < |V_1-V_0| \leq 10$ V
C: $|V_1-V_0| > 10$ V

TABLE 1

| Device No. | Organic Semiconductor Material | Carrier Mobility (cm$^2$/Vs) | Change in Threshold Voltage after Repeated Driving | Note |
|---|---|---|---|---|
| Device 1 | Compound 7 | $6 \times 10^{-1}$ | A | invention |
| Device 2 | Compound 8 | $5 \times 10^{-1}$ | A | invention |
| Device 3 | Compound 9 | $1 \times 10^{-1}$ | A | invention |
| Device 4 | Compound 10 | $2 \times 10^{-1}$ | A | invention |
| Device 5 | Compound 11 | $8 \times 10^{-2}$ | A | invention |
| Device 6 | Compound 13 | $3 \times 10^{-1}$ | A | invention |
| Device 7 | Compound 14 | $6 \times 10^{-2}$ | A | invention |
| Device 8 | Compound 17 | $6 \times 10^{-2}$ | A | invention |
| Device 9 | Compound 19 | $1 \times 10^{-1}$ | A | invention |
| Device 10 | Compound 20 | $9 \times 10^{-2}$ | A | invention |
| Device 11 | Compound 21 | $8 \times 10^{-2}$ | A | invention |
| Device 12 | Compound 27 | $9 \times 10^{-2}$ | A | invention |
| Device 13 | Compound 33 | $1 \times 10^{-1}$ | A | invention |
| Device 14 | Compound 34 | $2 \times 10^{-1}$ | A | invention |
| Device 15 | Compound 37 | $4 \times 10^{-1}$ | A | invention |
| Device 16 | Compound 38 | $4 \times 10^{-1}$ | A | invention |
| Device 17 | Compound 55 | $3 \times 10^{-1}$ | A | invention |
| Device 18 | Compound 56 | $4 \times 10^{-1}$ | A | invention |
| Device 19 | Compound 59 | $2 \times 10^{-1}$ | A | invention |
| Device 20 | Compound 61 | $3 \times 10^{-1}$ | A | invention |
| Device 21 | Compound 62 | $4 \times 10^{-1}$ | A | invention |
| Device 22 | Compound 88 | $4 \times 10^{-2}$ | A | invention |
| Device 23 | Compound 112 | $7 \times 10^{-1}$ | A | invention |
| Device 24 | Compound 116 | $1 \times 10^{-1}$ | A | invention |
| Device 25 | Compound 123 | $5 \times 10^{-1}$ | A | invention |
| Comparative Device 1 | Comparative Compound 1 | $2 \times 10^{-5}$ | C | comparison |
| Comparative Device 2 | Comparative Compound 2 | $1 \times 10^{-3}$ | B | comparison |
| Comparative Device 3 | Comparative Compound 3 | $2 \times 10^{-4}$ | C | comparison |

It was understood from Table 1 that the organic thin film transistor devices using the compounds of the invention had a high carrier mobility and a small change in the threshold voltage after repeated driving. Accordingly, it was understood that the compound of the invention was favorably used as an organic semiconductor material for a non-light emitting organic semiconductor device.

On the other hand, the organic thin film transistor devices using the Comparative Compounds 1, 2 and 3 had a low carrier mobility. The organic thin film transistor devices using the Comparative Compounds 1, 2 and 3 had a large change in the threshold voltage after repeated driving.

In the case where the coating solution was casted on a substrate for measuring FET characteristics in nitrogen atmosphere, and the coating solution was casted on the substrate heated up to 90° C. in nitrogen atmosphere, instead of performing thermalannealing at 120° C. for 30 minutes, the same results was obtained as those listed in Table 1.

Example 3

Formation of Semiconductor Active Layer (Organic Semiconductor Layer) with Both Compound and Binder Organic thin film transistor devices for measuring FET characteristics were produced in the same manner as in Example 1 except for using a coating solution prepared in such a manner that the compound of the invention or the comparative compound (1 mg each), 1 mg of PαMS (poly (α-methylstyrene), Mw: 300,000, produced by Sigma-Aldrich, Inc.) and toluene (1 mL) were mixed and heated to 100° C., and then evaluated in the same manner as in Example 2.

TABLE 2

| Device No. | Organic Semiconductor Material | Carrier Mobility (cm$^2$/Vs) | Change in Threshold Voltage after Repeated Driving | Note |
|---|---|---|---|---|
| Device 26 | Compound 1 | $7 \times 10^{-2}$ | A | invention |
| Device 27 | Compound 2 | $2 \times 10^{-2}$ | A | invention |
| Device 28 | Compound 6 | $5 \times 10^{-2}$ | A | invention |
| Device 29 | Compound 7 | $4 \times 10^{-1}$ | A | invention |
| Device 30 | Compound 9 | $1 \times 10^{-1}$ | A | invention |
| Device 31 | Compound 10 | $1 \times 10^{-1}$ | A | invention |
| Device 32 | Compound 13 | $9 \times 10^{-2}$ | A | invention |
| Device 33 | Compound 19 | $6 \times 10^{-2}$ | A | invention |
| Device 34 | Compound 22 | $8 \times 10^{-2}$ | A | invention |
| Device 35 | Compound 28 | $7 \times 10^{-2}$ | A | invention |
| Device 36 | Compound 40 | $1 \times 10^{-1}$ | A | invention |
| Device 37 | Compound 55 | $1 \times 10^{-1}$ | A | invention |
| Device 38 | Compound 91 | $8 \times 10^{-2}$ | A | invention |
| Device 39 | Compound 112 | $8 \times 10^{-1}$ | A | invention |
| Device 40 | Compound 113 | $2 \times 10^{-1}$ | A | invention |
| Device 41 | Compound 123 | $3 \times 10^{-1}$ | A | invention |
| Comparative Device 4 | Comparative Compound 1 | $6 \times 10^{-6}$ | C | comparison |
| Comparative Device 5 | Comparative Compound 2 | $2 \times 10^{-3}$ | B | comparison |
| Comparative Device 6 | Comparative Compound 3 | $4 \times 10^{-4}$ | B | comparison |

It was understood from Table 2 that the organic thin film transistor devices having a semiconductor active layer formed by using the compounds of the invention along with the binder had a high carrier mobility and a small change in the threshold voltage after repeated driving. Accordingly, it was understood that the compound of the invention was favorably used as an organic semiconductor material for a non-light emitting organic semiconductor device.

On the other hand, the organic thin film transistor devices having a semiconductor active layer formed by using the Comparative Compounds 1, 2 and 3 along with the binder had a low carrier mobility. The organic thin film transistor devices having a semiconductor active layer formed by using the Comparative Compounds 1 and 2 along with the binder had a large change in the threshold voltage after repeated driving.

In the case where the coating solution obtained by mixing the compound of the invention or the comparative compound, PαMS and toluene, and by heating at 100° C. was used, instead of the coating solution obtained by mixing the compound of the invention or the comparative compound, PαMS and toluene, the same results was obtained as those listed in Table 2.

It was understood from the observation with an optical microscope of the organic thin film transistor devices obtained in Example 3 that the thin films using PαMS as a binder all had considerably high smoothness and uniformity of the film.

It was understood from these results that the comparative devices having a semiconductor active layer formed with the composite system of the binder and the comparative compound had a considerably low carrier mobility, whereas the organic thin film transistor devices of the invention having a semiconductor active layer formed with both the compound of the invention and the binder had a good carrier mobility, a small change in the threshold voltage after repeated driving, and considerably high smoothness and uniformity of the film.

Example 4

Formation of Semiconductor Active Layer (Organic Semiconductor Layer)

A silicon wafer having a gate insulating film of $SiO_2$ (thickness: 370 nm) was subjected to a surface treatment with octyltrichlorosilane.

The compound of the invention or the comparative compound (1 mg each) and toluene (1 mL) were mixed to prepare a coating solution for a non-light emitting organic semiconductor device. The coating solution was cast on the octyltrichlorosilane-treated silicon wafer heated to 90° C. under nitrogen atmosphere to form an organic semiconductor thin film for a non-light emitting organic semiconductor device.

On the surface of the thin film thus formed, gold was vapor-deposited through a mask to form source and drain electrodes, thereby providing an organic thin film transistor device having a bottom-gate top-contact structure having a gate width W of 5 mm and a gate length L of 80 μm (the schematic structural illustration shown in FIG. 1).

The FET characteristics of the organic thin film transistor device of Example 4 were evaluated in terms of the carrier mobility and the change in the threshold voltage after repeated driving by using a semiconductor parameter analyzer (4156C, produced by Agilent Technologies, Inc.) having a semi-automatic prober (AX-2000, produced by Vector Semiconductor Co., Ltd.) connected thereto under a normal pressure nitrogen atmosphere.

The results obtained are shown in Table 3 below.

TABLE 3

| Device No. | Organic Semiconductor Material | Carrier Mobility ($cm^2/Vs$) | Change in Threshold Voltage after Repeated Driving | Note |
| --- | --- | --- | --- | --- |
| Device 42 | Compound 5 | $4 \times 10^{-1}$ | A | Invention |
| Device 43 | Compound 7 | 1.6 | A | Invention |
| Device 44 | Compound 8 | 1.1 | A | Invention |

TABLE 3-continued

| Device No. | Organic Semiconductor Material | Carrier Mobility ($cm^2/Vs$) | Change in Threshold Voltage after Repeated Driving | Note |
| --- | --- | --- | --- | --- |
| Device 45 | Compound 10 | 1.5 | A | Invention |
| Device 46 | Compound 11 | 1.2 | A | Invention |
| Device 47 | Compound 12 | $7 \times 10^{-1}$ | A | Invention |
| Device 48 | Compound 13 | $9 \times 10^{-1}$ | A | Invention |
| Device 49 | Compound 19 | $4 \times 10^{-1}$ | A | Invention |
| Device 50 | Compound 23 | $3 \times 10^{-1}$ | A | Invention |
| Device 51 | Compound 24 | $1 \times 10^{-1}$ | A | Invention |
| Device 52 | Compound 43 | $7 \times 10^{-1}$ | A | Invention |
| Device 53 | Compound 44 | $6 \times 10^{-1}$ | A | Invention |
| Device 54 | Compound 50 | $1 \times 10^{-1}$ | A | Invention |
| Device 55 | Compound 51 | $2 \times 10^{-1}$ | A | Invention |
| Device 56 | Compound 53 | $7 \times 10^{-2}$ | A | Invention |
| Device 57 | Compound 93 | $7 \times 10^{-2}$ | A | Invention |
| Device 58 | Compound 112 | 2.1 | A | Invention |
| Device 59 | Compound 117 | 1.4 | A | Invention |
| Device 60 | Compound 125 | $8 \times 10^{-1}$ | A | Invention |
| Comparative Device 7 | Comparative Compound 1 | $1 \times 10^{-5}$ | C | Comparison |
| Comparative Device 8 | Comparative Compound 2 | $5 \times 10^{-3}$ | C | Comparison |
| Comparative Device 9 | Comparative Compound 3 | $6 \times 10^{-4}$ | B | Comparison |

It was understood from Table 3 that the organic thin film transistor devices using the compounds of the invention had a high carrier mobility and a small change in the threshold voltage after repeated driving. Accordingly, it was understood that the compound of the invention was favorably used as an organic semiconductor material for a non-light emitting organic semiconductor device.

On the other hand, the organic thin film transistor devices using the Comparative Compounds 1, 2 and 3 had a low carrier mobility. The organic thin film transistor devices using the Comparative Compounds 1 to 3 had a large change in the threshold voltage after repeated driving.

Instead of using the mixture of the compound of the invention or the comparative compound (1 mg each) and toluene (1 mL) as the coating solution for the non-light emitting organic semiconductor device, when a solution obtained by mixing the compound of the invention or the comparative compound and toluene and heating the mixture to 100° C. was used as the coating solution for the non-light emitting organic semiconductor device, the same results as those shown in Table 3 were obtained.

While the present invention has been described in detail and with reference to specific embodiments thereof, it will be apparent to one skilled in the art that various changes and modifications can be made therein without departing from the spirit and scope thereof.

The present disclosure relates to the subject matter contained in International Application No. PCT/JP2014/057528, filed on Mar. 19, 2014; Japanese Patent Application No. 2013-067346 filed on Mar. 27, 2013; and Japanese Patent Application No. 2014-048650 filed on Mar. 12, 2014, the contents of which are expressly incorporated herein by reference in their entirety. All the publications referred to in the present specification are also expressly incorporated herein by reference in their entirety.

The foregoing description of preferred embodiments of the invention has been presented for purposes of illustration and description, and is not intended to be exhaustive or to limit the invention to the precise form disclosed. The description was selected to best explain the principles of the invention and their practical application to enable others skilled in the art to best utilize the invention in various embodiments and various modifications as are suited to the particular use contemplated. It is intended that the scope of the invention not be limited by the specification, but be defined claims.

What is claimed is:

1. A compound represented by the following formula (1):

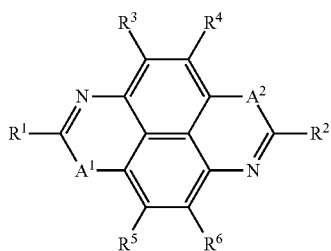

Formula (1)

wherein in the formula (1), $A^1$ and $A^2$ each independently represent a sulfur atom, an oxygen atom or a selenium atom; and $R^1$ to $R^6$ each independently represent a hydrogen atom or a substituent, provided that at least one of $R^1$ to $R^6$ represents a substituent represented by the following formula (W):

\*-L-R   Formula (W)

wherein in the formula (W), \* represents a position bonded to a naphthalene ring in the formula (1), or bonded to a ring containing $A^1$ or a ring containing $A^2$; L represents a divalent linking group represented by any one of the following formulae (L-1) to (L-10), or a divalent linking group consisting of 2 or more divalent linking groups each represented by any one of the following formulae (L-1) to (L-10) in which the 2 or more divalent linking groups are bonded sequentially; and R represents a hydrogen atom, a substituted or unsubstituted alkyl group, an oligooxyethylene group having a repeating number of an oxyethylene unit of 2 or more, an oligosiloxane group having 2 or more silicon atoms, or a substituted or unsubstituted trialkylsilyl group, provided that R represents a hydrogen atom only when L is represented by any one of the formulae (L-1) to (L-3) and (L-8) to (L-10), and R represents a substituted or unsubstituted trialkylsilyl group only when L bonded to R is a divalent linking group represented by the following formula (L-3);

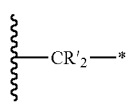   (L-1)

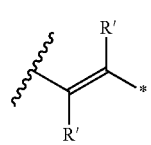   (L-2)

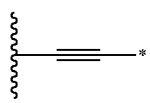   (L-3)

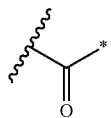   (L-4)

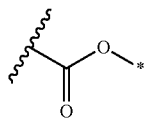   (L-5)

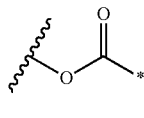   (L-6)

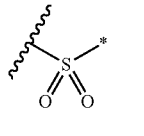   (L-7)

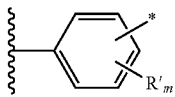   (L-8)

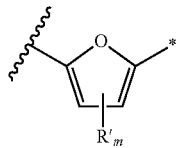   (L-9)

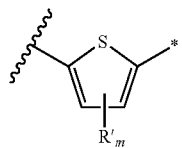   (L-10)

wherein in the formulae (L-1) to (L-10), the wavy line represents a position bonded to any one of a naphthalene ring, a ring containing $A^1$ and a ring containing $A^2$; and \* represents a position bonded to R in the formula (W); in the formula (L-8), m represents 4; in the formulae (L-9) and (L-10), m represents 2; in the formulae (L-1), (L-2), (L-8), (L-9) and (L-10), R' each independently represents a hydrogen atom or a substituent, provided that, in the formulae (L-1) and (L-2), R' each independently may form a condensed ring with R bonded to L.

2. The compound according to claim 1, wherein at least one of $R^1$ and $R^2$ in the formula (1) represents a substituent represented by the formula (W).

3. The compound according to claim 1, wherein the compound represented by the formula (1) is a compound represented by the following formula (2):

Formula (2)

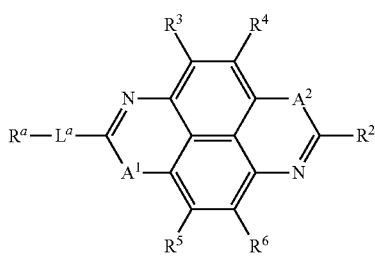

wherein in the formula (2), $A^1$ and $A^2$ each independently represent a sulfur atom, an oxygen atom or a selenium atom; $R^2$ to $R^6$ each independently represent a hydrogen atom or a substituent; $L^a$ represents a divalent linking group represented by any one of the following formulae (L-1) to (L-10), or a divalent linking group consisting of 2 or more divalent linking groups each represented by any one of the following formulae (L-1) to (L-10) in which the 2 or more divalent linking groups are bonded sequentially; and $R^a$ represents a hydrogen atom, a substituted or unsubstituted alkyl group, an oligooxyethylene group having a repeating number of an oxyethylene unit of 2 or more, an oligosiloxane group having 2 or more silicon atoms, or a substituted or unsubstituted trialkylsilyl group, provided that $R^a$ represents a hydrogen atom only when $L^a$ is represented by any one of the formulae (L-1) to (L-3) and (L-8) to (L-10), and $R^a$ represents a substituted or unsubstituted trialkylsilyl group only when $L^a$ bonded to $R^a$ is a divalent linking group represented by the following formula (L-3);

(L-1)
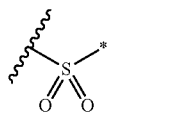

(L-2)
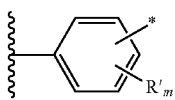

(L-3)
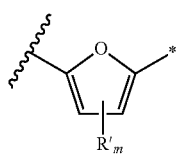

(L-4)
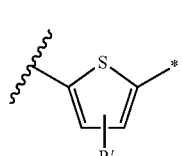

(L-5)

(L-6)

(L-7)
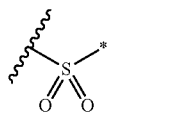

(L-8)
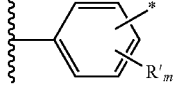

(L-9)
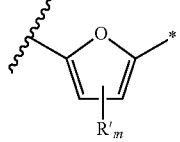

(L-10)

wherein in the formulae (L-1) to (L-10), the wavy line represents a position bonded to any one of a naphthalene ring, a ring containing $A^1$ and a ring containing $A^2$; and * represents a position bonded to $R^a$; in the formula (L-8), m represents 4; in the formulae (L-9) and (L-10), m represents 2; in the formulae (L-1), (L-2), (L-8), (L-9) and (L-10), R' each independently represents a hydrogen atom or a substituent, provided that, in the formulae (L-1) and (L-2), R' each independently may form a condensed ring with R bonded to L.

4. The compound according to claim 1, wherein the compound represented by the formula (1) is a compound represented by the following formula (3):

Formula (3)

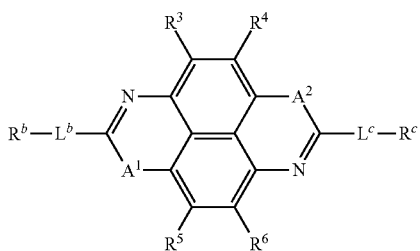

wherein in the formula (3), $A^1$ and $A^2$ each independently represent a sulfur atom, an oxygen atom or a selenium atom; $R^3$ to $R^6$ each independently represent a hydrogen atom or a substituent; $L^b$ and $L^c$ each independently represent a divalent linking group represented by any one of the following formulae (L-1) to (L-10), or a divalent linking group consisting of 2 or more divalent linking groups each represented by any one of the following formulae (L-1) to (L-10) in which the 2 or more divalent linking groups are bonded sequentially; and $R^b$ and $R^c$ each independently represent a hydrogen atom, a substituted or unsubstituted alkyl group, an oligooxyethylene group having a repeating number of an oxyethylene unit of 2 or more, an oligosiloxane group having 2 or more silicon atoms, or a substituted or unsubstituted trialkylsilyl group, provided that $R^b$ and $R^c$ represent a hydrogen atom only when $L^b$ and $L^c$ are represented by any one of the formulae (L-1) to (L-3) and (L-8) to (L-10), and $R^b$ and $R^c$ represent a substituted or unsubstituted trialkylsilyl group only when $L^b$ and $L^c$ each bonded to $R^b$ and $R^c$ are a divalent linking group represented by the following formula (L-3);

(L-1)
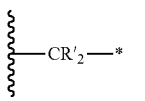

(L-2)
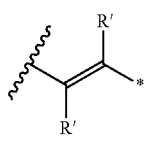

(L-3)
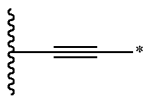

(L-4)
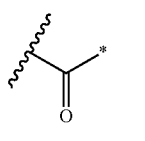

(L-5)
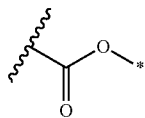

(L-6)
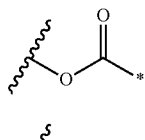

(L-7)
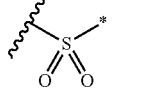

(L-8)
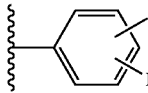

(L-9)
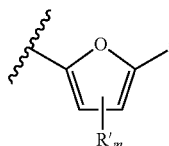

(L-10)
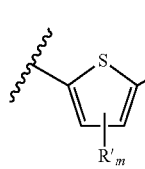

wherein in the formulae (L-1) to (L-10), the wavy line represents a position bonded to any one of a naphthalene ring, a ring containing $A^1$ and a ring containing $A^2$; and * represents a position bonded to $R^b$ or $R^c$; in the formula (L-8), m represents 4; in the formulae (L-9) and (L-10), m represents 2; in the formulae (L-1), (L-2), (L-8), (L-9) and (L-10), R' each independently represents a hydrogen atom or a substituent, provided that, in the formulae (L-1) and (L-2), R' each independently may form a condensed ring with R bonded to L.

5. The compound according to claim 1, wherein $R^3$ to $R^6$ in the formula (1) each independently represent a hydrogen atom, a fluorine atom, a substituted or unsubstituted alkyl group having from 1 to 3 carbon atoms, a substituted or unsubstituted alkynyl group having from 2 to 3 carbon atoms, a substituted or unsubstituted alkenyl group having from 2 to 3 carbon atoms, a substituted or unsubstituted alkoxy group having from 1 to 2 carbon atoms, or a substituted or unsubstituted methylthio group.

6. The compound according to claim 3, wherein all of $L^a$ in the formula (2) each represent a divalent linking group represented by any one of the formulae (L-1) to (L-3), (L-8), (L-9) or (L-10).

7. The compound according to claim 3, wherein all of $L^a$ in the formula (2) each represent a divalent linking group represented by any one of the formula (L-1) or (L-8).

8. The compound according to claim 3, wherein all of $R^a$ in the formula (2) each represent a substituted or unsubstituted alkyl group.

9. The compound according to claim 3, wherein all of $R^a$ in the formula (2) each represent a linear alkyl group.

10. The compound according to claim 1, wherein the compound represented by the formula (1) is a compound represented by the following formula (4):

Formula (4)

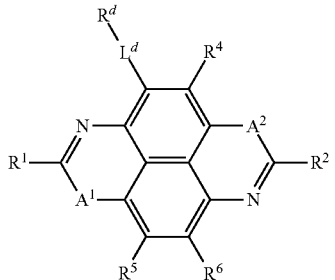

wherein in the formula (4), $A^1$ and $A^2$ each independently represent a sulfur atom, an oxygen atom or a selenium atom; $R^1$ and $R^2$ each independently represent a hydrogen atom or an aryl group, and $R^4$ to $R^6$ each independently represent a hydrogen atom or a substituent; $L^d$ represents a divalent linking group represented by any one of the following formulae (L-1) to (L-10), or a divalent linking group consisting of 2 or more divalent linking groups each represented by any one of the following formulae (L-1) to (L-10) in which the 2 or more divalent linking groups are bonded sequentially; and $R^d$ represents a hydrogen atom, a substituted or unsubstituted alkyl group, an oligooxyethylene group having a repeating number of an oxyethylene unit of 2 or more, an oligosiloxane group having 2 or more silicon atoms, or a substituted or unsubstituted trialkylsilyl group, provided that $R^d$ represents a hydrogen atom only when $L^d$ is represented by any one of the formulae (L-1) to (L-3) and (L-8) to (L-10), and $R^d$ represents a substituted or unsubstituted trialkylsilyl group only when $L^d$ bonded to $R^d$ is a divalent linking group represented by the following formula (L-3);

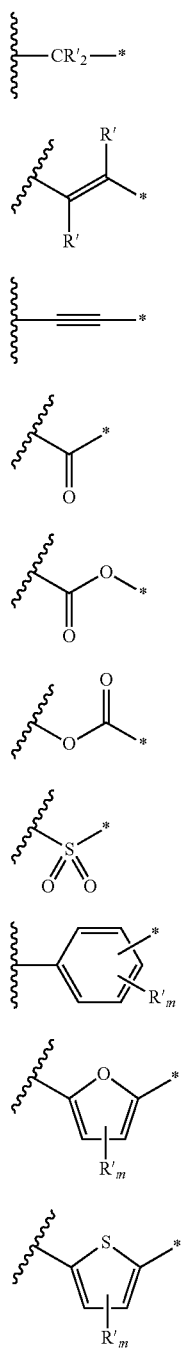

(L-1)
(L-2)
(L-3)
(L-4)
(L-5)
(L-6)
(L-7)
(L-8)
(L-9)
(L-10)

wherein in the formulae (L-1) to (L-10), the wavy line represents a position bonded to a naphthalene ring; and * represents a position bonded to $R^d$; in the formula (L-8), m represents 4; in the formulae (L-9) and (L-10), m represents 2; in the formulae (L-1), (L-2), (L-8), (L-9) and (L-10), R' each independently represents a hydrogen atom or a substituent, provided that, in the formulae (L-1) and (L-2), R' each independently may form a condensed ring with R bonded to L.

11. The compound according to claim 1, wherein the compound represented by the formula (1) is a compound represented by the following formula (5):

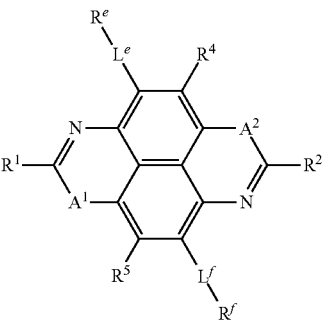

Formula (5)

wherein in the formula (5), $A^1$ and $A^2$ each independently represent a sulfur atom, an oxygen atom or a selenium atom; $R^1$ and $R^2$ each independently represent a hydrogen atom or an aryl group, and $R^4$ and $R^5$ each independently represent a hydrogen atom or a substituent; $L^e$ and $L^f$ each independently represent a divalent linking group represented by any one of the following formulae (L-1) to (L-10), or a divalent linking group consisting of 2 or more divalent linking groups each represented by any one of the following formulae (L-1) to (L-10) in which the 2 or more divalent linking groups are bonded sequentially; and $R^e$ and $R^f$ each independently represent a hydrogen atom, a substituted or unsubstituted alkyl group, an oligooxyethylene group having a repeating number of an oxyethylene unit of 2 or more, an oligosiloxane group having 2 or more silicon atoms, or a substituted or unsubstituted trialkylsilyl group, provided that $R^e$ and $R^f$ represent a hydrogen atom only when $L^e$ and $L^f$ are represented by any one of the formulae (L-1) to (L-3) and (L-8) to (L-10), and $R^e$ and $R^f$ represent a substituted or unsubstituted trialkylsilyl group only when $L^e$ and $L^f$ each bonded to $R^e$ and $R^f$ are a divalent linking group represented by the following formula (L-3);

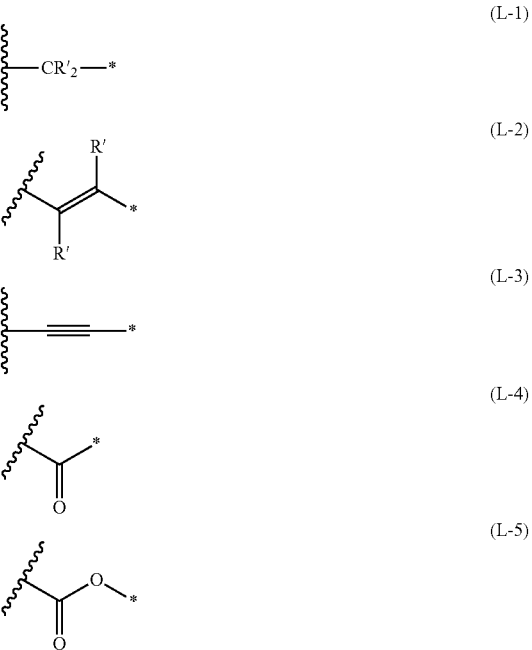

(L-1)
(L-2)
(L-3)
(L-4)
(L-5)

(L-6)
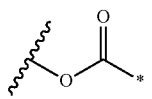

(L-7)
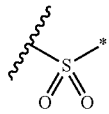

(L-8)
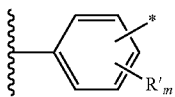

(L-9)
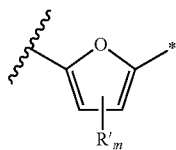

(L-10)
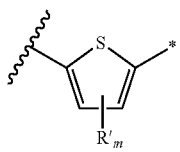

wherein in the formulae (L-1) to (L-10), the wavy line represents a position bonded to a naphthalene ring; and * represents a position bonded to $R^e$ or $R^f$; in the formula (L-8), m represents 4; in the formulae (L-9) and (L-10), m represents 2; in the formulae (L-1), (L-2), (L-8), (L-9) and (L-10), R' each independently represents a hydrogen atom or a substituent, provided that, in the formulae (L-1) and (L-2), R' each independently may form a condensed ring with R bonded to L.

* * * * *